United States Patent
Lee

(10) Patent No.: US 9,502,663 B2
(45) Date of Patent: Nov. 22, 2016

(54) HETEROCYCLIC COMPOUND AND ORGANIC LIGHT EMITTING DEVICE COMPRISING THE SAME

(71) Applicant: Samsung Display Co., Ltd., Yongin, Gyeonggi-Do (KR)

(72) Inventor: Jung-Sub Lee, Yongin (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 439 days.

(21) Appl. No.: 14/026,718

(22) Filed: Sep. 13, 2013

(65) Prior Publication Data

US 2014/0319473 A1     Oct. 30, 2014

(30) Foreign Application Priority Data

Apr. 25, 2013    (KR) .................. 10-2013-0046204

(51) Int. Cl.
| | | |
|---|---|---|
| *H01L 51/00* | (2006.01) | |
| *C07D 487/04* | (2006.01) | |
| *C07D 491/147* | (2006.01) | |
| *C07D 513/04* | (2006.01) | |

(Continued)

(52) U.S. Cl.
CPC ......... *H01L 51/0067* (2013.01); *C07D 487/04* (2013.01); *C07D 491/147* (2013.01); *C07D 513/04* (2013.01); *C07D 513/14* (2013.01); *C07D 519/00* (2013.01); *C07F 7/0812* (2013.01); *H01L 51/0052* (2013.01);

(Continued)

(58) Field of Classification Search
None
See application file for complete search history.

(56) References Cited

U.S. PATENT DOCUMENTS

| 6,821,643 | B1 | 11/2004 | Hu et al. | |
|---|---|---|---|---|
| 2006/0113905 | A1 * | 6/2006 | Nakamura | .......... H01L 27/3244 |
| | | | | 313/511 |

(Continued)

FOREIGN PATENT DOCUMENTS

| CN | 101402595 A * | 8/2009 | .......... C07C 323/38 |
|---|---|---|---|
| KR | 10-2010-0039792 A | 4/2010 | |

(Continued)

OTHER PUBLICATIONS

Johansson et al., "Solid-State Amplified Spontaneous Emission in Some Spiro-Type Molecules: A New Concept for the Design of Solid-State Lasing Molecules", Advanced Materials, 1998, vol. 10, No. 14, pp. 1136-1141.

(Continued)

*Primary Examiner* — J. L. Yang
(74) *Attorney, Agent, or Firm* — Knobbe Martens Olson & Bear LLP

(57) ABSTRACT

A compound represented by Formula 1 below and an organic light-emitting device including the compound are provided:

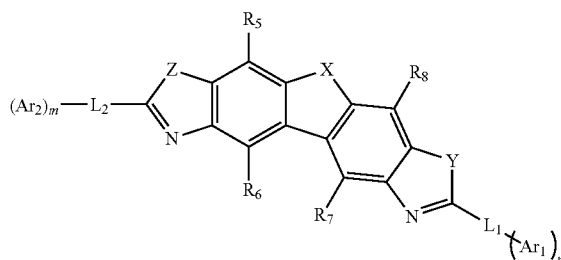

Formula 1

Substituents in Formula 1 are the same as defined in the specification.

20 Claims, 1 Drawing Sheet

(51) Int. Cl.
*C07D 513/14* (2006.01)
*C07D 519/00* (2006.01)
*C07F 7/08* (2006.01)
*H01L 51/50* (2006.01)

(52) U.S. Cl.
CPC ....... *H01L51/0058* (2013.01); *H01L 51/0069* (2013.01); *H01L 51/0071* (2013.01); *H01L 51/0072* (2013.01); *H01L 51/0094* (2013.01); *H01L 51/5072* (2013.01); *H01L 51/006* (2013.01); *H01L 51/0059* (2013.01); *H01L 51/504* (2013.01)

(56) References Cited

U.S. PATENT DOCUMENTS

| | | | |
|---|---|---|---|
| 2006/0131562 A1* | 6/2006 | Li | ........................ H01L 51/002 257/40 |
| 2010/0200054 A1 | 8/2010 | Jung et al. | |
| 2012/0080670 A1 | 4/2012 | Park et al. | |
| 2012/0112174 A1 | 5/2012 | Lee et al. | |

FOREIGN PATENT DOCUMENTS

| | | | | |
|---|---|---|---|---|
| KR | 10-2011-0058248 A | 6/2011 | | |
| KR | 10-2011-0068162 A | 6/2011 | | |
| KR | 10-2012-0047706 A | 5/2012 | | |
| WO | WO-2011/126225 A1 * | 10/2011 | ............. | C09K 11/06 |

OTHER PUBLICATIONS

Uchida et al., "Structural Optimization of 2,5-Diarylsiloles as Excellent Electron-Transporting Materials for Organic Electroluminescent Devices", Chem. Mater., 2001, vol. 13, pp. 2680-2683.

Tao et al., "Sharp green electroluminescence from 1H-pyrozolo {3,4-b] quinolone-based light-emitting diodes", Applied Physics Letters, Sep. 11, 2000, vol. 77, No. 11, pp. 1575-1577.

* cited by examiner

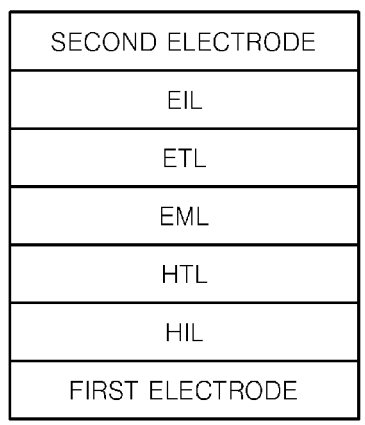

HETEROCYCLIC COMPOUND AND ORGANIC LIGHT EMITTING DEVICE COMPRISING THE SAME

RELATED APPLICATIONS

This application claims the benefit of Korean Patent Application No. 10-2013-0046204, filed on Apr. 25, 2013, in the Korean Intellectual Property Office, the disclosure of which is incorporated herein by reference.

BACKGROUND

Field

One or more embodiments relate to a heterocyclic compound and an organic light-emitting device including the heterocyclic compound.

Description of the Related Technology

Organic light-emitting device (OLEDs), which are self-emitting devices, have advantages such as wide viewing angles, excellent contrast, quick response, high brightness, excellent driving voltage characteristics, and can provide multicolored images.

A typical OLED has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films comprising organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

There is an ongoing demand for a material having improved electrical stability, high charge-transfer or emission capability, and a high glass transition temperature that is high enough to prevent crystallization, in regards to existing unimolecular materials.

SUMMARY

One or more embodiments include a novel compound that may prevent crystallization when used to manufacture a device and that have good film formability. The novel compound is available as an electron transport material suitable for fluorescent or phosphorescent device of any color of red, green, blue, or white, and include an organic light-emitting device manufactured using the novel compound and having high efficiency, low driving voltage, high luminance, and long lifetime.

Additional aspects will be set forth in part in the description which follows and, in part, will be apparent from the description, or may be learned by practice of the presented embodiments.

According to one or more embodiments, there is provided a heterocyclic compound represented by Formula 1 below:

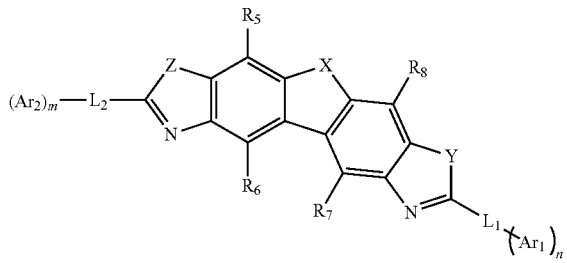

<Formula 1> wherein, in Formula 1,

X is $CR_1R_2$, $SiR_3R_4$, S, or O;

Y and Z are each independently $NAr_3$, S, or O;

$R_1$ to $R_8$ are each independently a hydrogen atom, a deuterium atom, a cyano group, a substituted or unsubstituted C1-20 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C3-C60 cycloalkenyl group, a substituted or unsubstituted C6-C60 aryl group, a substituted or unsubstituted C2-C60 heteroaryl group, or a substituted or unsubstituted C6-C60 condensed polycyclic group;

$L_1$ and $L_2$ are each independently a bond, a substituted or unsubstituted C6-C60 arylene group, or a substituted or unsubstituted C2-C60 heteroarylene group;

$Ar_1$ to $Ar_3$ are the same or different, and are each independently a substituted or unsubstituted C2-C60 heteroaryl group, a substituted or unsubstituted C6-C60 aryl group, or a substituted or unsubstituted C6-C60 condensed polycyclic group; and m and n are each independently an integer from 0 to 3, and m and n are not both zero.

According to one or more embodiments, an organic light-emitting device includes: a first electrode; a second electrode; and an organic layer disposed between the first electrode and the second electrode, and including the heterocyclic compound of Formula 1 above.

According to one or more embodiments, a flat panel display device includes the above-defined organic light-emitting device, wherein the first electrode of the organic light-emitting device is electrically connected to a source electrode or a drain electrode of a thin-film transistor.

BRIEF DESCRIPTION OF THE DRAWINGS

These and/or other aspects will become apparent and more readily appreciated from the following description of the embodiments, taken in conjunction with the accompanying drawing of which:

FIG. 1 schematically illustrates the structure of an organic light-emitting device according to an embodiment.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an aspect of the present embodiments, there is provided an organic light-emitting compound represented by Formula 1 below.

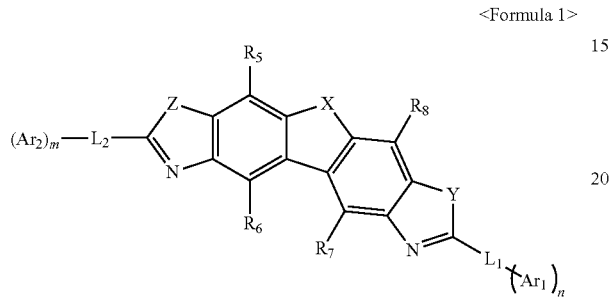

<Formula 1>

In Formula 1,

X is $CR_1R_2$, $SiR_3R_4$, S, or O;

Y and Z are each independently $NAr_3$, S, or O;

$R_1$ to $R_8$ are each independently a hydrogen atom, a deuterium atom, a cyano group, a substituted or unsubstituted C1-20 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C3-C60 cycloalkenyl group, a substituted or unsubstituted C6-C60 aryl group, a substituted or unsubstituted C2-C60 heteroaryl group, or a substituted or unsubstituted C6-C60 condensed polycyclic group;

$L_1$ and $L_2$ are each independently a bond, a substituted or unsubstituted C6-C60 arylene group, or a substituted or unsubstituted C2-C60 heteroarylene group;

$Ar_1$ to $Ar_a$ are the same or different, and are each independently a substituted or unsubstituted C2-C60 heteroaryl group, a substituted or unsubstituted C6-C60 aryl group, or a substituted or unsubstituted C6-C60 condensed polycyclic group; and m and n are each independently an integer from 0 to 3, and m and n are not both zero.

Typical electron transport materials are aluminum complexes, such as tris(8-hydroxyquinoline)aluminum(III) (Alq), used before the use of multi-layer thin film OLEDs disclosed by Kodak in 1987, and beryllium complexes (Bebq), such as bis(10-hydroxybenzo-[h]quinolinato)beryllium (Bebq). However, limitations of these materials arisen with the commercialization of OLEDs in 2002 have accelerated research into other alternative high-performance electron transport materials, which are currently near the commercialization stage.

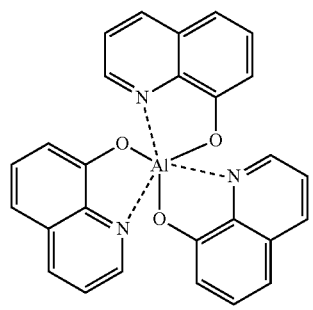

Alq

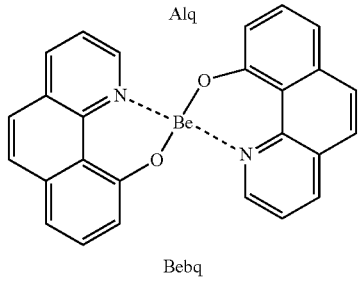

Bebq

Non-metal complex-based electron transport materials with good characteristics disclosed so far are spiro-PBD, PyPySPyPy, and Kodak's TPBI, but which still need further improvements in light-emitting characteristics and lifetime characteristics.

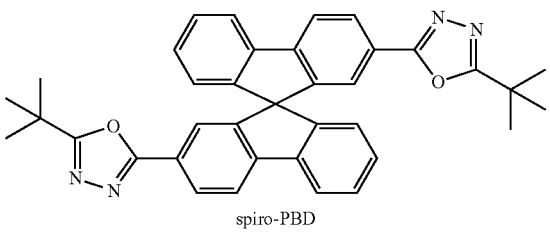

spiro-PBD

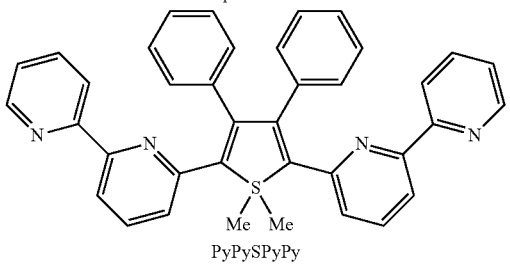

PyPySPyPy

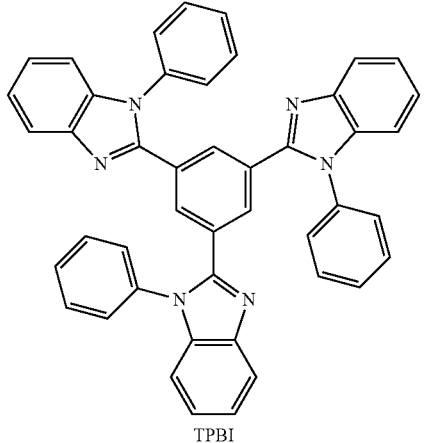

TPBI

However, these conventional electron transport materials have drawbacks, such as minor actual improvements in driving voltage that are not so high as disclosed in the research reports, markedly short lifetimes with variations for each color, and low thermal stability. These drawbacks of the conventional electron transport materials are main obstacles to developing large-screen OLED panels that require low power consumption and high luminance.

Substituents in the compound of Formula 1 will now be described in detail.

In some embodiments, $R_5$ to $R_8$ in Formula 1 are each independently a hydrogen atom or a deuterium atom.

In some embodiments, $L_1$ and $L_2$ in Formula 1 are each independently a bond or a group represented by Formula 2a below:

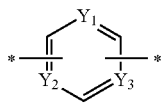

2a

In Formula 2a, $Y_1$ to $Y_3$ are each independently CH, or N.

In some embodiments, $Ar_1$ and $Ar_2$ in Formula 1 are each independently one of the groups represented by Formulae 3a to 3g below:

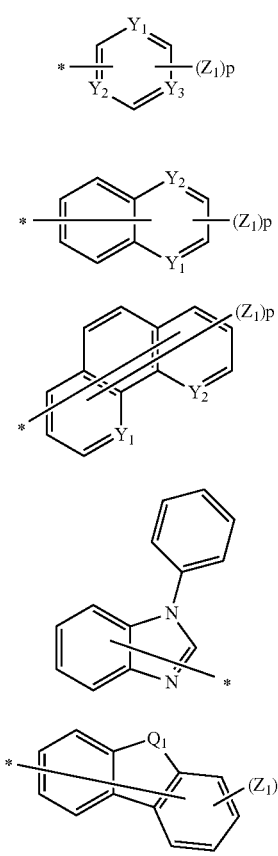

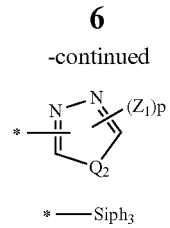

In Formulae 3a to 3g,
$Y_1$ to $Y_3$ are each independently CH or N;
$Q_1$ is $SiR_{50}R_{51}$;
$Q_2$ is S or $NR_{60}$;
$R_{50}$, $R_{51}$, $R_{60}$, and $Z_1$ are each independently a hydrogen atom, a deuterium atom, a substituted or unsubstituted C1-20 alkyl group, a substituted or unsubstituted C6-C20 aryl group, a substituted or unsubstituted C2-C20 heteroaryl group, a substituted or unsubstituted C6-C20 condensed polycyclic group, an amino group substituted with a C6-C20 aryl group or a C2-C20 heteroaryl group, a halogen group, a cyano group, a nitro group, a hydroxy group, or a carboxyl group, wherein a plurality of $Z_1$s are the same or different;
p is an integer from 1 to 7; and
* indicates a binding site.

In some embodiments, adjacent substituents of $R_1$ to $R_4$ in Formula 1 are linked to each other to form a ring.

In some embodiments, when $Ar_1$ or $Ar_2$ in Formula 1 is plural, adjacent substituents of $Ar_1$ or $Ar_2$ are linked to each other to form a ring.

Hereinafter, substituents described with reference to the formulae will now be described in detail. In this regard, the numbers of carbons in substituents are presented only for illustrative purposes and do not limit the characteristics of the substituents. The substituents not defined herein have general meanings.

The unsubstituted C1-C60 alkyl group used herein may be linear or branched. Examples of the alkyl group may include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with a deuterium atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a C1-10 alkyl group, a C1-C10 alkoxy group, a C2-C10 alkenyl group, a C2-C10 alkynyl group, a C6-C16 aryl group, or a C2-C16 heteroaryl group.

The unsubstituted C2-C60 alkenyl group indicates an unsaturated alkyl groups having at least one carbon-carbon double bond in the center or at a terminal of the alkyl group. Examples of the alkenyl group are an ethenyl group, a propenyl group, a butenyl group, and the like. At least one hydrogen atom in the unsubstituted alkenyl group may be substituted with a substituent described above in conjunction with the alkyl group.

The unsubstituted C2-C60 alkynyl group indicates an alkyl group having at least one carbon-carbon triple bond in the center or at a terminal of the alkyl group. Non-limiting examples of the unsubstituted C2-C20 alkynyl group are acetylene, propylene, phenylacetylene, naphthylacetylene, isopropylacetylene, t-butylacetylene, and diphenylacetylene. At least one hydrogen atom in the alkynyl group may be substituted with a substituent described above in conjunction with the alkyl group.

The unsubstituted C3-C60 cycloalkyl group indicates a C3-C60 cyclic alkyl group wherein at least one hydrogen atom in the cycloalkyl group may be substituted with a substituent described above in conduction with the C1-C60 alkyl group.

The unsubstituted C1-C60 alkoxy group indicates a group having a structure of —OA wherein A is an unsubstituted C1-C60 alkyl group as described above. Non-limiting examples of the unsubstituted C1-C60 alkoxy group are a methoxy group, an ethoxy group, a propoxy group, an isopropyloxy group, a butoxy group, and a pentoxy group. At least one hydrogen atom of the alkoxy group may be substituted with a substituent such as those described above in conjunction with the alkyl group.

The unsubstituted C6-C60 aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with those substituents described above in conjunction with the unsubstituted C1-C60 alkyl group.

Non-limiting examples of the substituted or unsubstituted C6-C60 aryl group are a phenyl group, a C1-C10 alkylphenyl group (for example, an ethylphenyl group), a biphenyl group, C1-C10 alkylbiphenyl group, a C1-C10 alkoxybiphenyl group, an o-, m-, and p-tolyl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a C1-C10 alkylnaphthyl group (for example, a methylnaphthyl group), a C1-C10 alkoxynaphthyl group (for example, a methoxynaphthyl group), an anthracenyl group, an azrenyl group, a heptalenyl group, an acenaphthylenyl group, a phenalenyl group, a fluorenyl group, an anthraquinolyl group, a methylanthryl group, a phenanthryl group, a triphenylene group, a pyreny group, a chrysenyl group, an ethyl-chrysenyl group, a picenyl group, a perylenyl group, a pentaphenyl group, a pentasenyl group, a tetraphenyleny group, a hexaphenyl group, a hexacenyl group, a rubicenyl group, a coroneryl group, a trinaphthylenyl group, a heptaphenyl group, a heptacenyl group, a piranthrenyl group, and an obarenyl group.

The unsubstituted C2-C60 heteroaryl group used herein includes one, two, three, or four hetero atoms selected from N, O, P and S. At least two rings may be fused to each other or linked to each other by a single bond. Non-limiting examples of the unsubstituted C2-C60 heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the heteroaryl group may be substituted with a substituent described above in conjunction with the unsubstituted C1-C60 alkyl group.

The unsubstituted C6-C60 aryloxy group is a group represented by —OA$_1$ wherein A$_1$ may be a C6-C60 aryl group. An example of the aryloxy group is a phenoxy group. At least one hydrogen atom in the aryloxy group may be substituted with a substituent described above in conjunction with the unsubstituted C1-C60 alkyl group.

The unsubstituted C6-C60 arylthio group is a group represented by —SA$_1$ wherein A$_1$ may be a C6-C60 aryl group. Non-limiting examples of the arylthio group are a benzenethio group and a naphthylthio group. At least one hydrogen atom in the arylthio group may be substituted with a substituent described above in conjunction with the unsubstituted C1-C60 alkyl group.

The unsubstituted C6-C60 condensed polycyclic group used herein refers to a substituent including at least two rings wherein at least one aromatic ring and/or at least one non-aromatic ring are fused to each other, or refers to a substituent having an unsaturated group in a ring that may not form a conjugate structure. The unsubstituted C6-C60 condensed polycyclic group is distinct from an aryl group or a heteroaryl group in terms of being non-aromatic.

Non-limiting examples of the compound represented by Formula 1 are compounds represented by the following formulae.

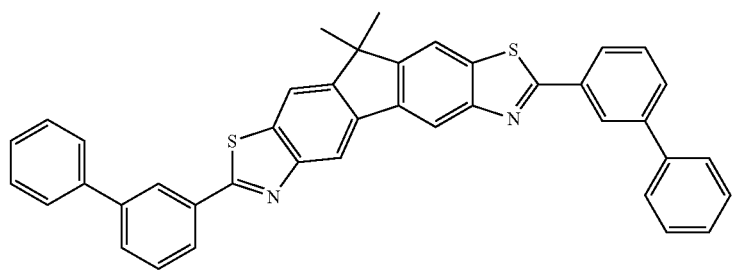

1

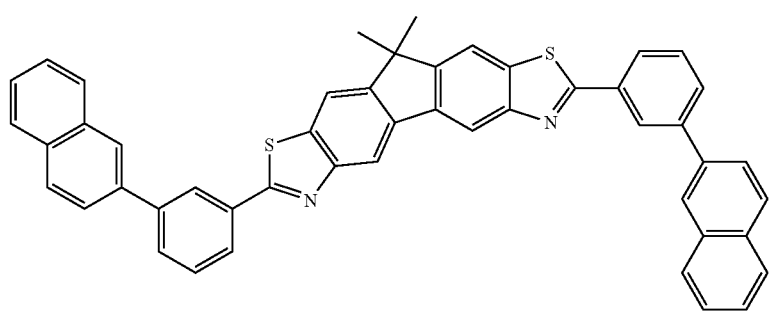

2

-continued
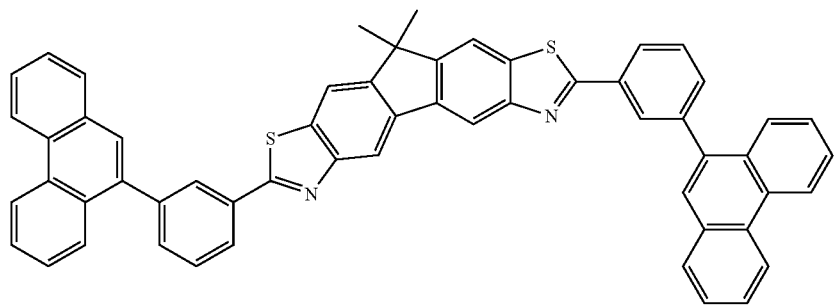
3
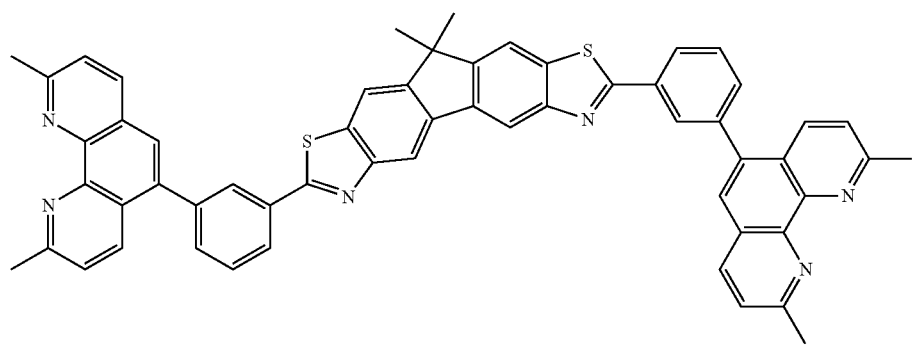
4
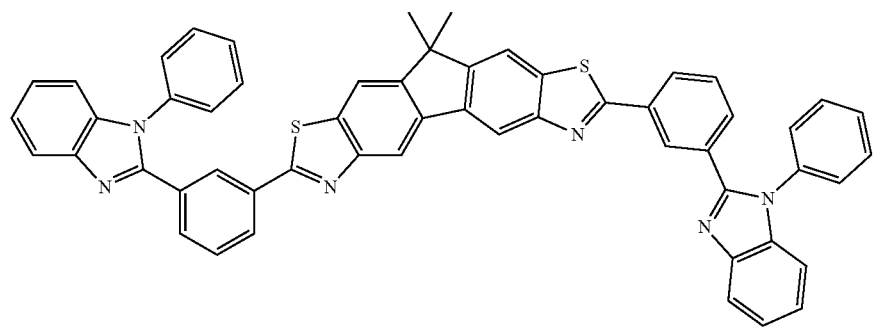
5
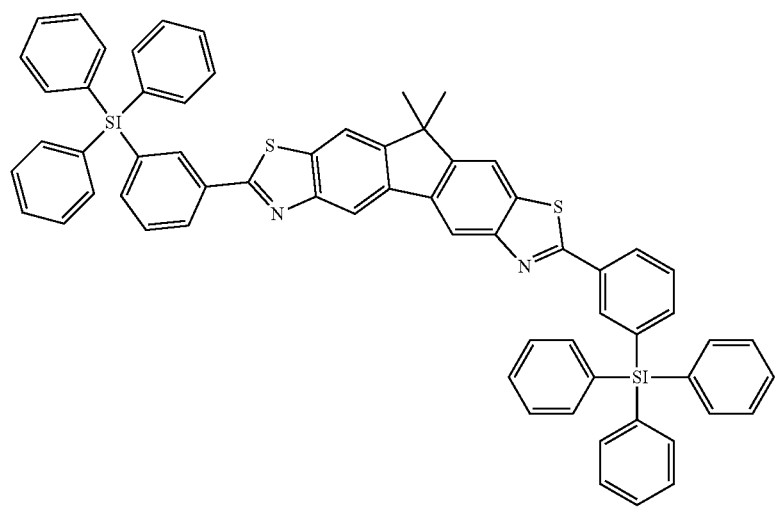
6

-continued
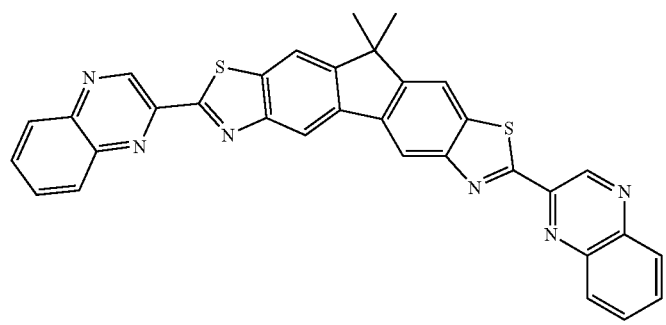
7
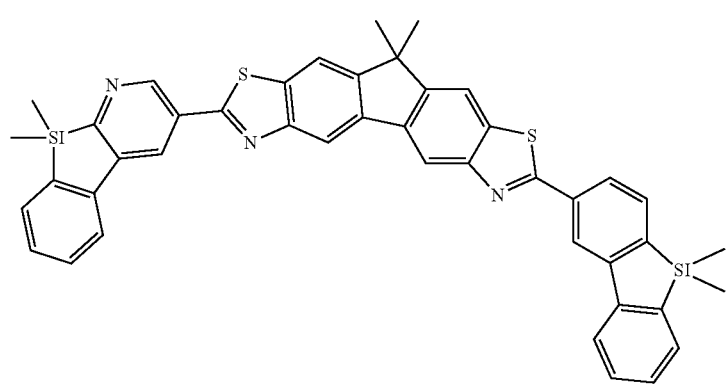
8
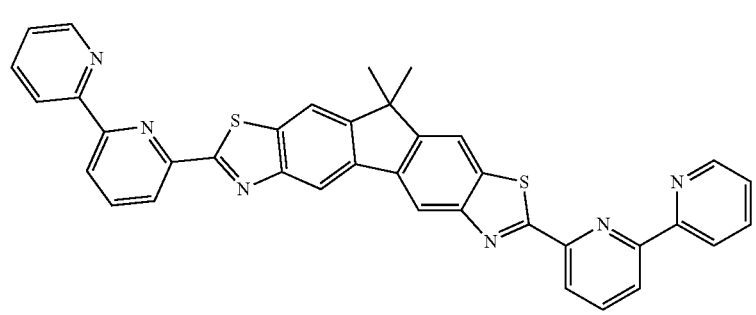
9
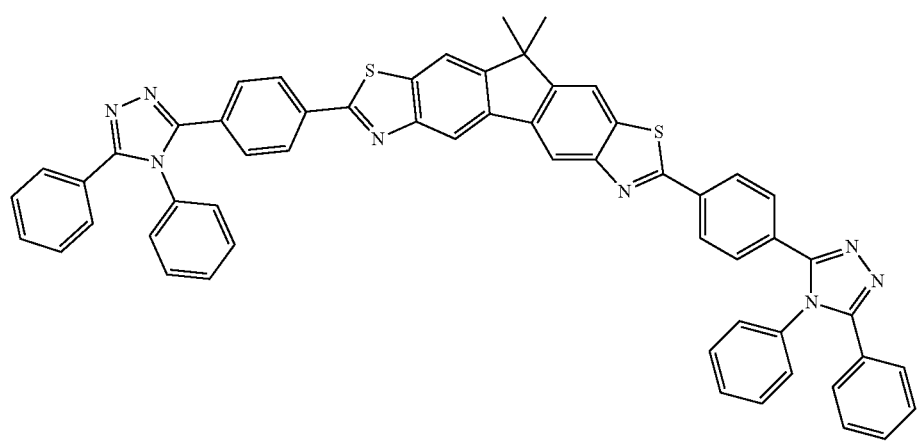
10

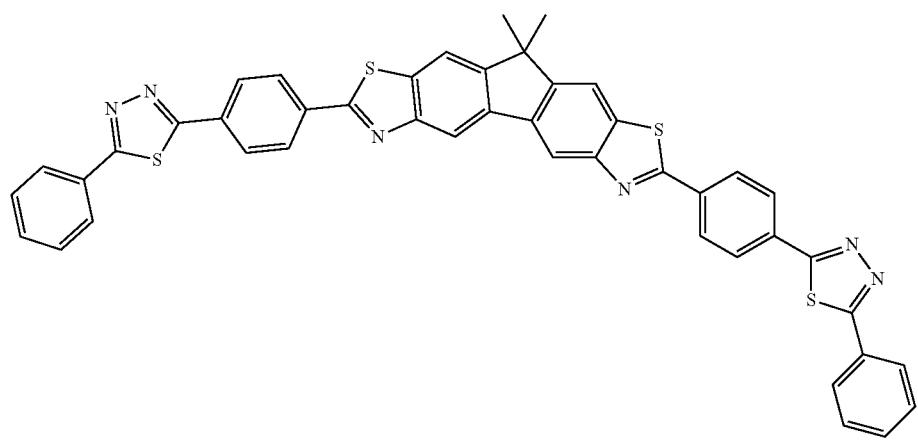
11
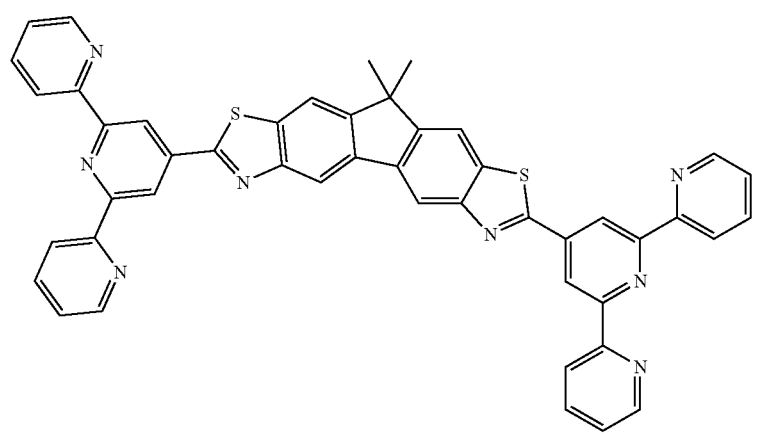
12
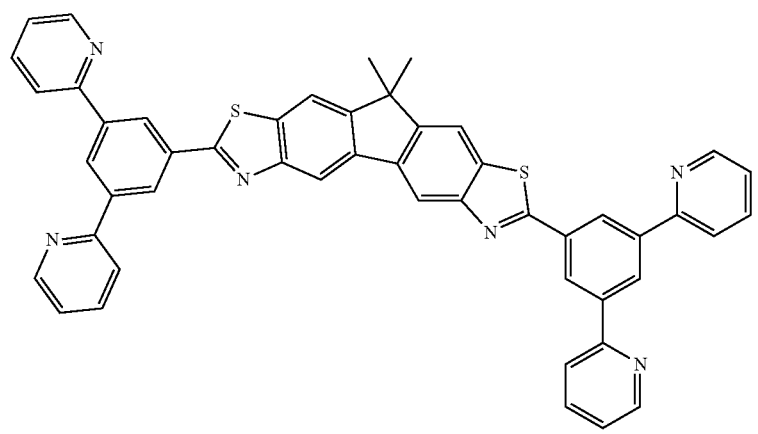
13

-continued
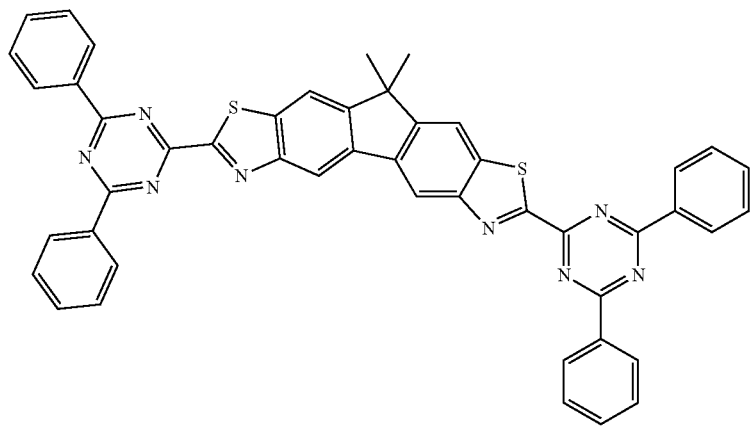
14
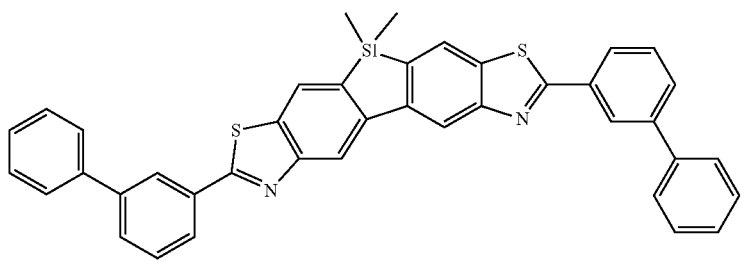
15
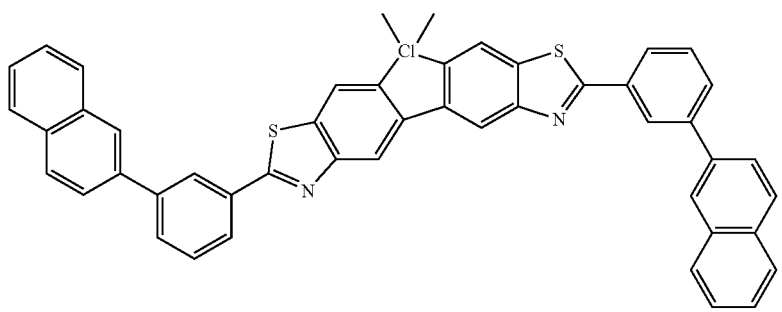
16
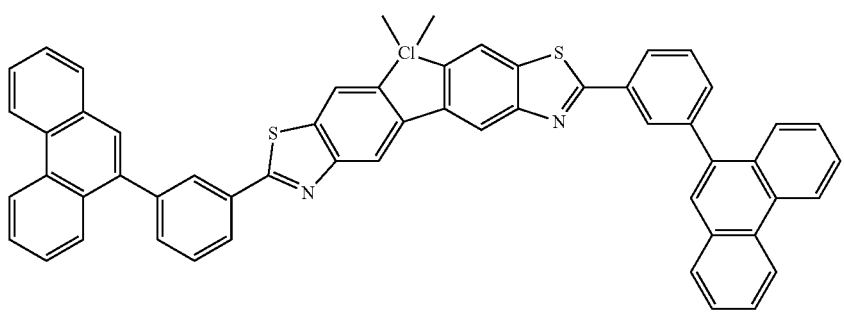
17
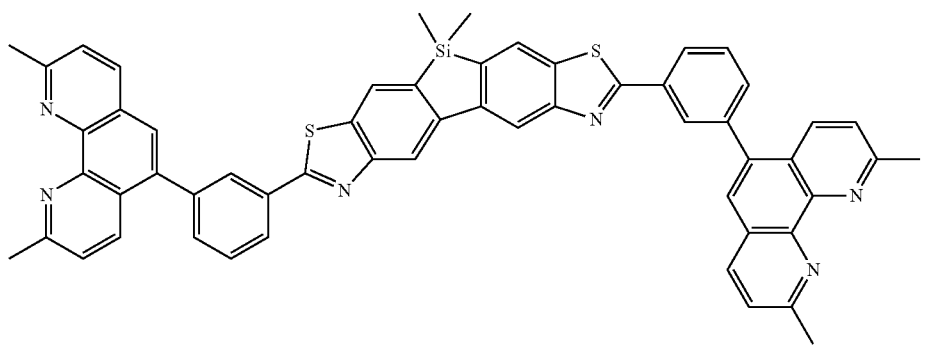
18

-continued
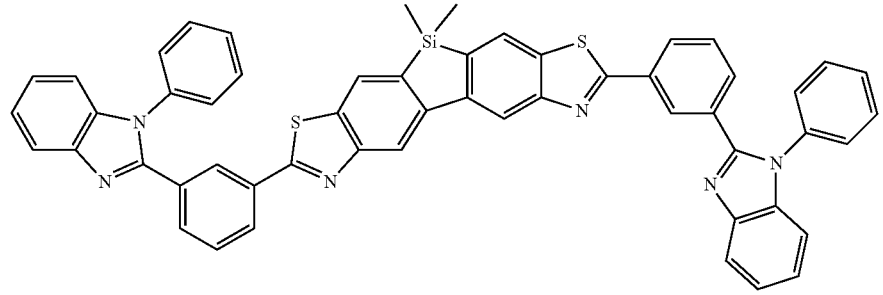
19
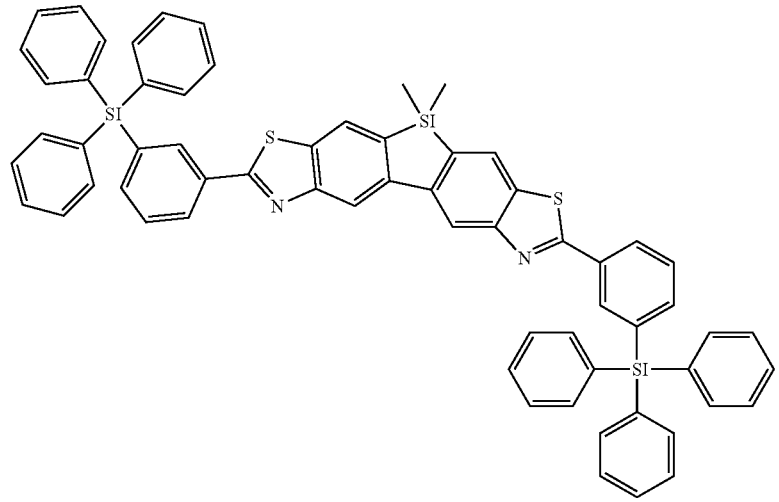
20
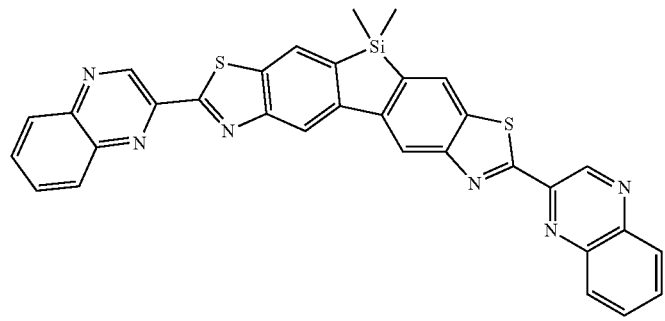
21
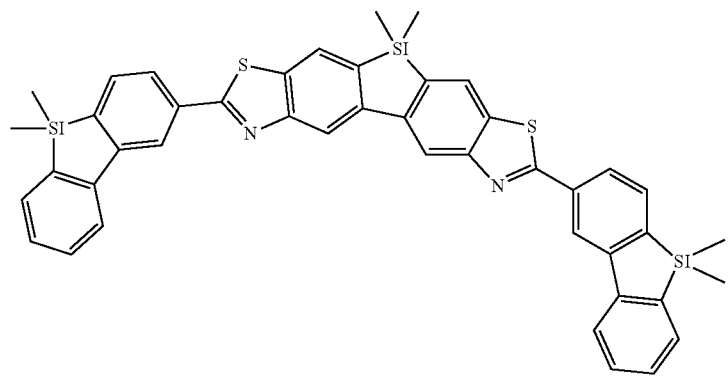
22

23
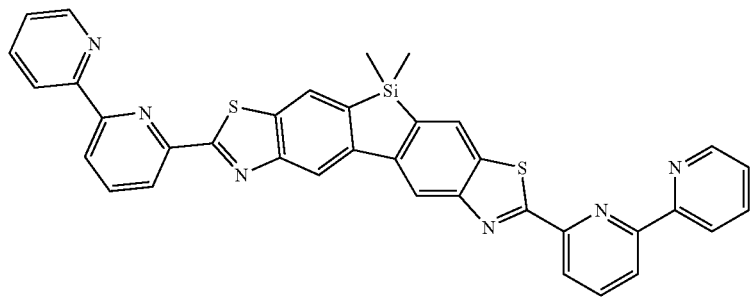
24
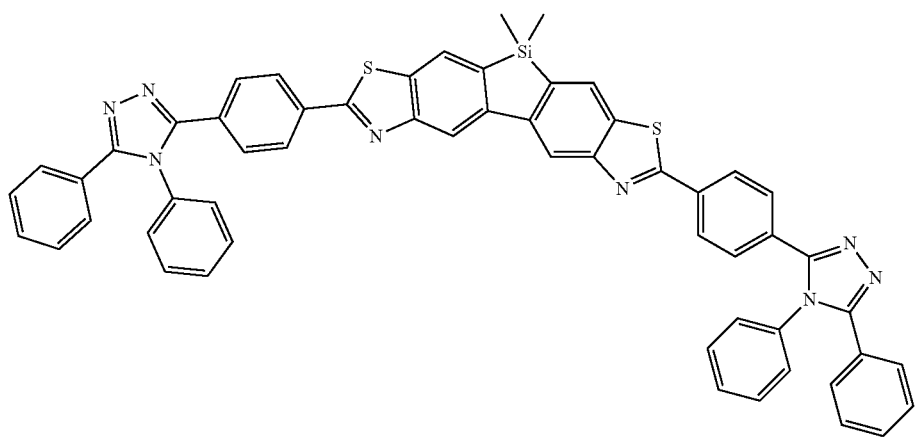
25
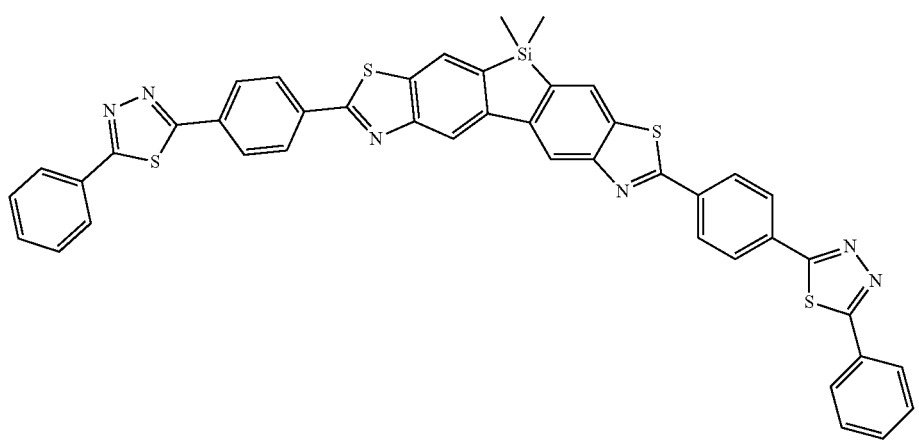
26
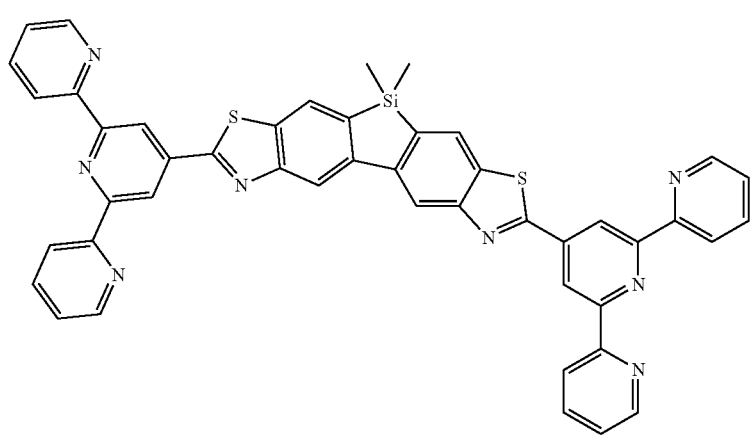

27
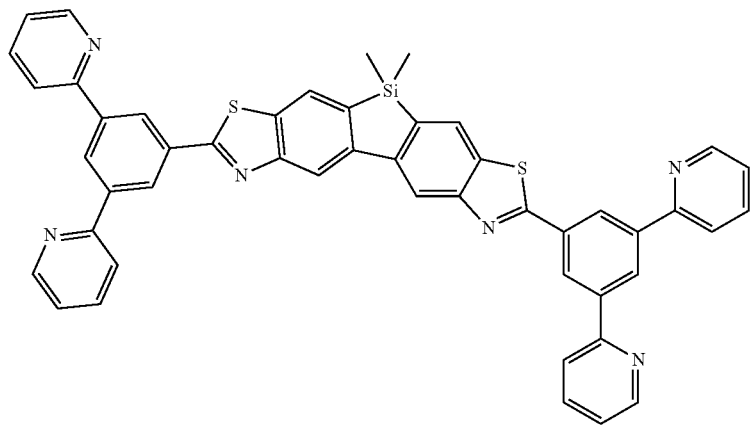
28
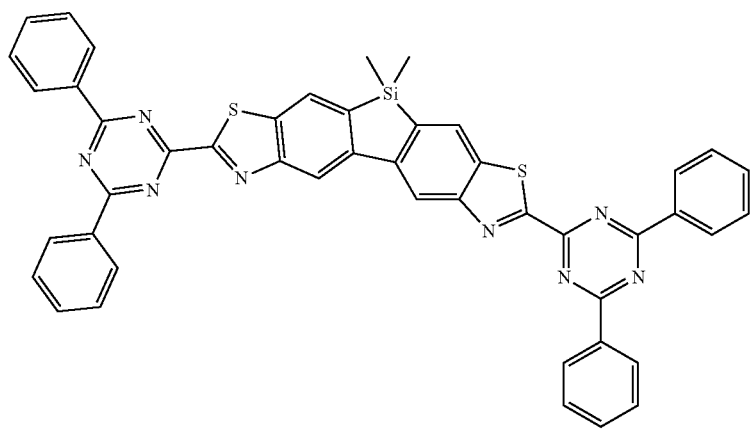
29
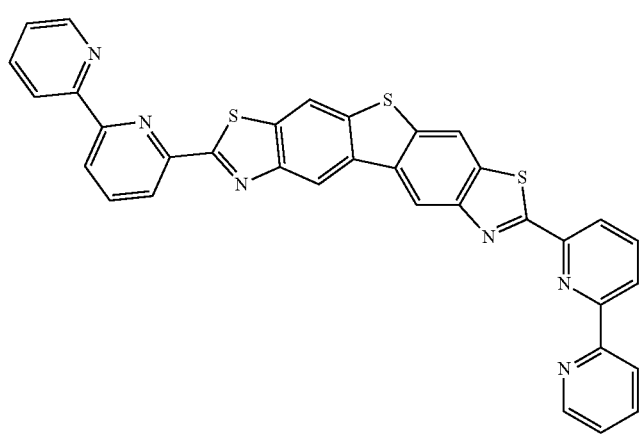
30
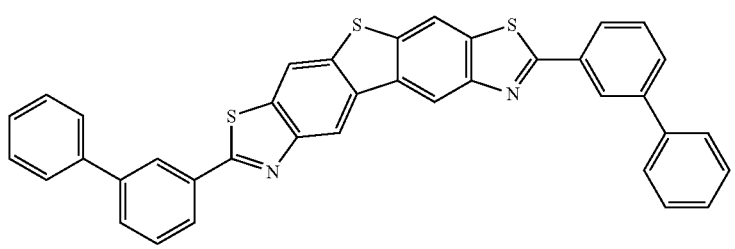

-continued
31
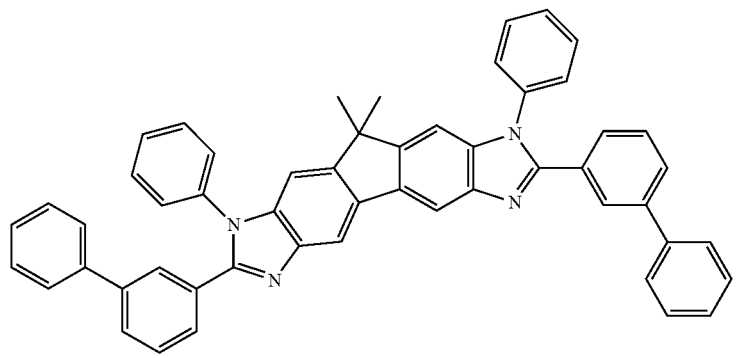
32
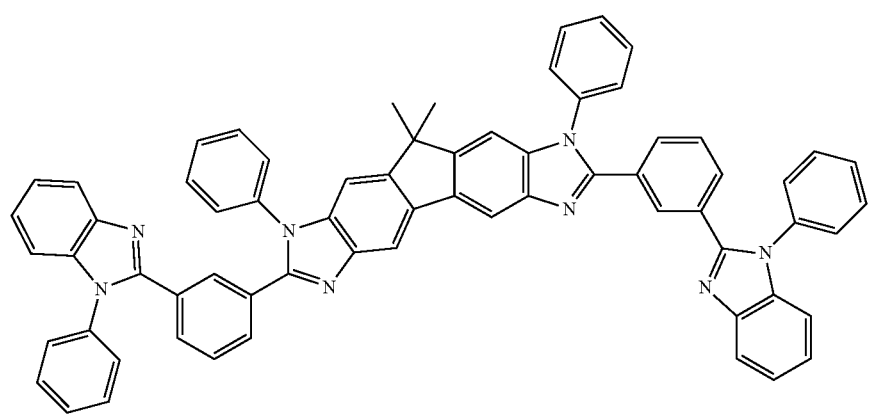
33
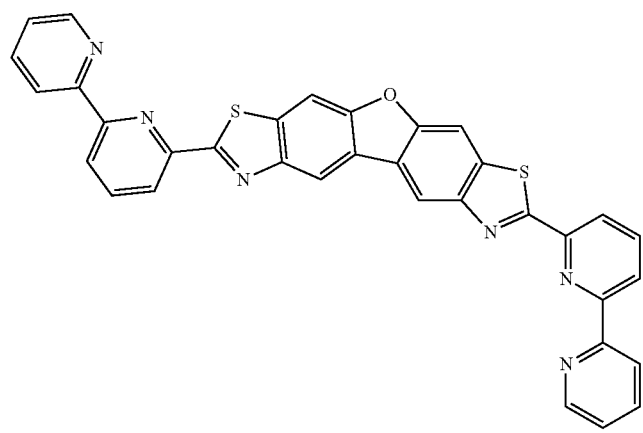
34
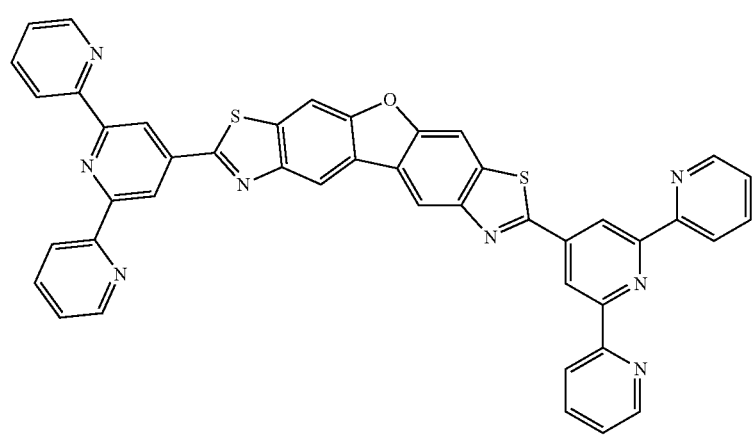

35

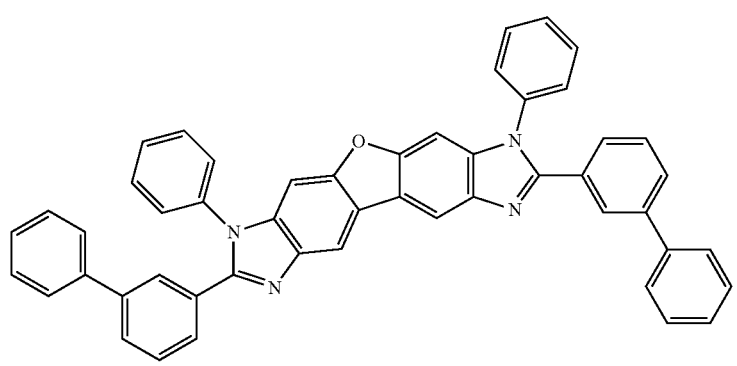

36

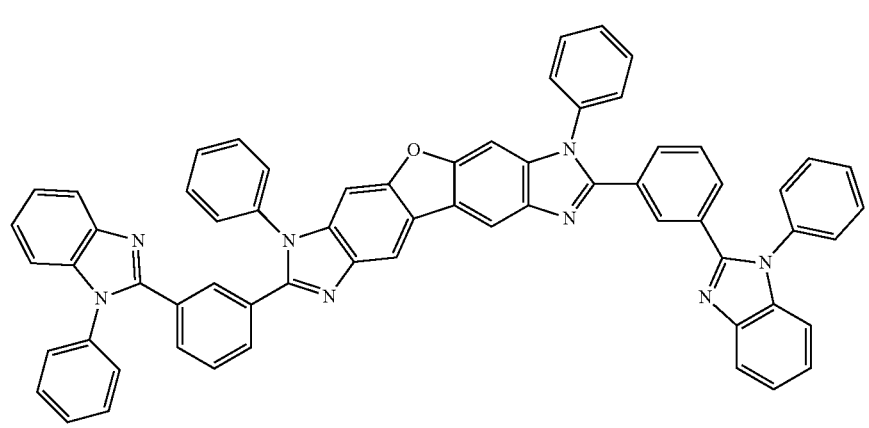

Another aspect of the present embodiments provides an organic light-emitting device including a first electrode, a second electrode, and an organic film disposed between the first electrode and the second electrode, wherein the organic film includes the compound of Formula 1 described above.

The organic layer may include at least one layer selected from among a hole injection layer, a hole transport layer, a functional layer having both hole injection and hole transport capabilities (hereinafter, a "H-functional layer"), a buffer layer, an electron blocking layer, an emission layer, a hole blocking layer, an electron transport layer, an electron injection layer, and a functional layer having both electron injection and electron transport capabilities (hereinafter, an "E-functional layer").

For example, the organic layer may be an electron transport layer.

In some embodiments, the organic layer may include an electron injection layer, an electron transport layer, an emission layer, a hole injection layer, a hole transport layer, or a functional layer having both hole injection and transport capabilities; and the emission layer may include an anthracene-based compound, an arylamine-based compound or a styryl-based compound.

In some other embodiments, the organic layer may include an electron injection layer, an electron transport layer, an emission layer, a hole injection layer, a hole transport layer, or a functional layer having both hole injection and transport capabilities; at least one of a red emission layer, a green emission layer, a blue emission layer, and a white emission layer of the emission layer may include a phosphorescent compound; and at least one of the hole injection layer, the hole transport layer, and the functional layer having both hole injection and hole transport capabilities may include a charge-generating material. In some embodiments, the charge-generating material may be a p-type dopant, and the p-type dopant may be a quinine derivative, a metal oxide or a cyano group-containing compound.

In some embodiments, the organic film may include an electron transport layer, and the electron transport layer may include an electron-transporting organic compound and a meta complex. The metal complex may be a lithium (Li) complex.

The term "organic layer" as used herein refers to a single layer and/or a plurality of layers disposed between the first and second electrodes of the organic light-emitting device.

FIG. 1 is a schematic sectional view of an organic light-emitting device according to an embodiment. Hereinafter, a structure of an organic light-emitting device according to an embodiment and a method of manufacturing the same will now be described with reference to FIG. 1.

A substrate (not shown) may be any substrate that is used in existing organic light emitting devices. In some embodiments the substrate 11 may be a glass substrate or a transparent plastic substrate with strong mechanical strength, thermal stability, transparency, surface smoothness, ease of handling, and water resistance.

The first electrode may be formed by depositing or sputtering a first electrode-forming material on the substrate. When the first electrode is an anode, a material having a high work function may be used as the first electrode-forming material to facilitate hole injection. The first electrode may be a reflective electrode or a transmission electrode. Transparent and conductive materials such as ITO, IZO, $SnO_2$, and ZnO may be used to form the first electrode. The first electrode may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode 13 may have a single-layer structure or a multi-layer structure including at least two layers. For example, the first electrode may have a three-layered structure of ITO/Ag/ITO, but is not limited thereto.

An organic layer(s) is disposed on the first electrode.

The organic layer may include a hole injection layer (HIL), a hole transport layer (HTL), a buffer layer (not shown), an emission layer (EML), an electron transport layer (ETL), or an electron injection layer (EIL).

The HIL may be formed on the first electrode by vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

The HIL may comprise any material that is commonly used to form a HIL. Non-limiting examples of the material that may be used to form the HIL are N,N'-diphenyl-N,N'-bis-[4-(phenyl-m-tolyl-amino)-phenyl]-biphenyl-4,4'-diamine (DNTPD), a phthalocyanine compound such as copperphthalocyanine, 4,4',4''-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrene sulfonate) (PEDOT/PSS), polyaniline/camphor sulfonic acid (Pani/CSA), and polyaniline)/poly(4-styrenesulfonate (PANI/PSS).

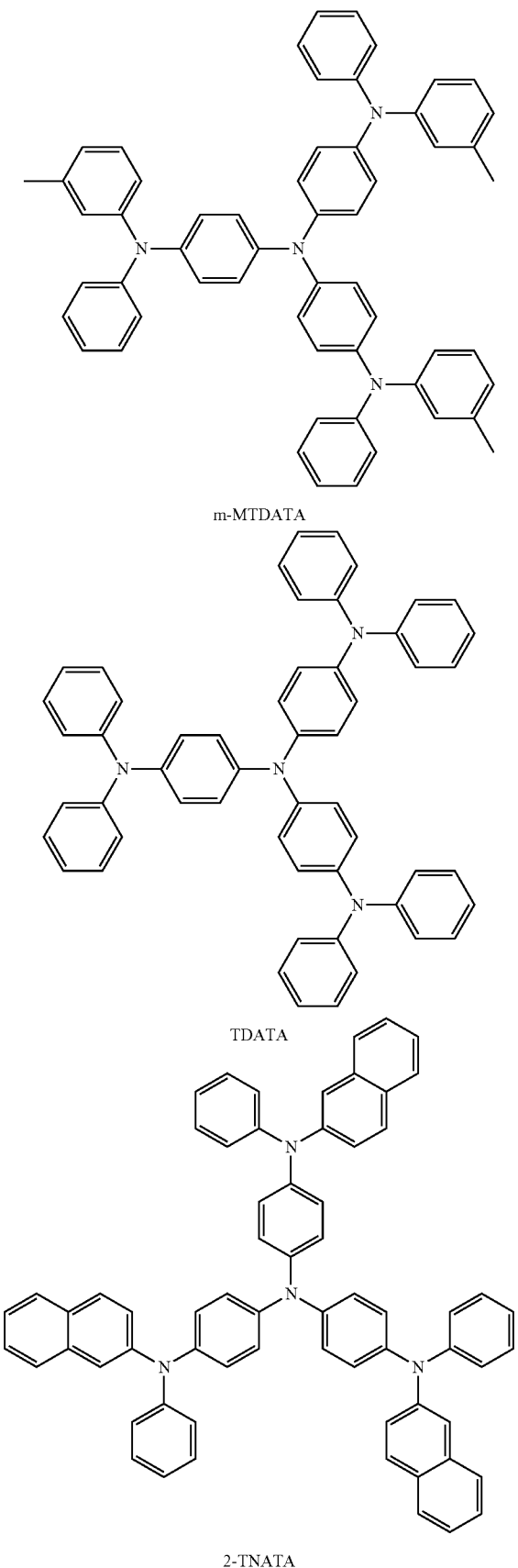

m-MTDATA

TDATA

2-TNATA

The thickness of the HIL may be about 100 Å to about 10000 Å, and in some embodiments, may be from about 100 Å to about 1000 Å. When the thickness of the HIL is within these ranges, the HIL may have good hole injecting ability without a substantial increase in driving voltage.

Then, a HTL may be formed on the HIL by using vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary according to the material that is used to form the HTL.

The HTL may comprise any known hole-transporting materials. Non-limiting examples of suitable known HTL forming materials are carbazole derivatives, such as N-phenylcarbazole or polyvinylcarbazole, N,N-bis(3-methylphenyl)-N,N-diphenyl-[1,1-biphenyl]-4,4'-diamine (TPD), 4,4', 4''-tris(N-carbazolyl)triphenylamine (TCTA), and N,N'-di (1-naphthyl)-N,N'-diphenylbenzidine) (NPB).

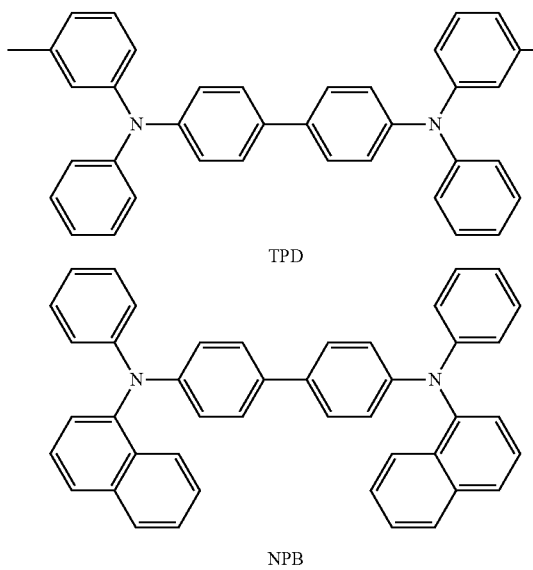

The thickness of the HTL may be from about 50 Å to about 2000 Å, and in some embodiments, may be from about 100 Å to about 1500 Å. When the thickness of the HTL is within these ranges, the HTL may have good hole transporting ability without a substantial increase in driving voltage.

The H-functional layer (having both hole injection and hole transport capabilities) may contain at least one material from each group of the hole injection layer materials and hole transport layer materials. The thickness of the H-functional layer may be from about 500 Å to about 10,000 Å, and in some embodiments, may be from about 100 Å to about 1,000 Å. When the thickness of the H-functional layer is within these ranges, the H-functional layer may have good hole injection and transport capabilities without a substantial increase in driving voltage.

In some embodiments, at least one of the HIL, HTL, and H-functional layer may include at least one of a compound of Formula 300 below and a compound of Formula 350 below:

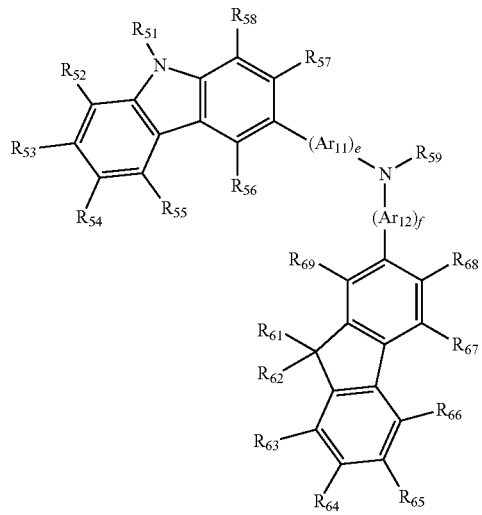

<Formula 300>

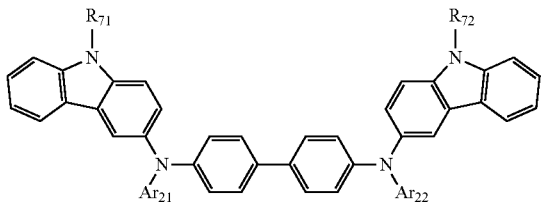

<Formula 350>

$Ar_{11}$, $Ar_{12}$, $Ar_{21}$, and $Ar_{22}$ in Formula 300 and 350 are each independently a substituted or unsubstituted $C_5$-$C_{60}$ arylene group.

In Formula 300, e and f may be each independently an integer from 0 to 5, for example, may be 0, 1, or 2. In a non-limiting embodiment, e may be 1, and f may be 0.

In Formulae 300 and 350 above, $R_{51}$ to $R_{58}$, $R_{61}$ to $R_{69}$, and $R_{71}$ and $R_{72}$ may be each independently a hydrogen atom, a deuterium atom, a halogen atom, a hydroxyl group, a cyano group, a nitro group, an amino group, an amidino group, a hydrazine group, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. In some embodiments, $R_{51}$ to $R_{58}$, $R_{61}$ to $R_{69}$, $R_{71}$, and $R_{72}$ may be each independently one of a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{59}$ may be one of a phenyl group, a naphthyl group, an anthryl group, a biphenyl group, a pyridyl group; and a phenyl group, a naphthyl group, an anthryl group, a biphenyl group, and a pyridyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In an embodiment the compound of Formula 300 may be a compound represented by Formula 300 Å below:

<Formula 300A>

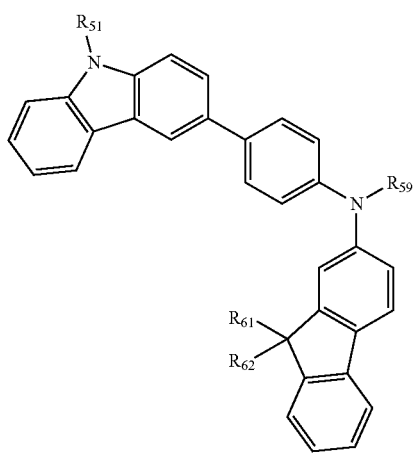

In Formula 300 Å, $R_{51}$, $R_{61}$, $R_{62}$, and $R_{59}$ may be as defined above.

In some non-limiting embodiments, at least one of the HIL, HTL, and H-functional layer may include at least one of compounds represented by Formulae 301 to 320 below.

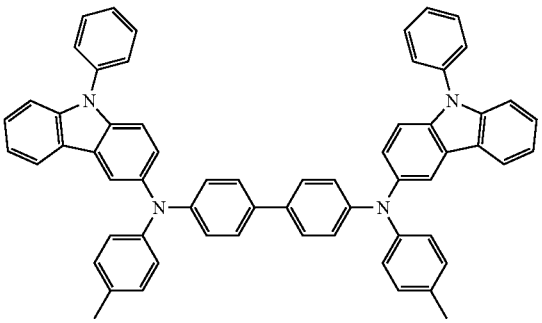
302

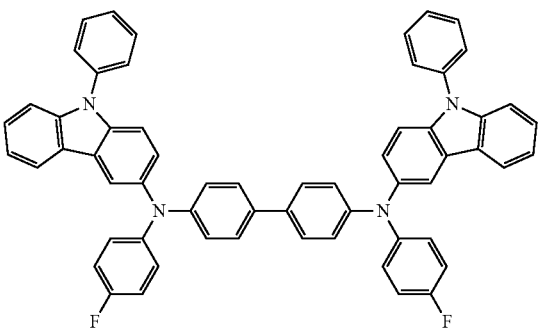
303

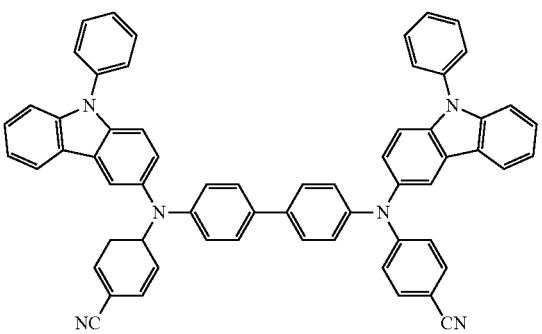
304

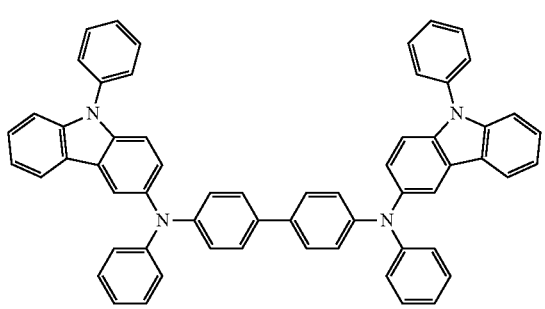
301

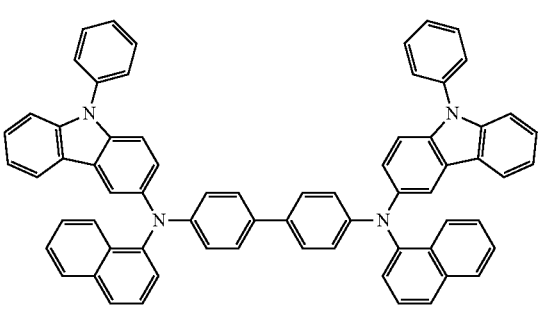
305

306
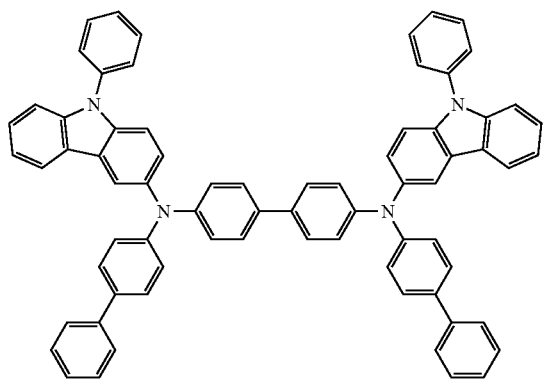
307
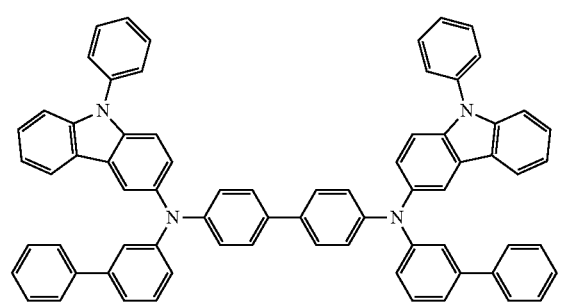
308
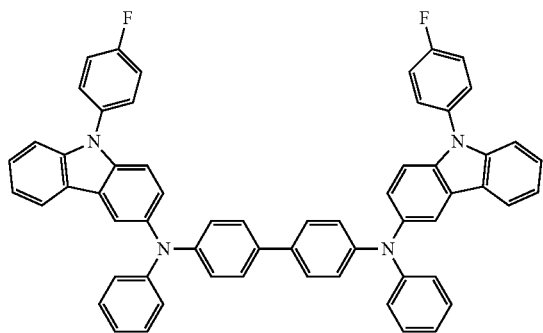
309
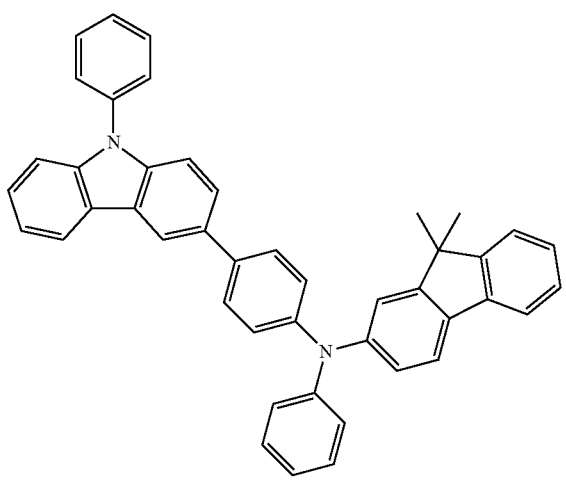
310
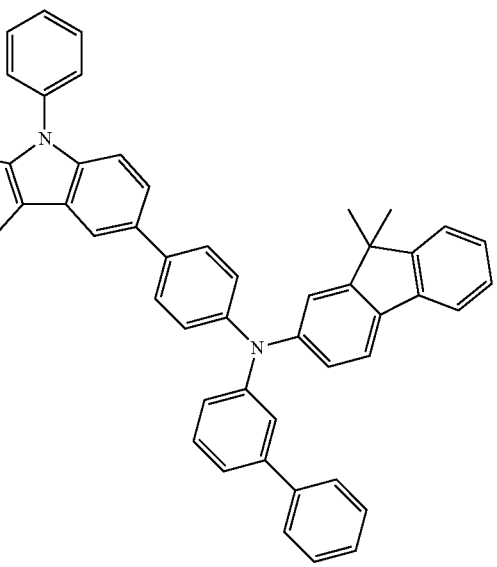
311
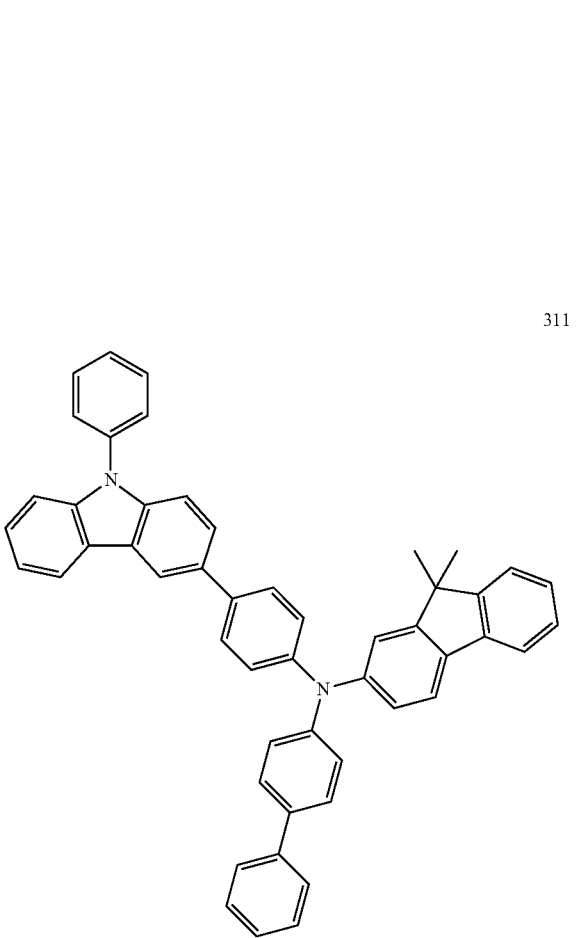

312
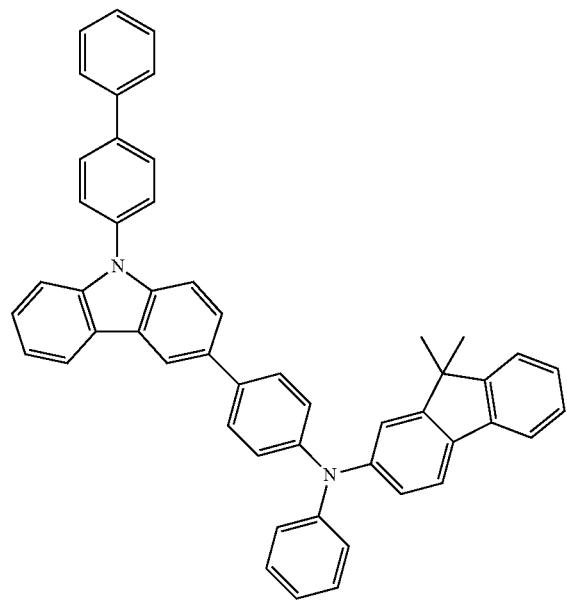
313
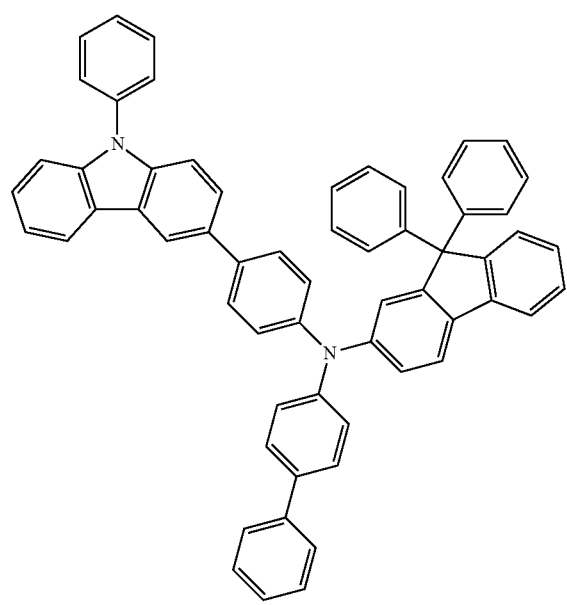
314
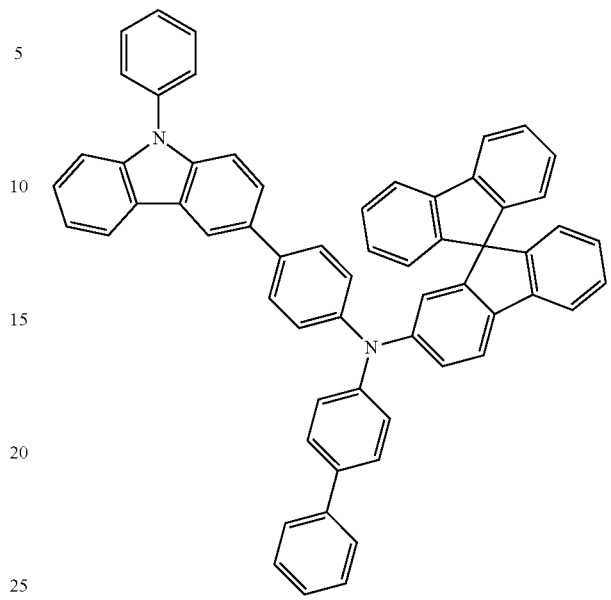
315
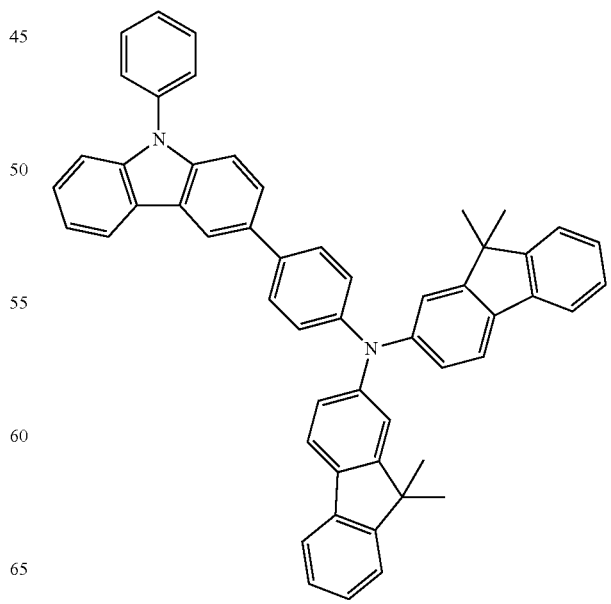

316

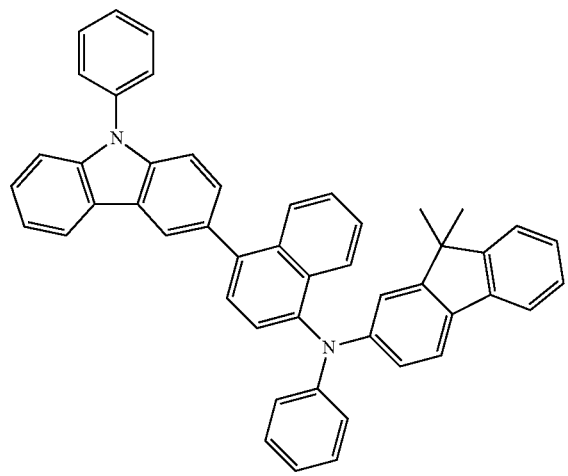

317

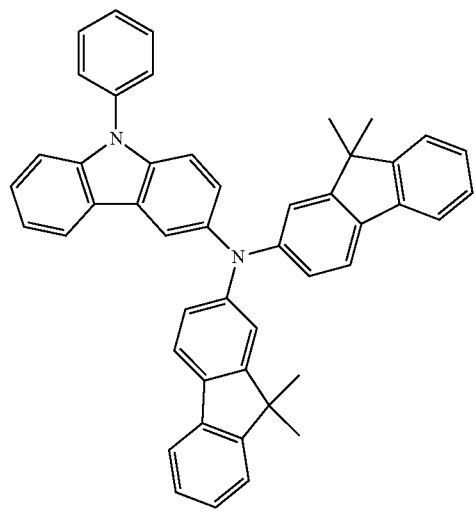

318

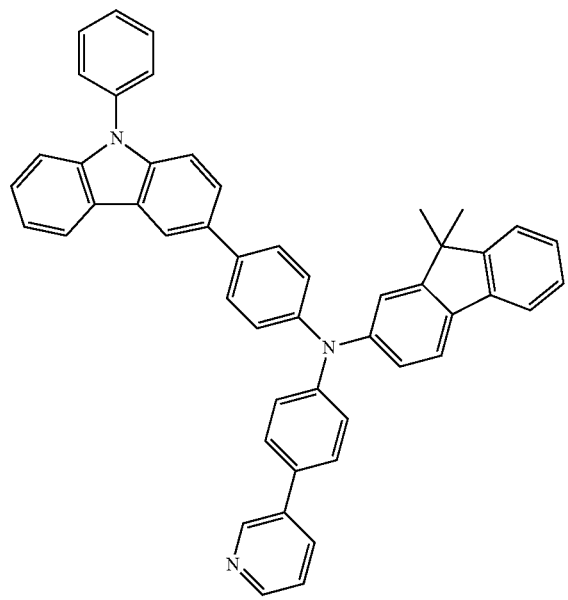

319

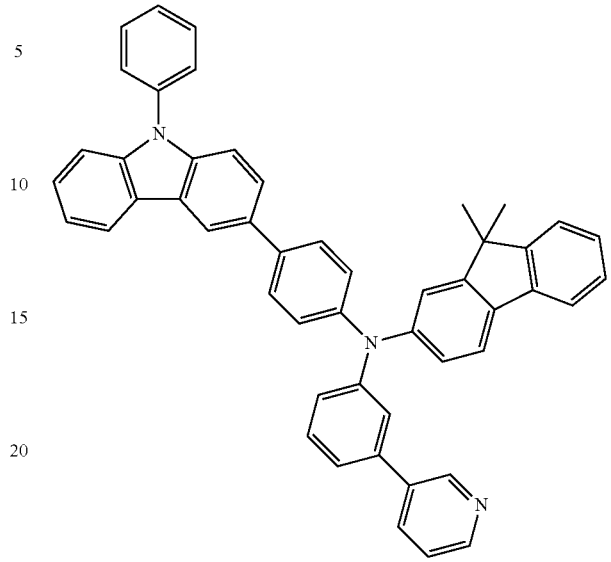

320

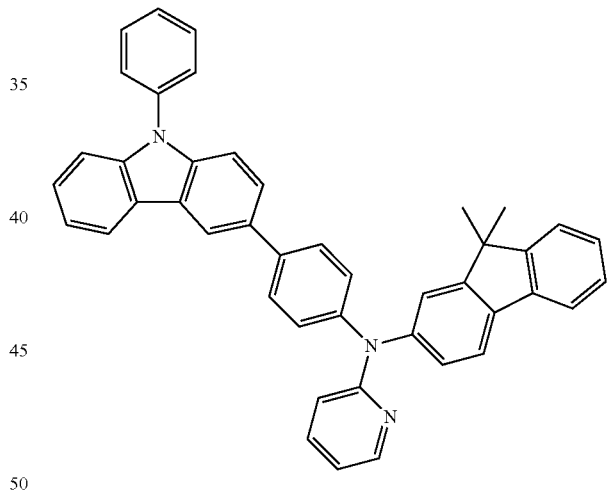

At least one of the HIL, HTL, and H-functional layer may further include a charge-generating material for improved layer conductivity, in addition to a known hole injecting material, hole transport material, and/or material having both hole injection and hole transport capabilities as described above.

The charge-generating material may be, for example, a p-dopant. The p-dopant may be one of quinine derivatives, metal oxides, or compounds having a cyano group, but are not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

<Compound 200>

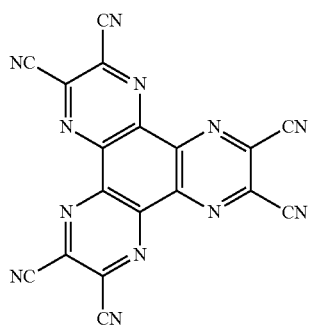

<F4-TCNQ>

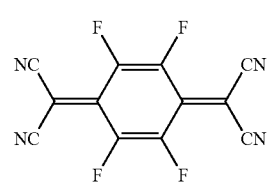

When the hole injection layer, hole transport layer, or H-functional layer further includes a charge-generating material, the charge-generating material may be homogeneously dispersed or inhomogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The buffer layer may include any hole injecting material or hole transporting material that are widely known. In some other embodiments, the buffer layer may include the same material as one of the materials included in the HIL, HTL, and H-functional layer that underly the buffer layer.

Then, an EML may be formed on the HTL, H-functional layer, or buffer layer by vacuum deposition, spin coating, casting, Langmuir-Blodget (LB) deposition, or the like. When the EML is formed using vacuum deposition or spin coating, the deposition and coating conditions may be similar to those for the formation of the HIL, though the conditions for deposition and coating may vary according to the material that is used to form the EML.

The EML may be formed using any of various known hosts and dopants. Dopants that may be used to form the EML may include either a fluorescent dopant or a phosphorescent dopant which are widely known in the art.

Non-limiting examples of the known host are $Alq_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, distyrylarylene (DSA), dmCBP (see a formula below), and Compounds 501 to 509 below.

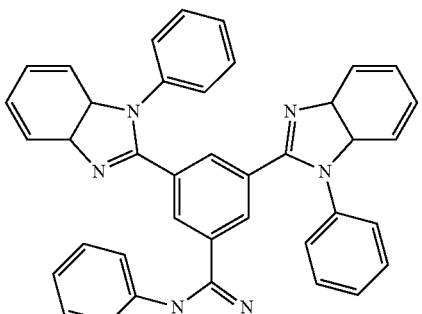

TPBI

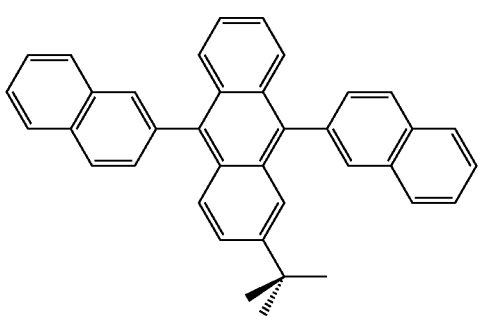

TBADN

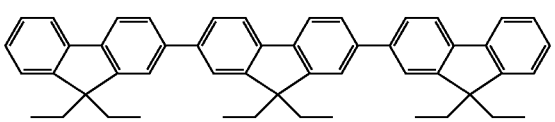

E3

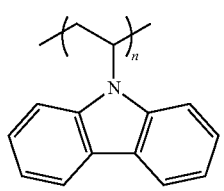

PVK

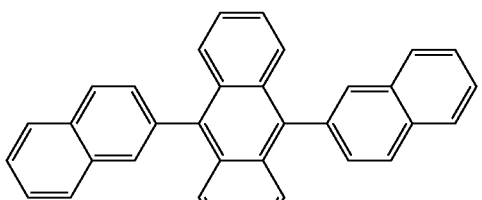

ADN

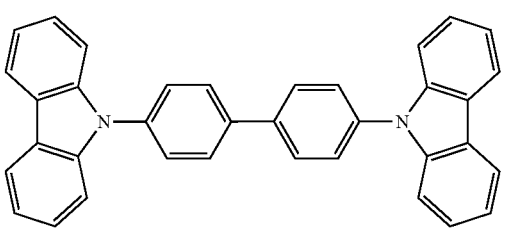

CBP

41
-continued
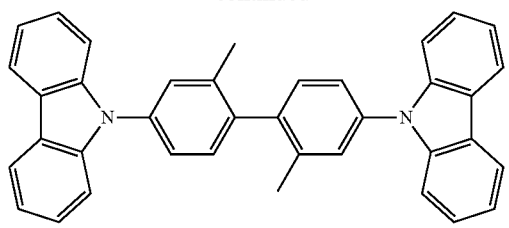
dmCBP
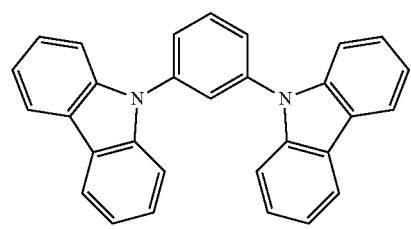
501
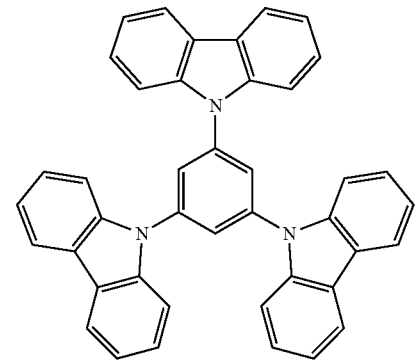
502
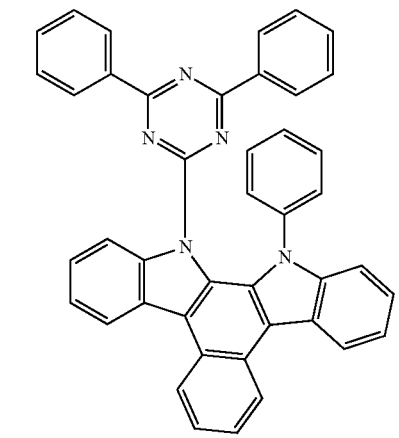
503
42
-continued
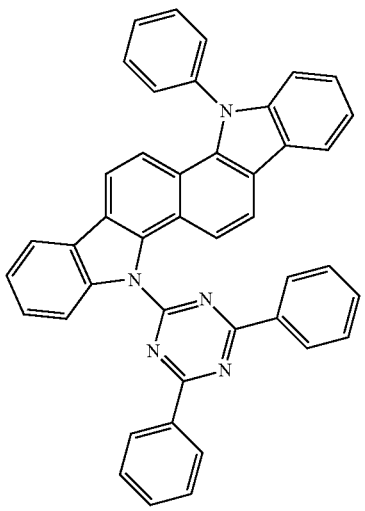
504
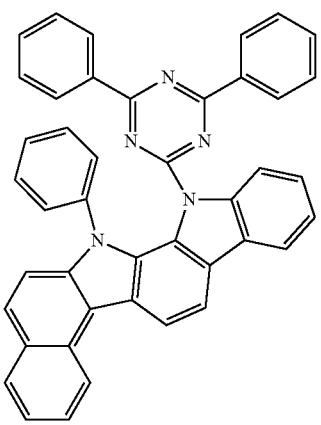
505
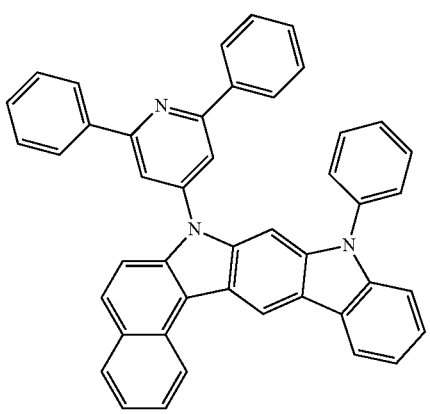
506

-continued

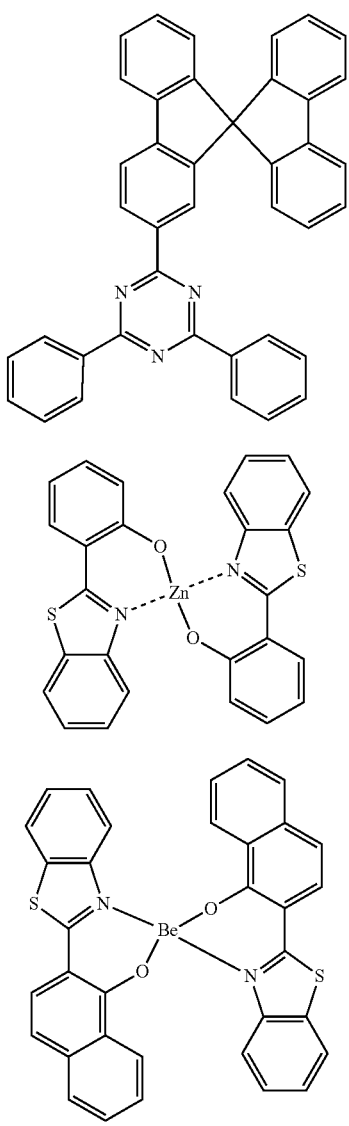

In some embodiments, an anthracene-based compound represented by Formula 400 below may be used as the host.

<Formula 400>

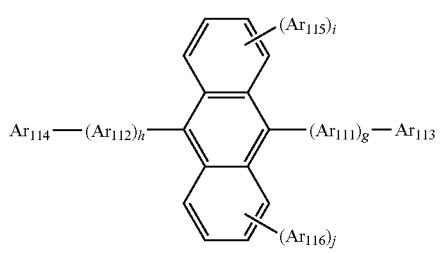

In Formula 400, $Ar_{111}$ and $Ar_{112}$ are each independently a substituted or unsubstituted $C_5$-$C_{60}$ arylene group; $Ar_{113}$ to $Ar_{116}$ are each independently a substituted or unsubstituted $C_1$-$C_{10}$ alkyl group or a substituted or unsubstituted $C_5$-$C_{60}$ aryl group; and g, h, I, and j are each independently an integer from 0 to 4.

In some embodiments, $Ar_{111}$ and $Ar_{112}$ in Formula 400 may be each independently a phenylene group, a naphthylene group, a phenanthrenylene group, or a pyrenylene group; or a phenylene group, a naphthylene group, a phenanthrenylene group, a fluorenyl group, or a pyrenylene group that are substituted with at least one of a phenyl group, a naphthyl group, and an anthryl group.

In Formula 400 above, g, h, I, and j may be each independently 0, 1, or 2.

In some non-limiting embodiments, $Ar_{113}$ to $Ar_{116}$ in Formula 400 may be each independently one of a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; and

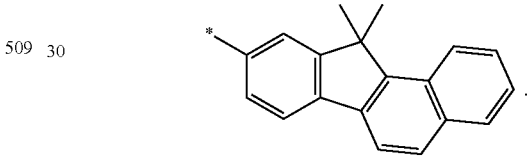

For example, the anthracene compound of Formula 400 above may be one of the compounds represented by the following formulae, but is not limited thereto:

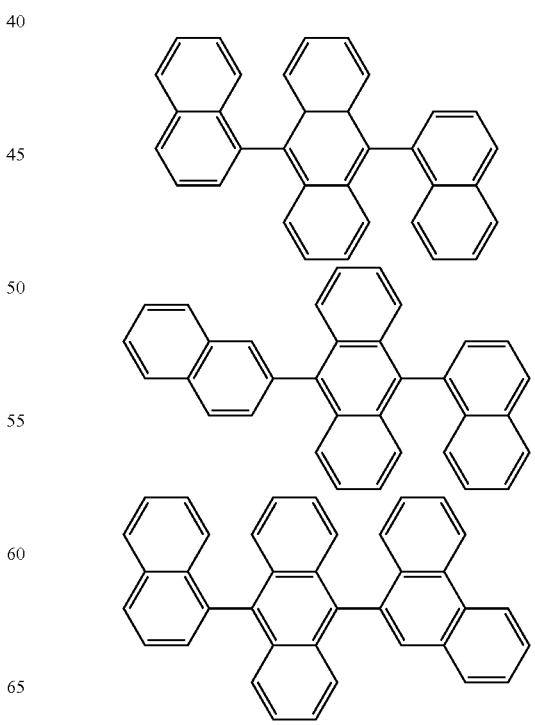

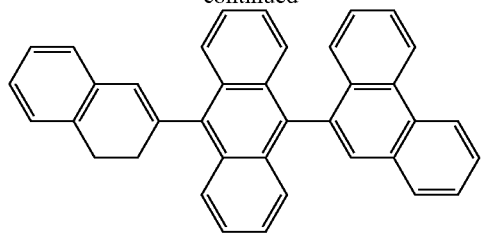
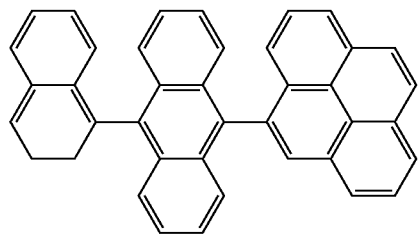
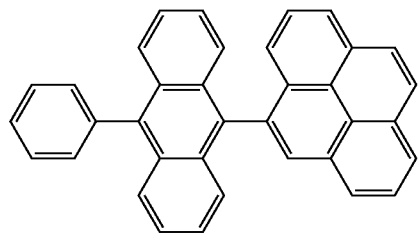
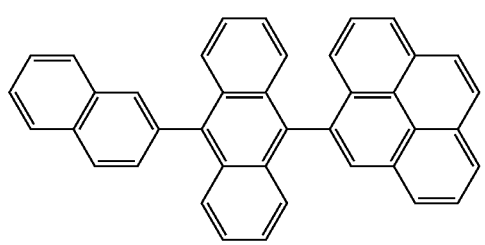
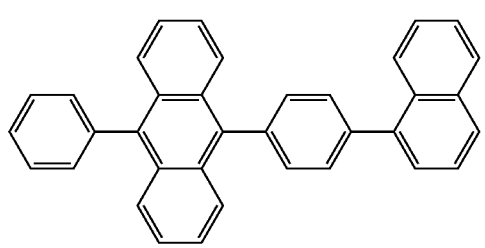
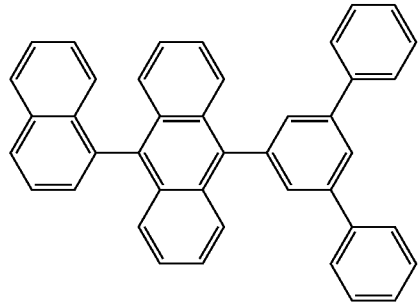
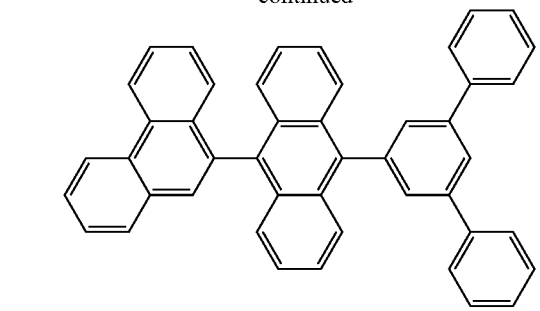
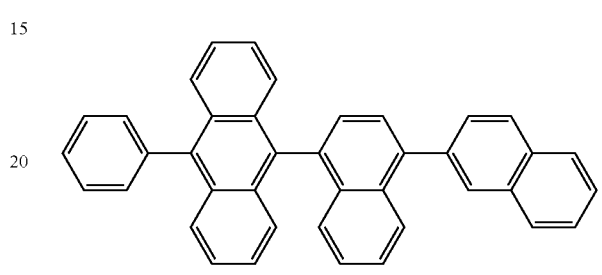
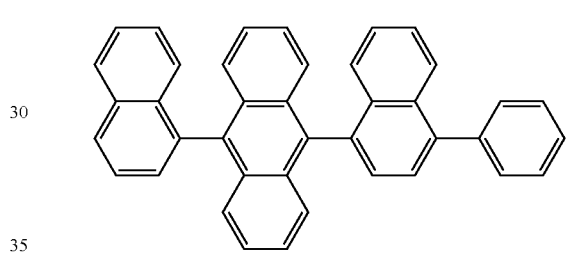
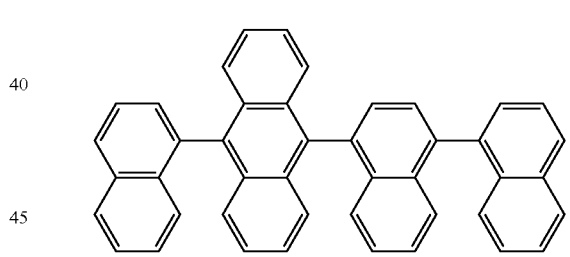
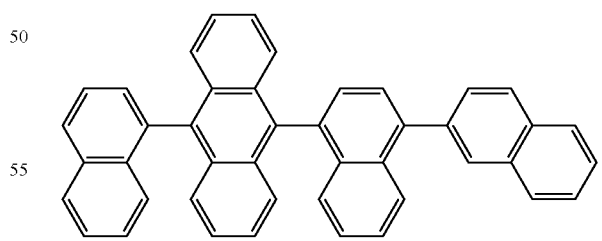
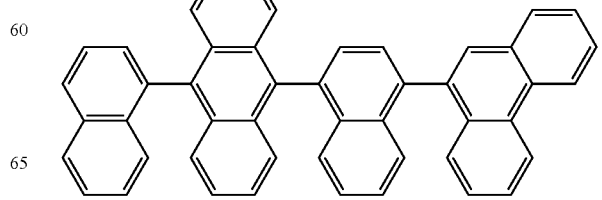

-continued
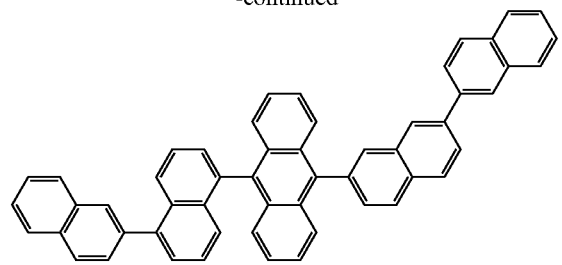
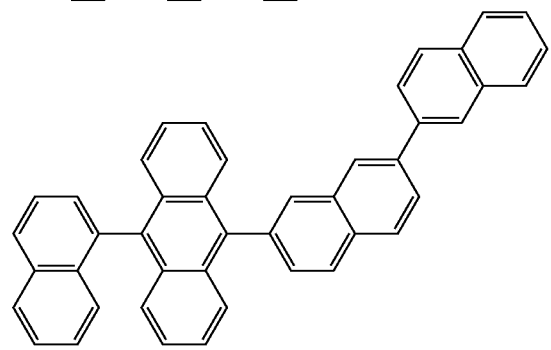
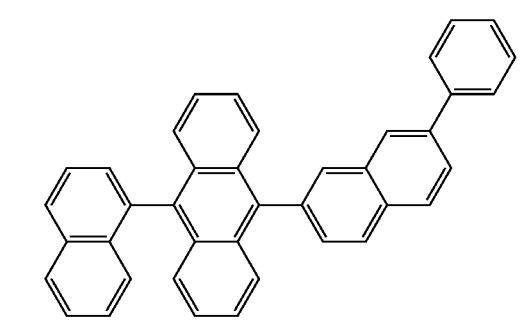
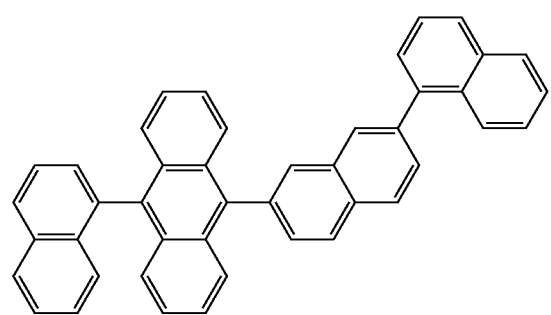
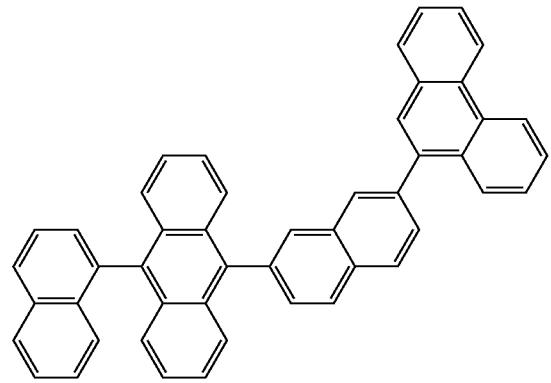
-continued
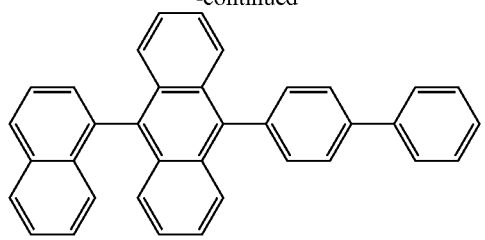
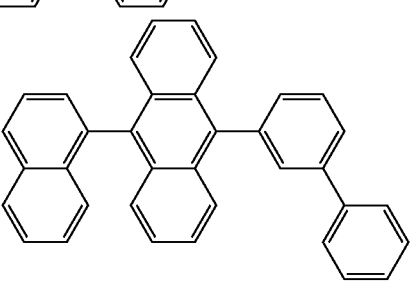
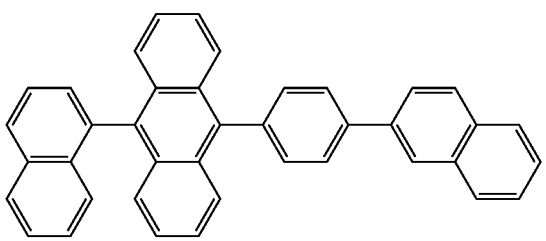
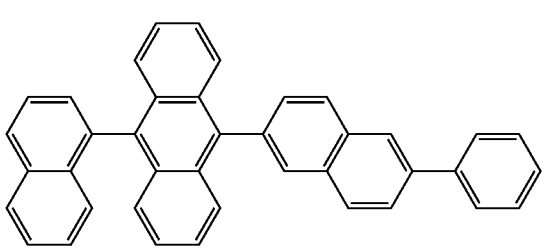
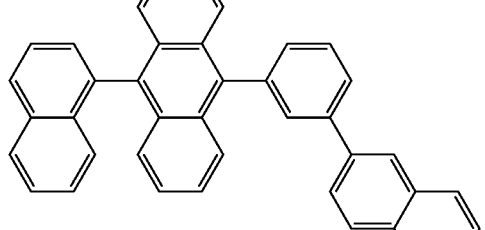
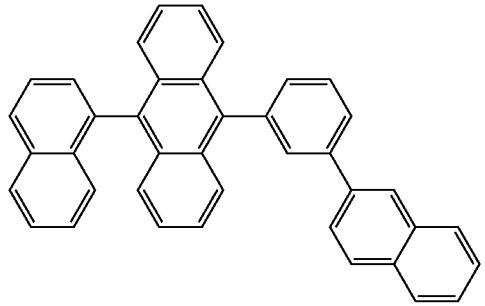

-continued
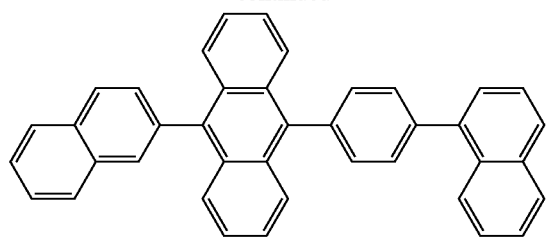
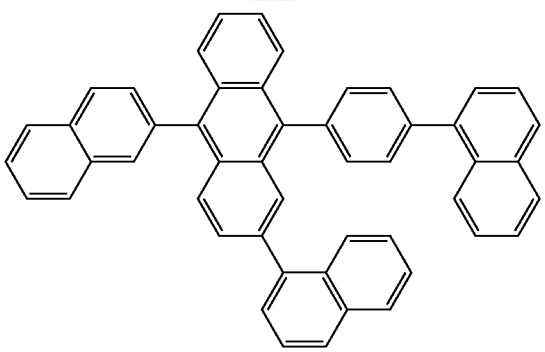
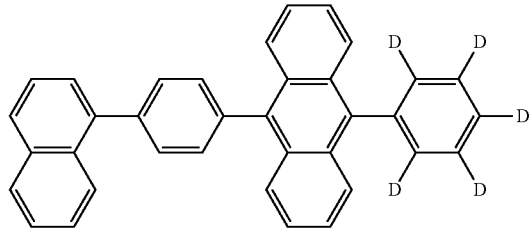
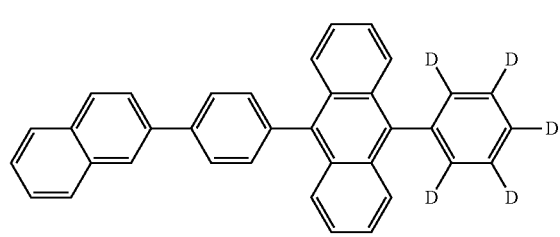
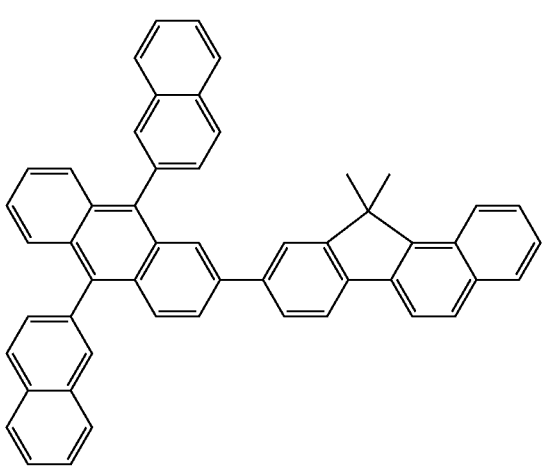
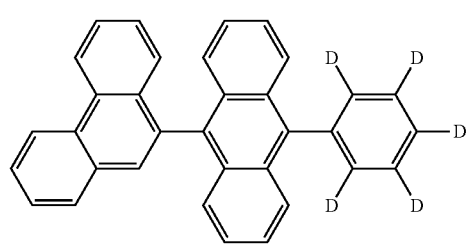
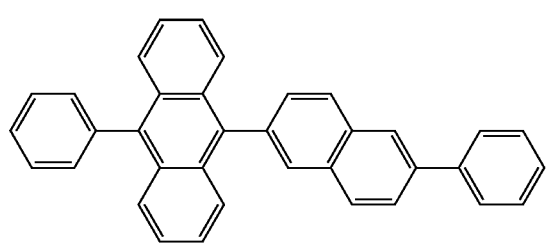
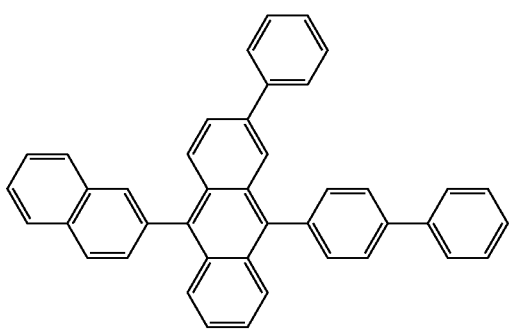
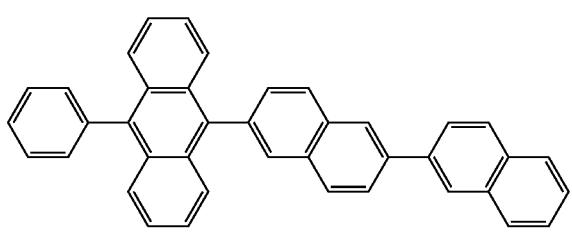

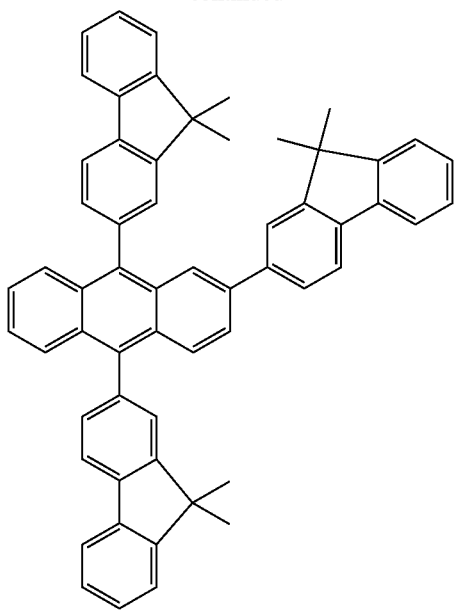

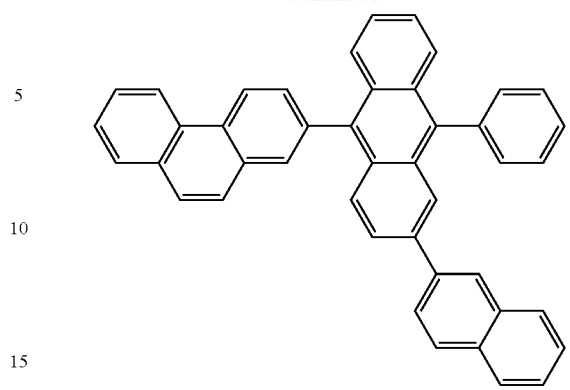

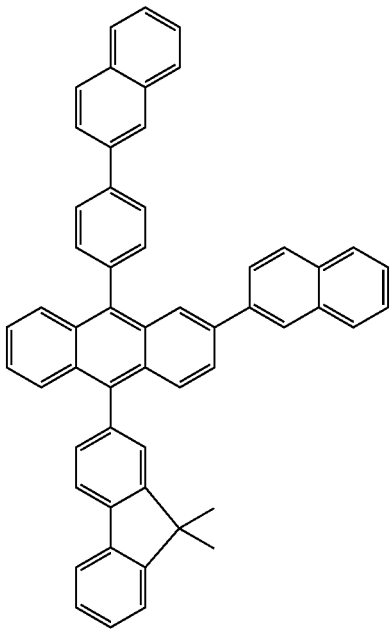

In some embodiments, an anthracene-based compound represented by Formula 401 below may be used as the host.

<Formula 401>

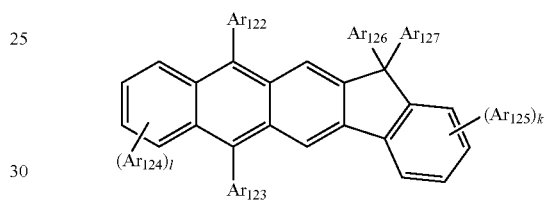

$Ar_{122}$ to $Ar_{125}$ in Formula 401 above may be defined as described above in conjunction with $Ar_{113}$ of Formula 400, and thus detailed descriptions thereof will not be provided here.

$Ar_{126}$ and $Ar_{127}$ in Formula 401 above may be each independently a $C_1$-$C_{10}$ alkyl group, for example, a methyl group, an ethyl group, or a propyl group.

In Formula 401, k and l may be each independently an integer from 0 to 4, for example, 0, 1, or 2.

For example, the anthracene compound of Formula 401 above may be one of the compounds represented by the following formulae, but is not limited thereto:

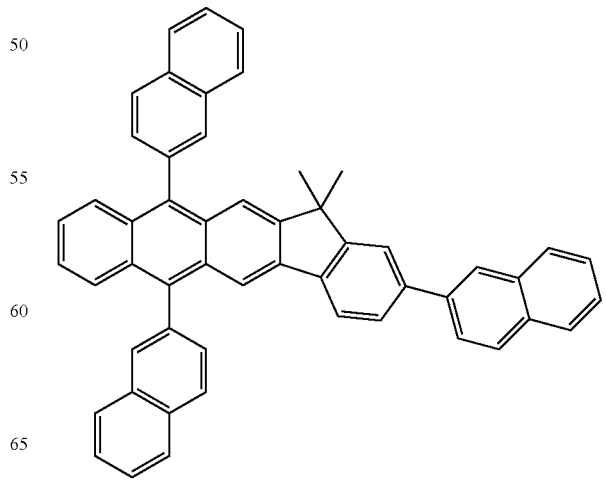

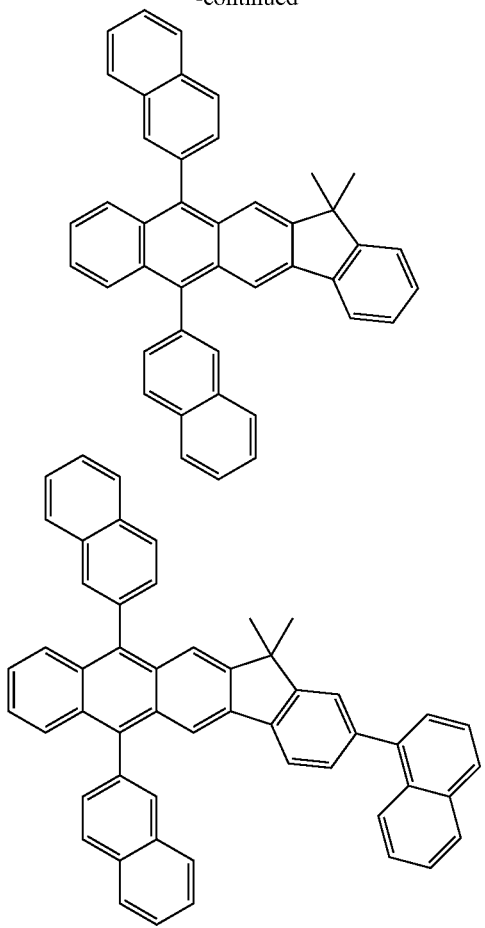

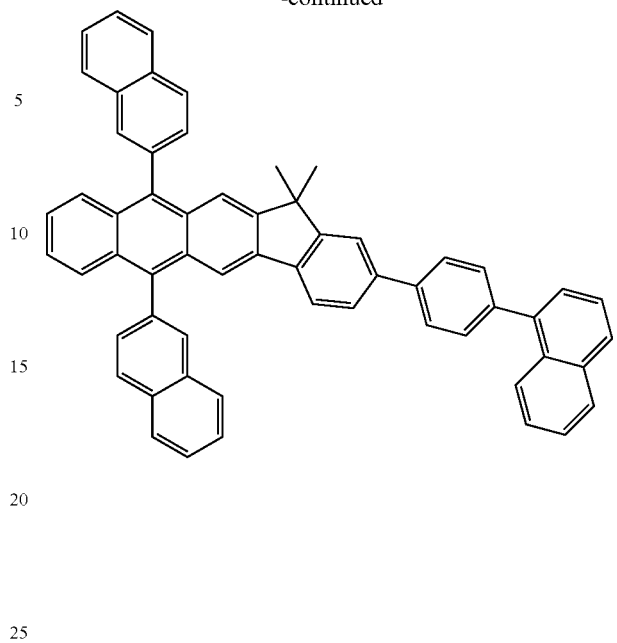

When the organic light-emitting device is a full color organic light-emitting device, the emission layer may be patterned into a red emission layer, a green emission layer, and a blue emission layer.

At least one of the red EML, the green EML, and the blue EML may include a dopant below (ppy=phenylpyridine).

Non-limiting examples of the blue dopant are compounds represented by the following formulae.

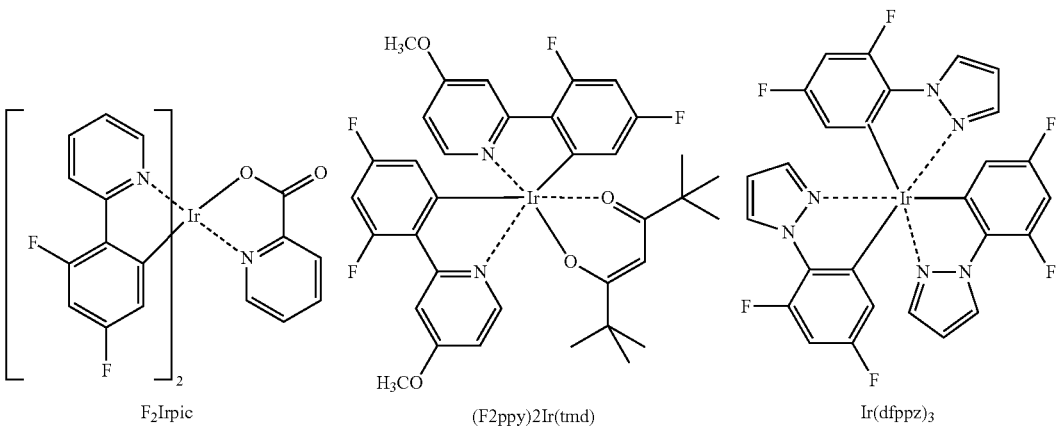

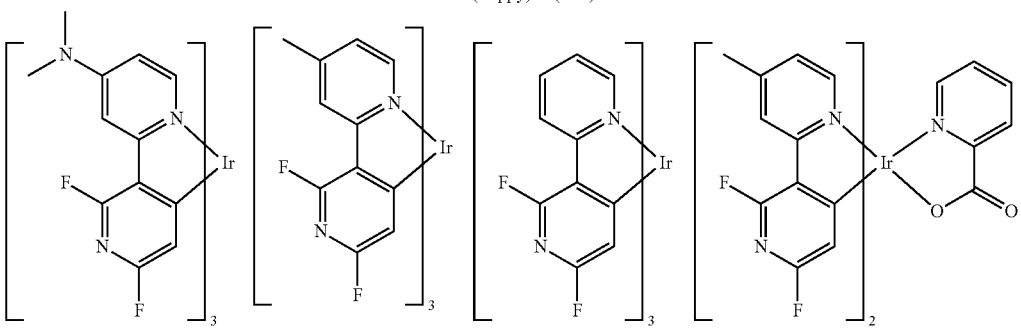

-continued
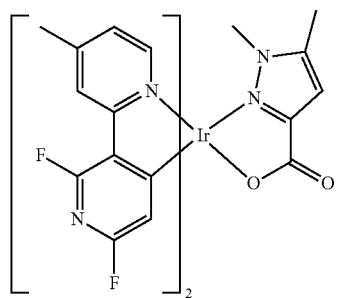
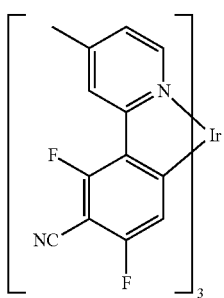
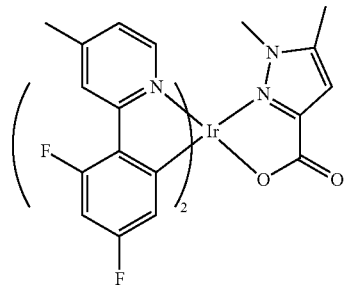
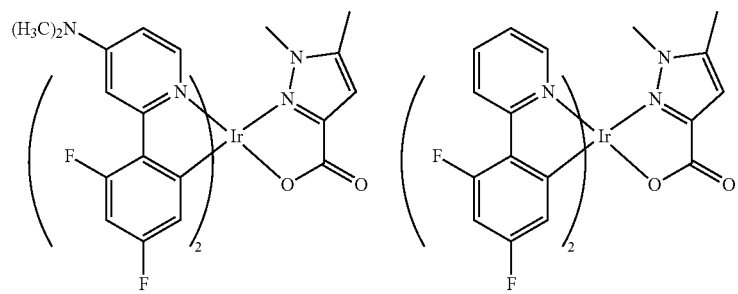
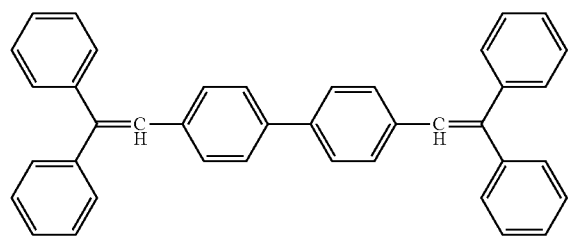
DPVBi
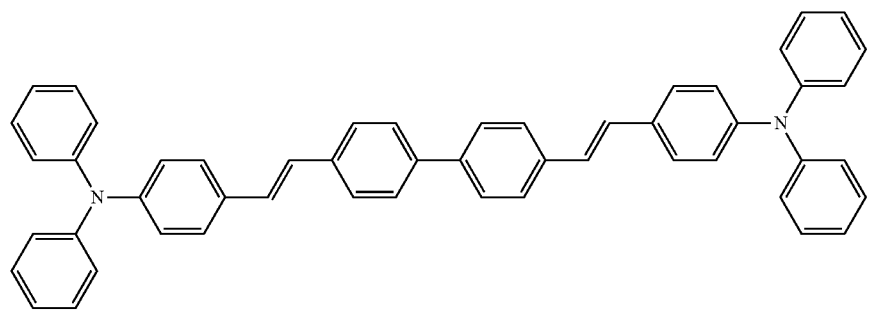
DPAVBi
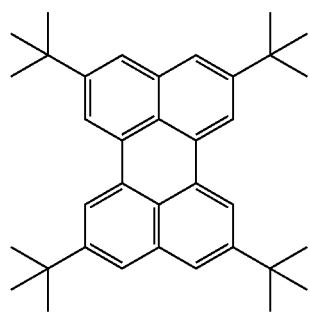
TBPe Non-limiting examples of the red dopant are compounds represented by the following formulae.
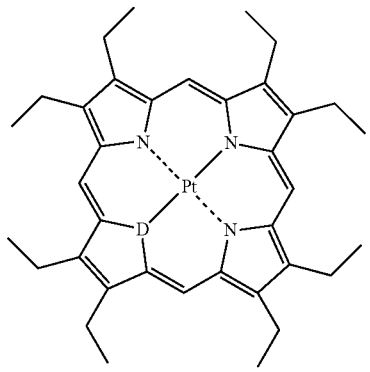
PtOEP
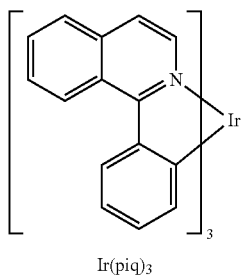
Ir(piq)₃
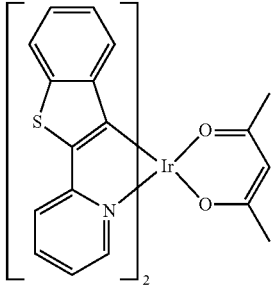
Btp₂Ir(acac)
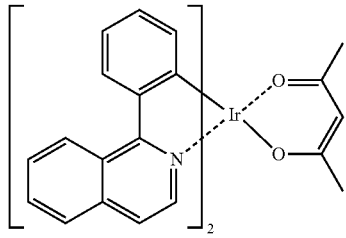
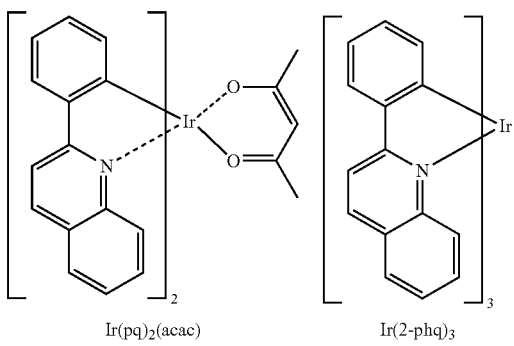
Ir(pq)₂(acac)　　　Ir(2-phq)₃
-continued
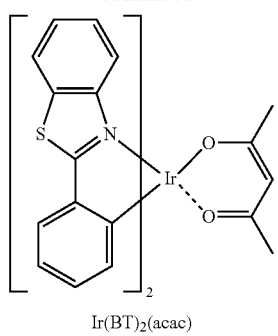
Ir(BT)₂(acac)
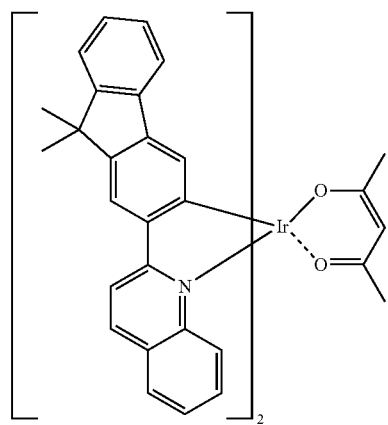
Ir(flq)₂(acac)
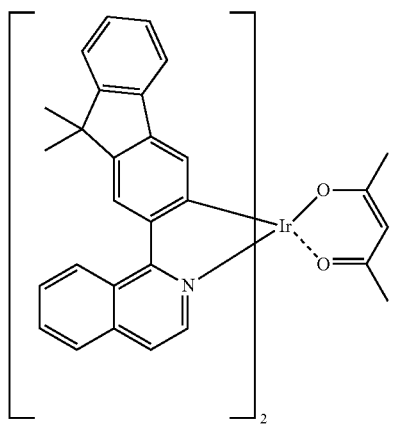
Ir(fliq)₂(acac)
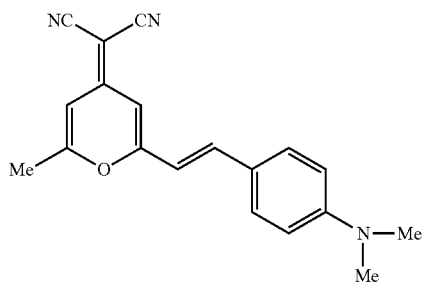
DCM -continued
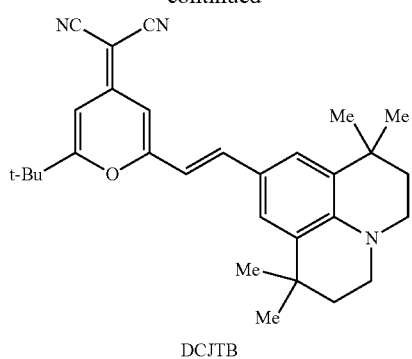
DCJTB
Non-limiting examples of the green dopant are compounds represented by the following formulae.
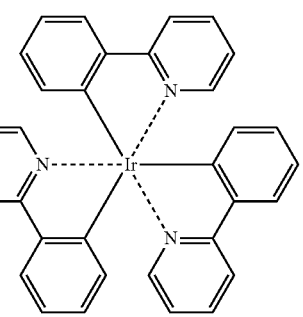
Ir(ppy)₃
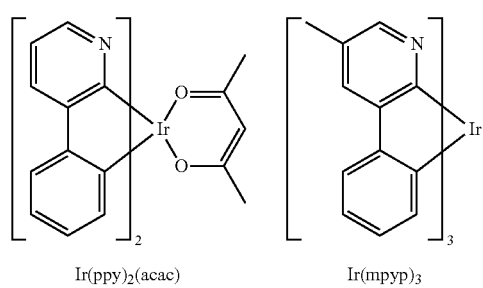
Ir(ppy)₂(acac)   Ir(mpyp)₃
C545T
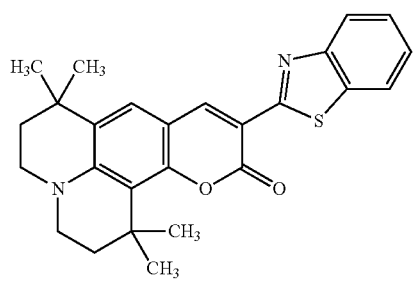
Non-limiting examples of the dopant that may be used in the EML are Pd complexes or Pt complexes represented by the following formulae.
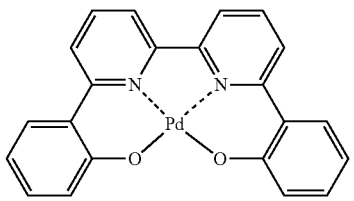
D1
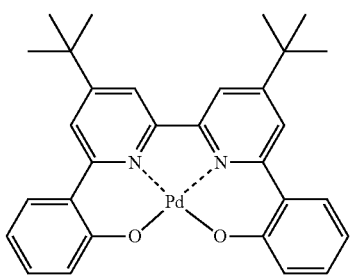
D2
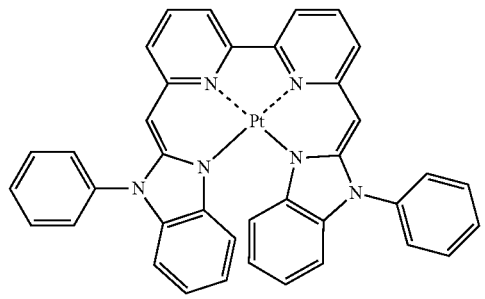
D3
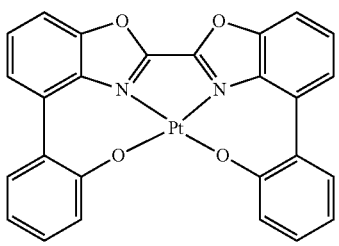
D4
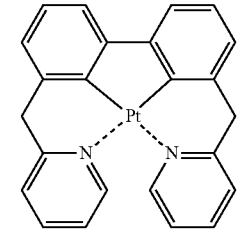
D5
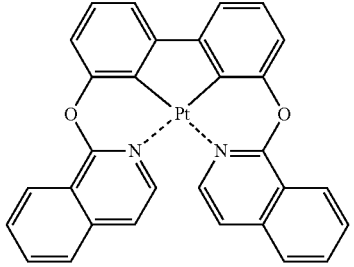
D6

-continued
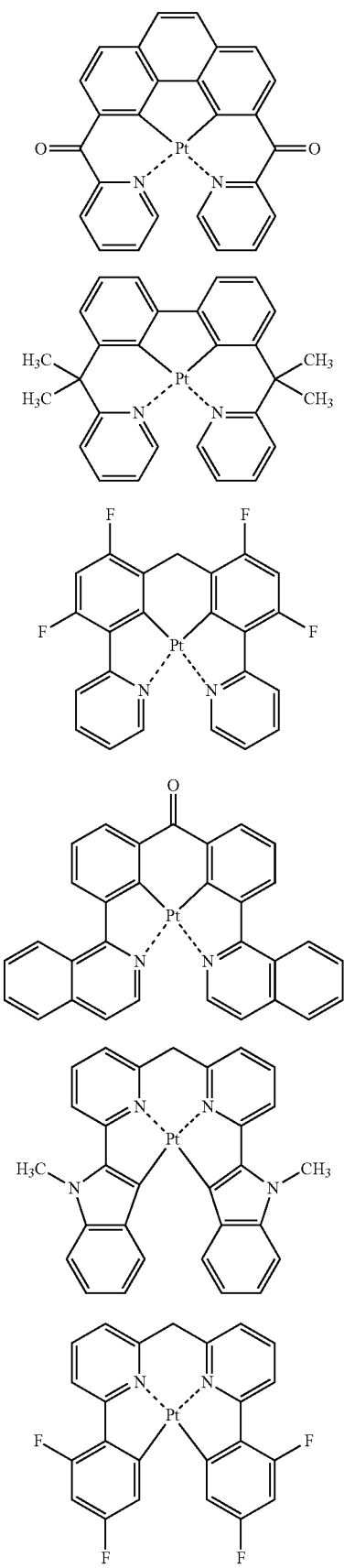
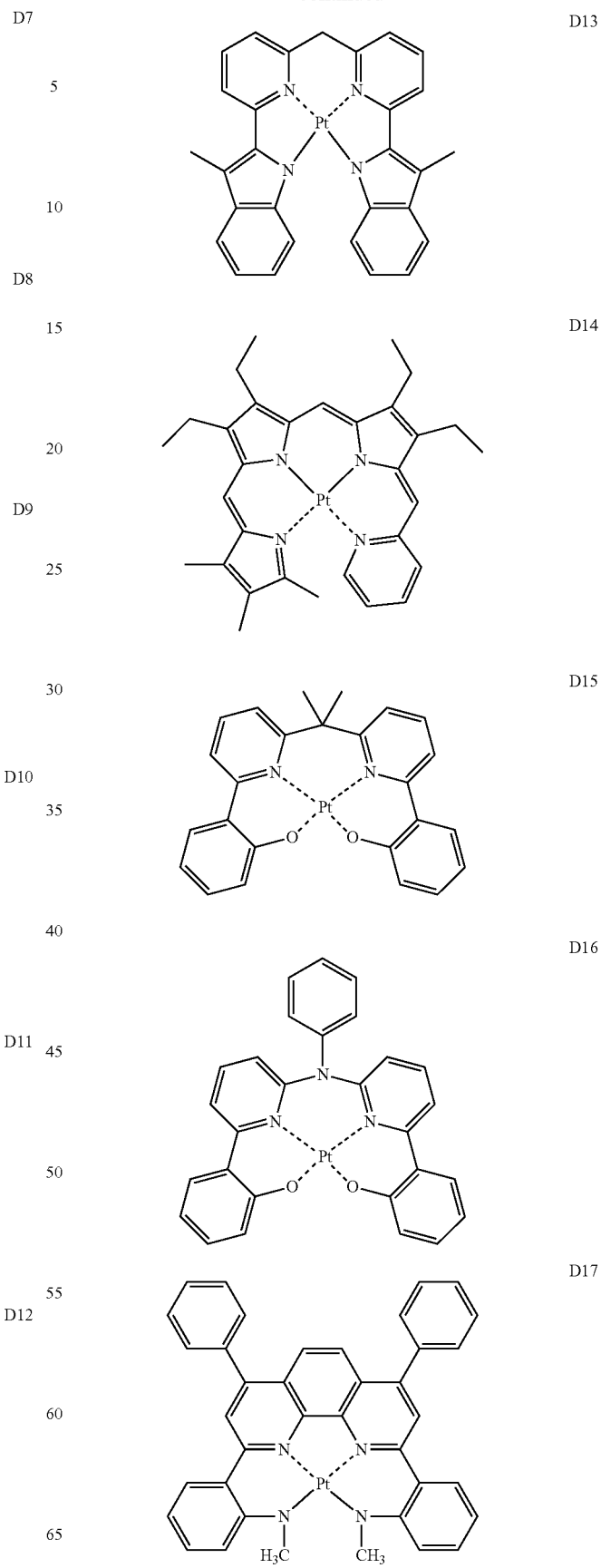

D18 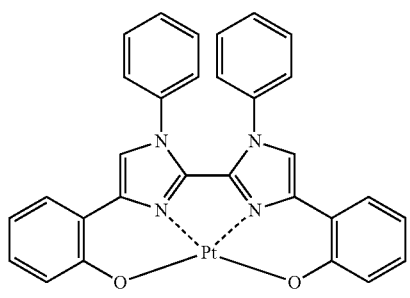
D19 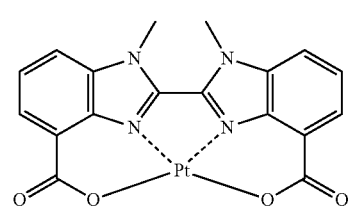
D20 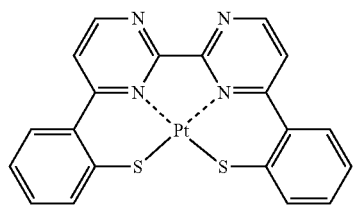
D21 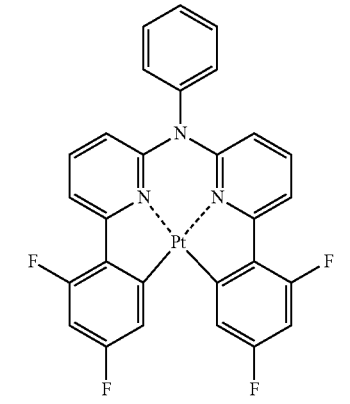
D22 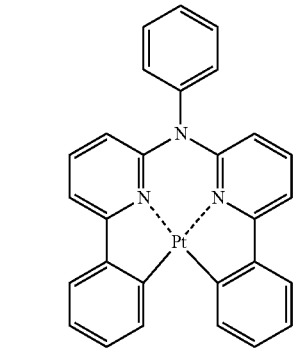
D23 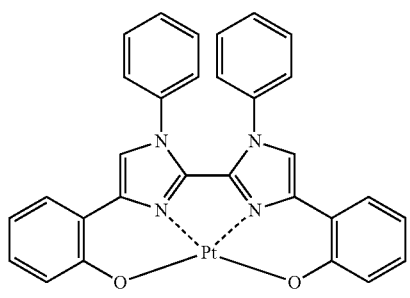
D24 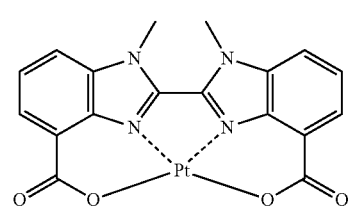
D25 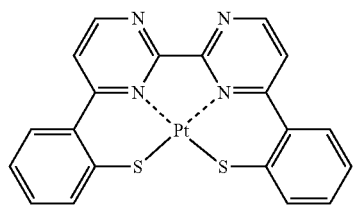
D26 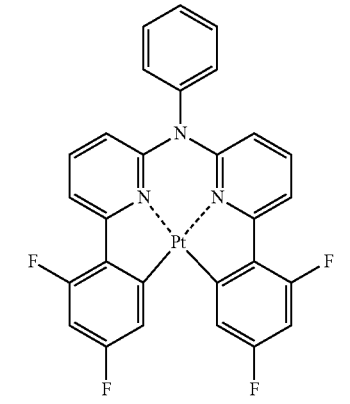
D27 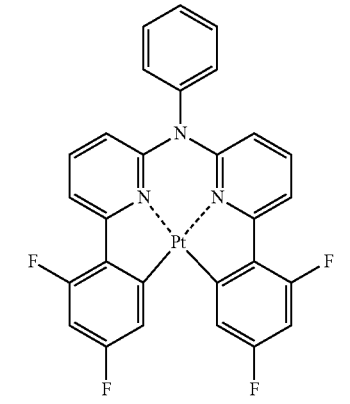
D28 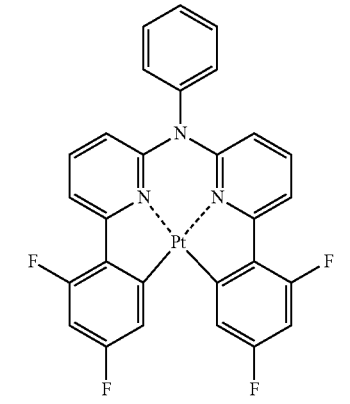

D29 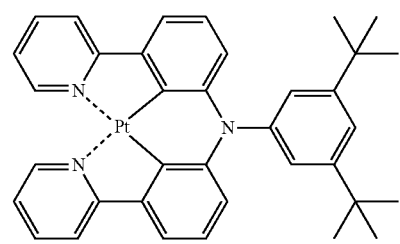
D30 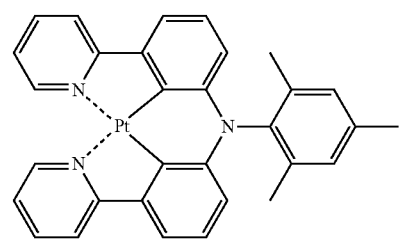
D31 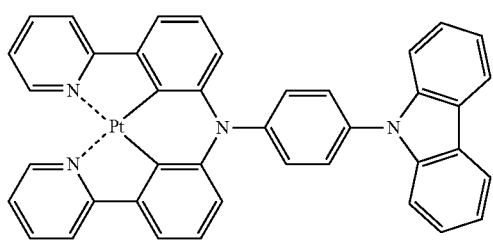
D32 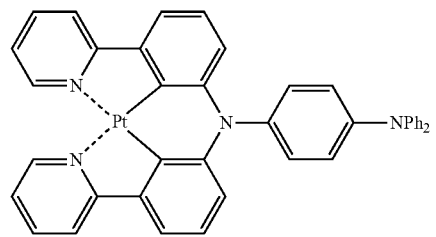
D33 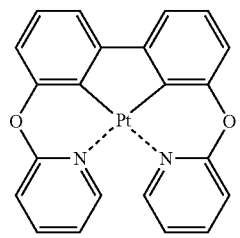
D34 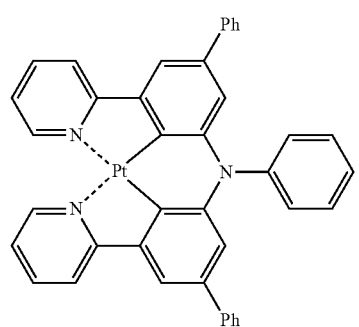
D35 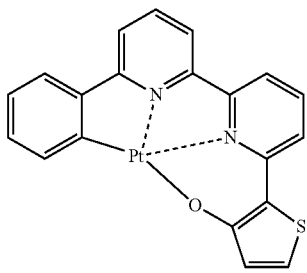
D36 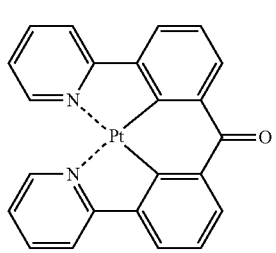
D37 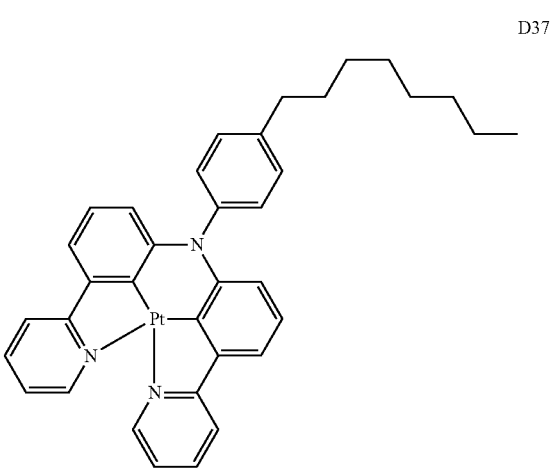
D38 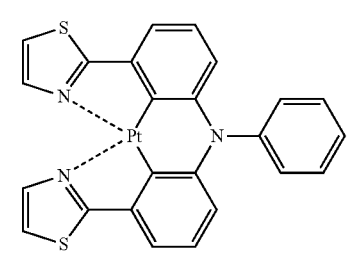
D39 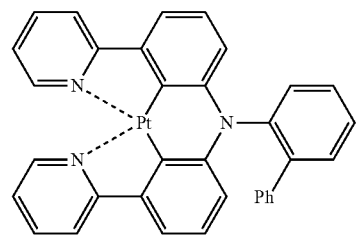

-continued
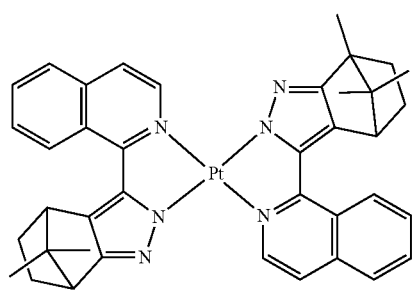 D40
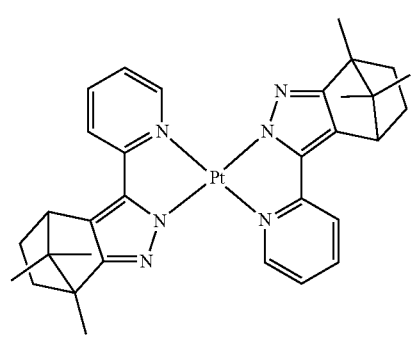 D41
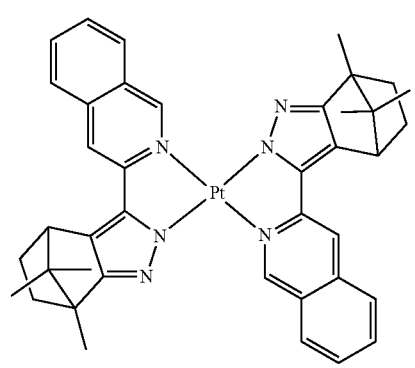 D42
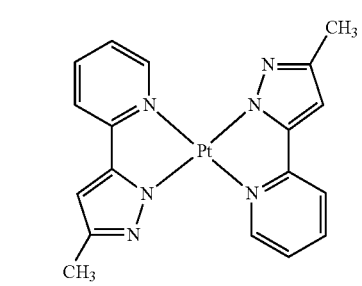 D43
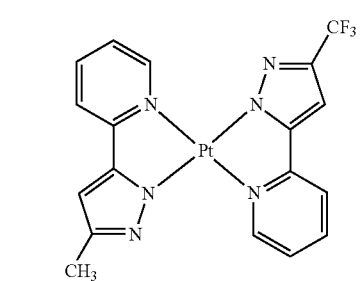 D44
-continued
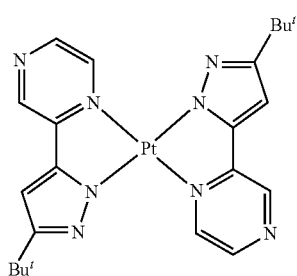 D45
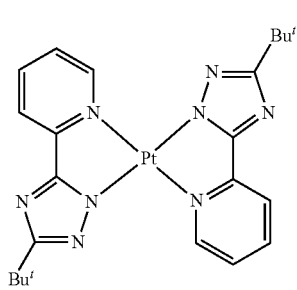 D46
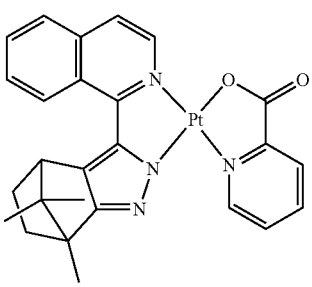 D47
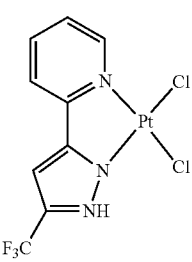 D48
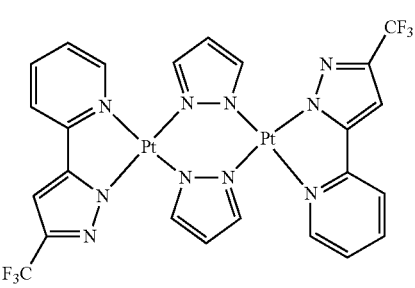 D49

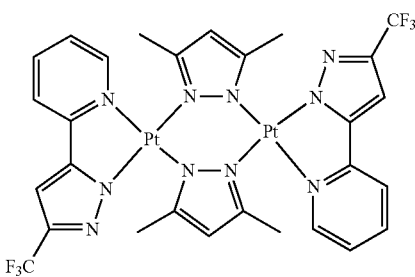

D50

Non-limiting examples of the dopant that may be used in the EML are Os complexes represented by the following formulae.

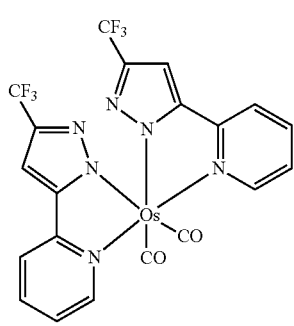

OS(fppz)₂(CO)₂

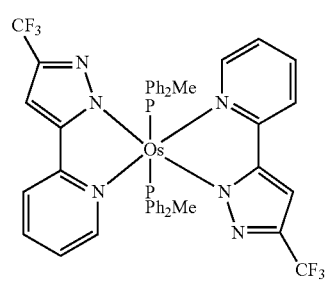

OS(fppz)₂(PPh₂Me)₂

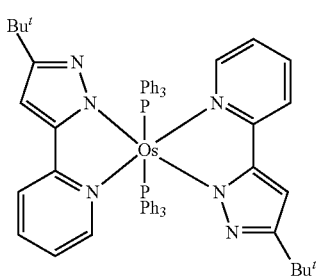

OS(bppz)₂(PPh₂Me)₂

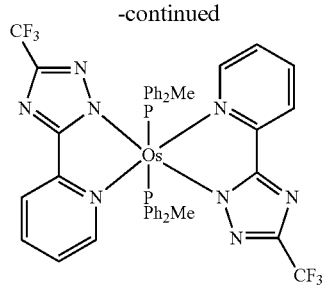

OS(fptz)₂(PPh₂Me)₂

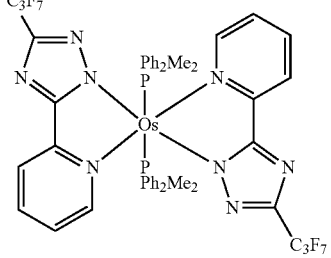

OS(hptz)₂(PPhMe₂)₂

When the EML includes both a host and a dopant, the amount of the dopant may be from about 0.01 to about 15 parts by weight based on 100 parts by weight of the host. However, the amount of the dopant is not limited to this range.

The thickness of the EML may be about 100 Å to about 1000 Å, and in some embodiments, may be from about 200 Å to about 600 Å. When the thickness of the EML is within these ranges, the EML may have good light emitting ability without a substantial increase in driving voltage.

Then, an ETL may be formed on the EML by vacuum deposition, spin coating, casting, or the like. When the ETL is formed using vacuum deposition or spin coating, the deposition and coating conditions may be similar to those for the formation of the HIL, though the deposition and coating conditions may vary according to a compound that is used to form the ETL.

A material for forming the ETL may be the compound of Formula 1 above or any known material that can stably transport electrons injected from an electron injecting electrode (cathode).

Non-limiting examples of materials for forming the ETL are a quinoline derivative, such as tris(8-quinolinorate) aluminum (Alq3), TAZ, BAlq, beryllium bis(benzoquinolin-10-olate) (Bebq₂), 9,10-di(naphthalene-2-yl)anthracene (ADN), Compound 201, and Compound 202.

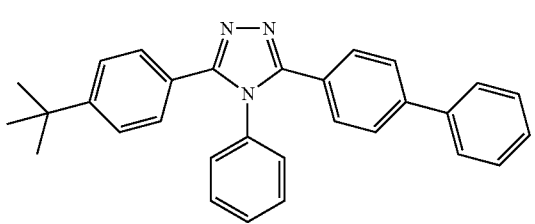

TAZ

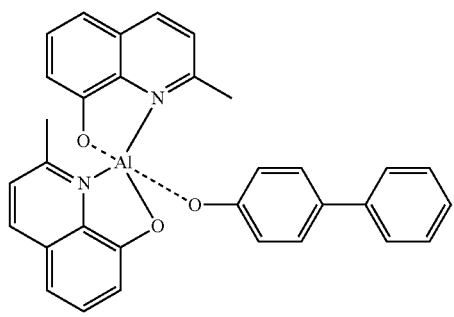

BAlq

<Compound 201>

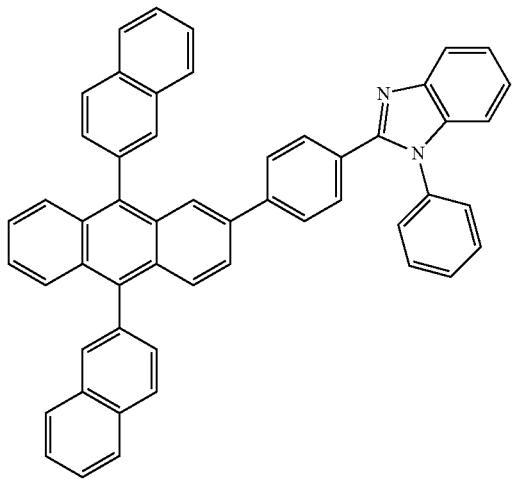

<Compound 202>

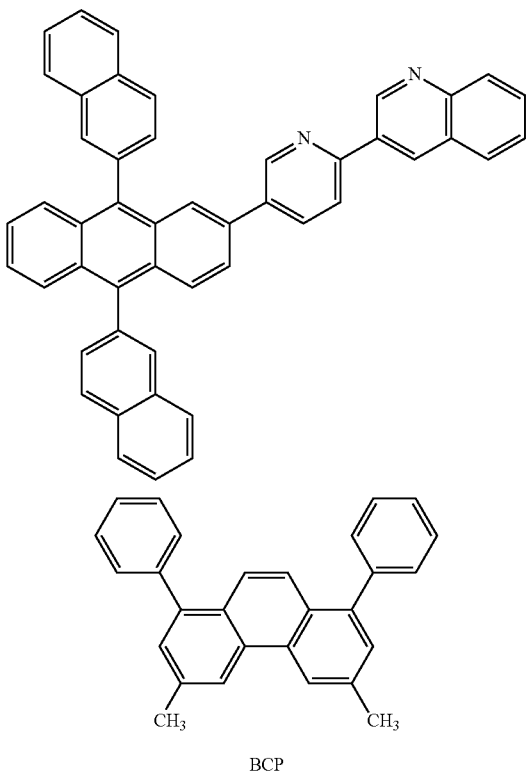

BCP

The thickness of the ETL may be from about 100 Å to about 1,000 Å, and in some embodiments, may be from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to any known electron transport organic compounds.

The metal-containing material may include a lithium (Li) complex. Non-limiting examples of the Li complex are lithium quinolate (LiQ) and Compound 203 below:

<Compound 203>

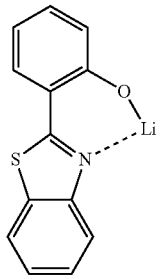

Then, an EIL, which facilitates injection of electrons from the cathode, may be formed on the ETL. Any suitable electron-injecting material may be used to form the EIL.

Non-limiting examples of materials for forming the EIL are LiF, NaCl, CsF, $Li_2O$, and BaO, which are known in the art. The deposition and coating conditions for forming the EIL 18 may be similar to those for the formation of the HIL, though the deposition and coating conditions may vary according to the material that is used to form the EIL 18.

The thickness of the EIL may be from about 1 Å to about 100 Å, and in some embodiments, may be from about 3 Å to about 90 Å. When the thickness of the EIL is within these ranges, the EIL may have satisfactory electron injection ability without a substantial increase in driving voltage.

Finally, the second electrode is disposed on the organic layer. The second electrode 17 may be a cathode that is an electron injection electrode. A material for forming the second electrode 17 may be a metal, an alloy, an electroconductive compound, which have a low work function, or a mixture thereof. In this regard, the second electrode 9 may comprise lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some embodiments, to manufacture a top-emission light-emitting device, the transmission electrode may comprise indium tin oxide (ITO) or indium zinc oxide (IZO).

Although the organic light-emitting device of FIG. 1 is described above, the present embodiments are not limited thereto.

When a phosphorescent dopant is used in the EML, a HBL may be formed between the ETL and the EML or between the E-functional layer and the EML by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Any known hole-blocking material may be used. Non-limiting examples of hole-blocking materials are oxadiazole derivatives, triazole derivatives, and phenanthroline derivatives. For example, bathocuproine (BCP) represented by the following formula may be used as a material for forming the HBL.

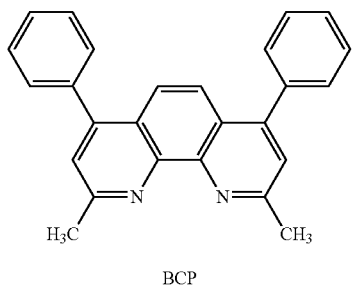 [SMILES: Cc1cc(-c2ccccc2)c2ccc3c(-c4ccccc4)cc(C)nc3c2n1 ; "BCP"]

BCP

The thickness of the HBL may be from about 20 Å to about 1000 Å, and in some embodiments, may be from about 30 Å to about 300 Å. When the thickness of the HBL is within these ranges, the HBL may have improved hole blocking ability without a substantial increase in driving voltage.

According to some embodiments, the organic light-emitting device may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

In some embodiments the organic layer of the organic light-emitting device may comprise the compound of Formula 1 by using a deposition method or may be formed using a wet method of coating a solution of the compound of Formula 1.

Hereinafter, the present embodiments will be described in detail with reference to the following synthesis examples and other examples. However, these examples are for illustrative purposes only and are not intended to limit the scope of the present embodiments.

EXAMPLES

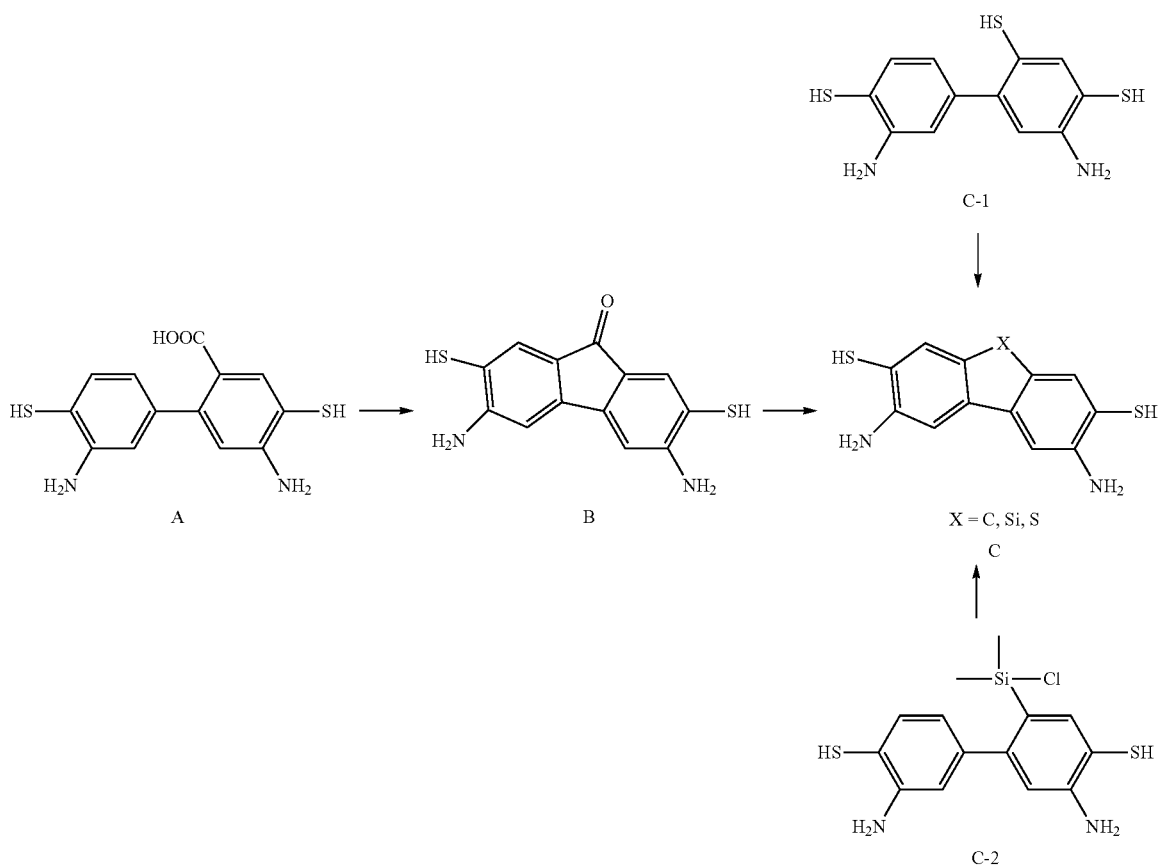

Synthesis Example 1

Synthesis of Intermediate B

After 1 g of Intermediate A was put into a flask, 10 mL of polyphosphoric acid was added into the flask, heated at about 140° C. for 2 hours, and cooled down to about 50° C. or lower, followed by a slow addition of distilled water. The resulting solid product was filtered, washed with a small amount of methanol, and then dried to obtain Intermediate B.

Synthesis of Intermediate C

After 1 g of Intermediate A, C-1, or C-2 was put into a flask, 20 mL of THF was added, followed by cooling down to about −78° C. (acetone+dry ice) and a slow addition of 2 eq of n-BuLi. After the temperature of the mixture was increased to room temperature, distilled water was slowly added to the mixture. After completion of the reaction, the reaction product was extracted with methylene chloride (MC), followed by column chromatography to obtain Intermediate C.

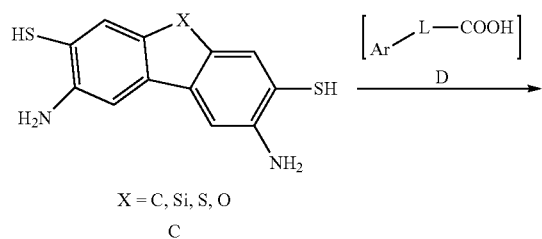

X = C, Si, S, O
C

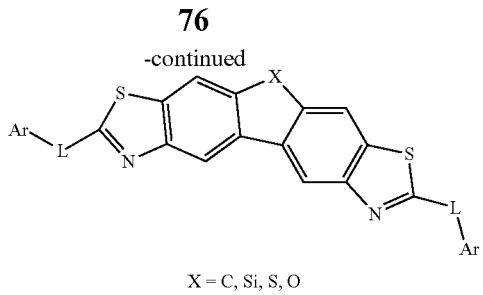

X = C, Si, S, O

Synthesis Example 2

After Intermediates C and D were put into a flask, 500 mL of polyphosphoric acid (PPA) was added thereinto, and refluxed at about 140° C. for about 24 hours while stirring. After completion of the reaction, the reaction product was cooled to room temperature, and a saturated sodium hydroxide solution was slowly added to adjust pH to be neutral, followed by filtration in a reduced pressure to obtain a solid product, which was then washed with ethanol, dried, and separated by column chromatography to obtain Compounds 1 to 30.

Compound 1

1

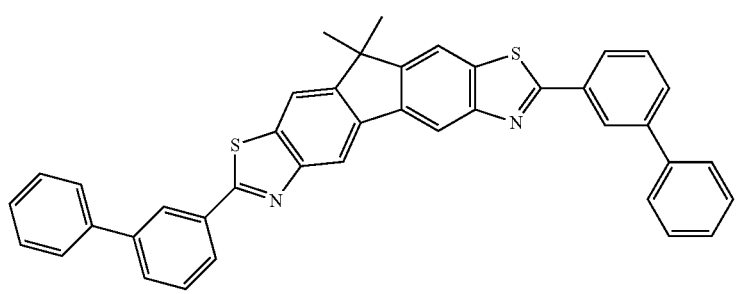

Elemental Analysis for C41H28N2S2: calcd C, 80.36; H, 4.61; N, 4.57; S, 10.47
HRMS for C41H28N2S2 [M]+: calcd 612.17, found 611.

Compound 4

4

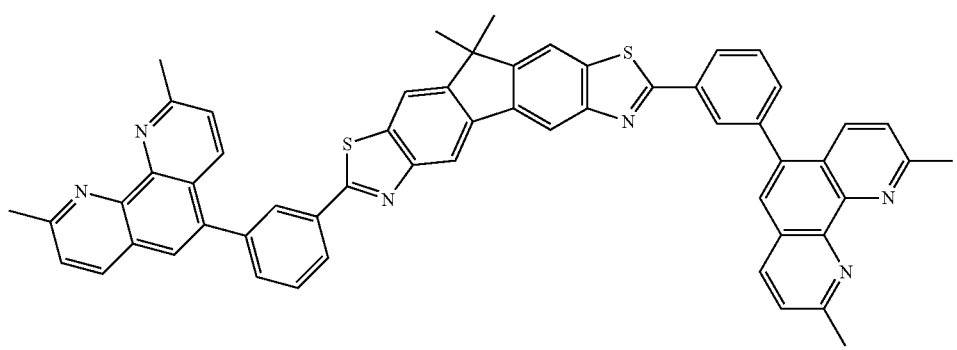

Elemental Analysis for C57H40N6S2: calcd C, 78.41; H, 4.62; N, 9.63; S, 7.35
HRMS for C57H40N6S2 [M]+: calcd 872.28, found 871

Compound 5
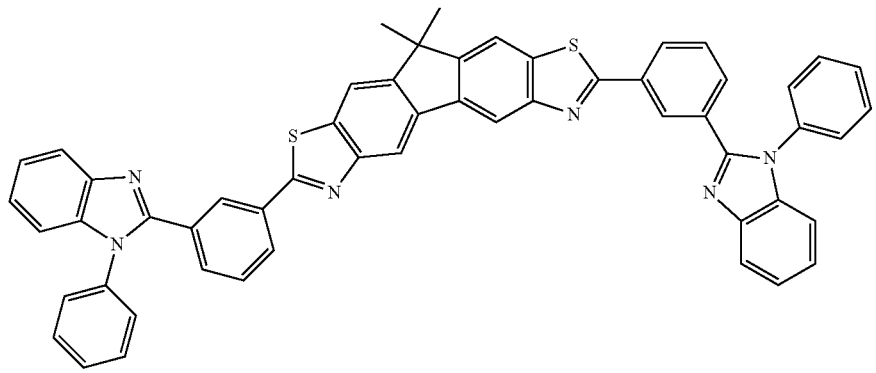
5
Elemental Analysis for C55H36N6S2: calcd C, 78.17; H, 4.29; N, 9.95; S, 7.59
HRMS for C55H36N6S2 [M]+: calcd 844.24, found 843
Compound 6
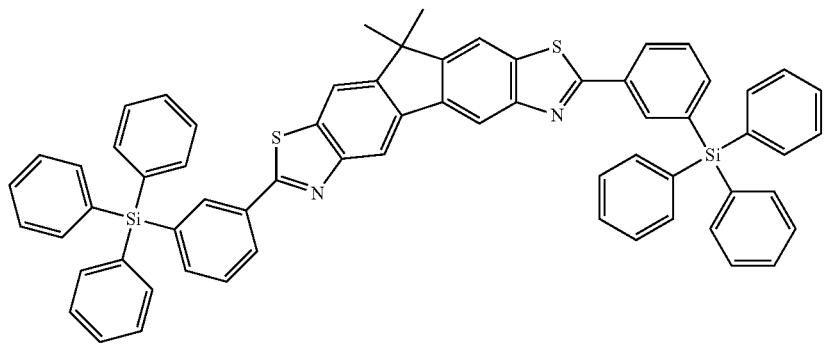
6
Elemental Analysis for C65H48N2S2Si2: calcd C, 79.88; H, 4.95; N, 2.87; S, 6.56; Si, 5.75
HRMS for C65H48N2S2Si2 [M]+: calcd 976.28, found 975
Compound 10
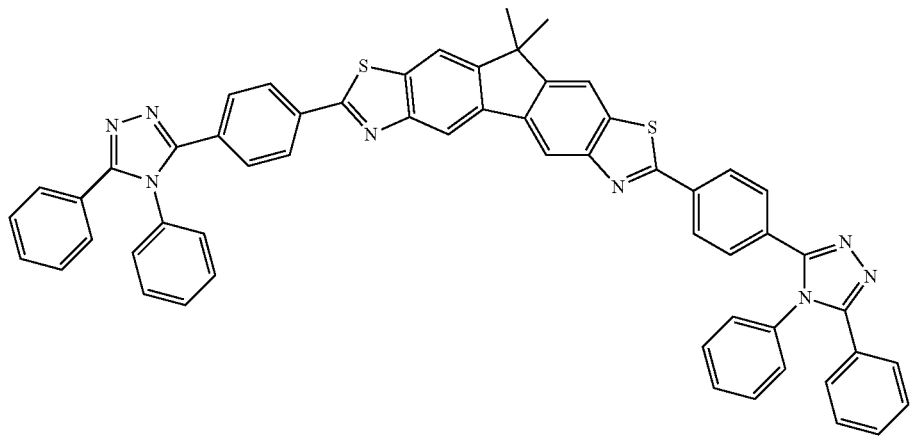
10
Elemental Analysis for C57H38N8S2: calcd C, 76.14; H, 4.26; N, 12.46; S, 7.13
HRMS for C57H38N8S2 [M]+: calcd 898.27, found 897

Compound 19
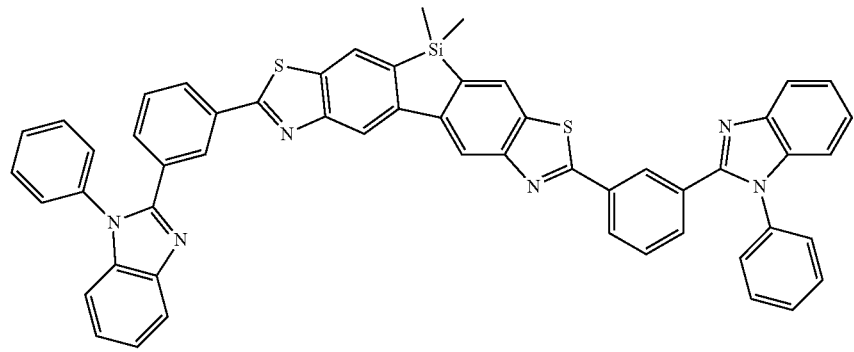
Elemental Analysis for C54H36N6S2Si: calcd C, 75.32; H, 4.21; N, 9.76; S, 7.45; Si, 3.26
HRMS for C54H36N6S2Si [M]+: calcd 860.22, found 859
Compound 23
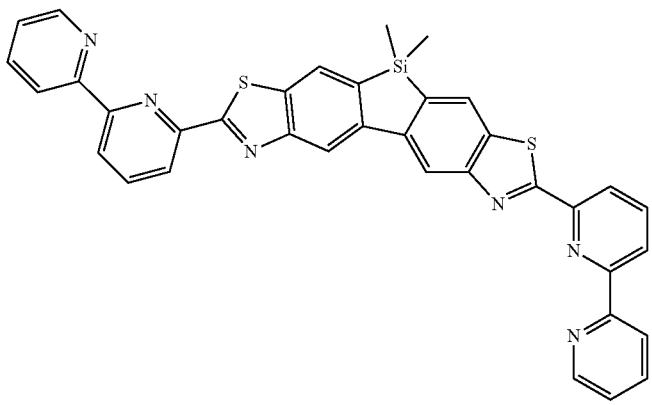
Elemental Analysis for C36H24N6S2Si: calcd C, 68.33; H, 3.82; N, 13.28; S, 10.13; Si, 4.44
HRMS for C36H24N6S2Si [M]+: calcd 632.13, found 631
Compound 26
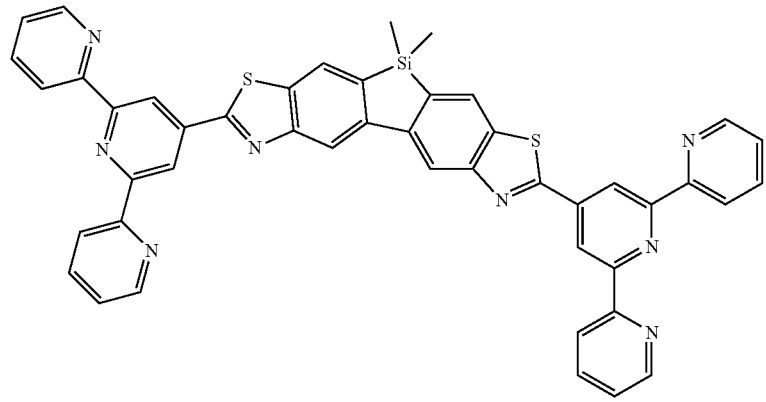
Elemental Analysis for C46H30N8S2Si: calcd C, 70.20; H, 3.84; N, 14.24; S, 8.15; Si, 3.57
HRMS for C46H30N8S2Si [M]+: calcd 786.18, found 785

Compound 30
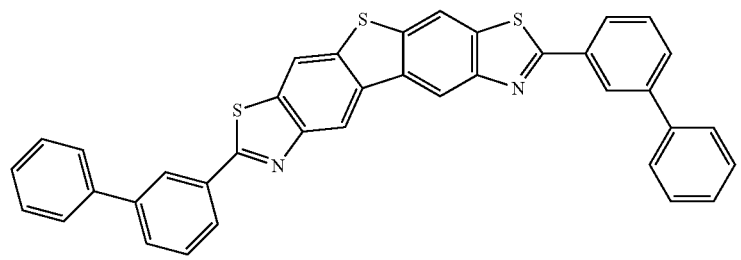
30
Elemental Analysis for C38H22N2S3: calcd C, 75.72; H, 3.68; N, 4.65; S, 15.96
HRMS for C38H22N2S3 [M]+: calcd 602.09, found 602
Compound 31
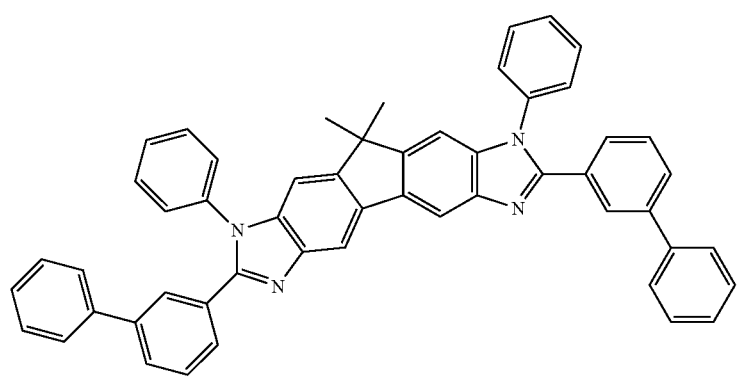
31
Elemental Analysis for C53H38N4: calcd C, 87.09; H, 5.24; N, 7.67
HRMS for C53H38N4 [M]+: calcd 730.31, found 729
Compound 35
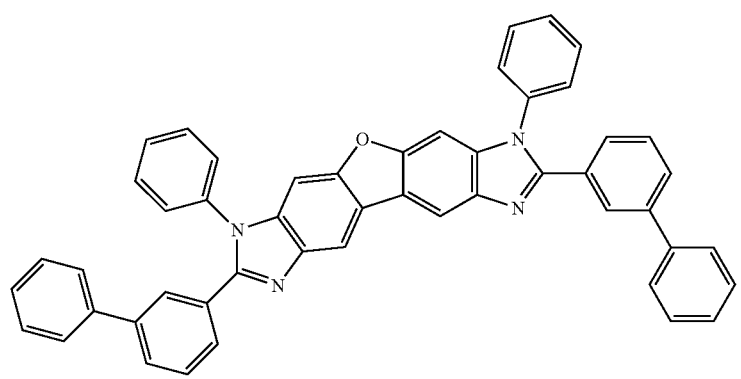
35
Elemental Analysis for C50H32N4O: calcd C, 87.09; H, 5.24; N, 7.67
HRMS for C50H32N4O [M]+: calcd 704.26, found 703

Examples and Comparative Examples

To manufacture an anode, a corning 15 Ω/cm2 (500 Å) ITO glass substrate was cut to a size of 50 mm×50 mm×0.5 mm and then sonicated in isopropyl alcohol and pure water each for 10 minutes, and then cleaned by irradiation of ultraviolet rays for 10 minutes and exposure to ozone. The resulting glass substrate was loaded into a vacuum deposition device. Then, 2-TNATA, which is a HIL material, was vacuum-deposited on the glass substrate to form a HIL having a thickness of about 600 Å. Then, 4,4'-bis[N-(1-naphthyl)-N-phenylamino]biphenyl (NPB), which is a hole transporting compound, was vacuum-deposited on the HIL to form a HTL having a thickness of about 300 Å.

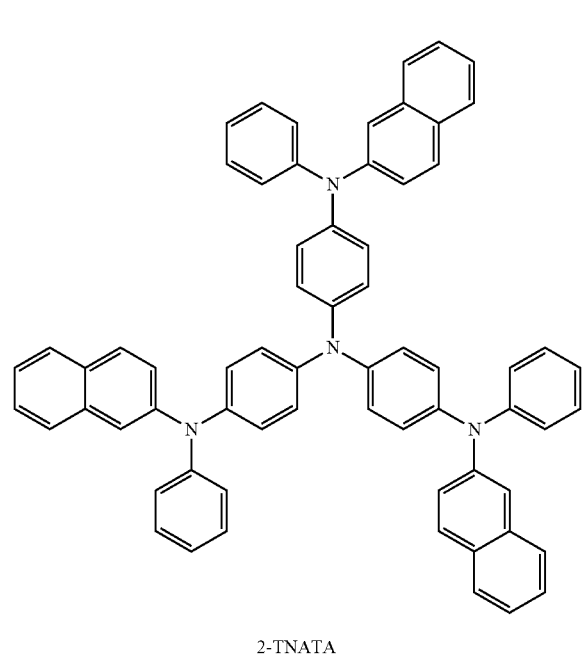

2-TNATA

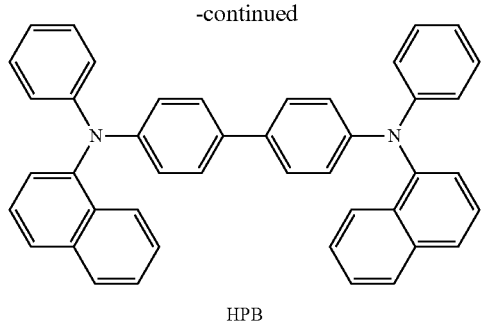

HPB 9,10-di(naphthalen-2-yl)anthracene (ADN) as a host and DNTPD as a dopant were deposited on the HTL to form an EML having a thickness of about 300 Å. Compounds 1, 4, 5, 6, 19, 23, 2, 30 as electron transport materials were respectively deposited on the EML to a thickness of about 250 Å in Examples, while aluminum tris(8-hydroxyquinoline) (Alq3) was deposited on the EML to form an ETL in Comparative Example 1. LiF and Al were sequentially deposited on the ETL to a thickness of about 10 Å and about 2,000 Å, respectively, to form an EIL and a cathode, thereby manufacturing organic light-emitting devices.

A structure of the organic light-emitting device including the compound of Formula 1 is shown in Table 1. A structure of the organic light-emitting device including the known compound (Alq3) is shown in Table 2.

TABLE 1

|  | HIL | HTL | EML | ETL | EIL | Cathode |
| --- | --- | --- | --- | --- | --- | --- |
| Materials | 2-TNATA | NPB | ADN + DNTPD | Formula 1 | LiF | Al |
| Thickness/Å | 600 | 150 | 285 + 15 | 250 | 10 | 2,000 |
| Evapo. Temp./° C. | 330~340 | 240~250 | Host: 260~270<br>Dopant: 240~250 | 330~340 | — | — |
| Vacuum/torr | $4.9 \times 10^{-7}$ | $4.9 \times 10{-7}$ | $4.2 \times 10^{-7}$ | $4.1 \times 10{-7}$ |  |  |

TABLE 2

|  | HIL | HTL | EML | ETL | EIL | Cathode |
| --- | --- | --- | --- | --- | --- | --- |
| Materials | 2-TNATA | NPB | ADN + DNTPD | Alq3 | LiF | Al |
| Thickness/Å | 600 | 150 | 285 + 15 | 250 | 10 | 2,000 |
| Evapo. Temp./° C. | 330~340 | 240~250 | Host: 260~270<br>Dopant: 240~250 | 260~270 | — | — |
| Vacuum/torr | $4.9 \times 10^{-7}$ | $4.9 \times 10^{-7}$ | $4.2 \times 10^{-7}$ | $5.7 \times 10^{-7}$ |  |  |

The organic light-emitting devices including the compounds of Formula 1 as an ETL material were found to have lower driving voltages and better I-V-L characteristics with improved efficiencies, compared to the organic light-emitting device using the known material Alq3. Typical characteristics of the organic light-emitting devices are summarized in Table 3.

TABLE 3

| | Current Density (mA/m$^2$) | Voltage (V) | Luminance (cd/m$^2$) | Efficiency (cd/A) | Efficiency (lm/W) |
|---|---|---|---|---|---|
| Compound 1 | 10 | 5.1 | 623 | 6.2 | 3.8 |
| Compound 4 | 10 | 5.0 | 642 | 6.4 | 3.9 |
| Compound 5 | 10 | 4.8 | 651 | 6.5 | 4.0 |
| Compound 6 | 10 | 4.8 | 650 | 6.5 | 4.0 |
| Compound 10 | 10 | 5.2 | 640 | 6.3 | 3.9 |
| Compound 19 | 10 | 4.6 | 694 | 6.7 | 4.2 |
| Compound 23 | 10 | 5.1 | 627 | 6.5 | 4.7 |
| Compound 26 | 10 | 4.9 | 653 | 6.1 | 3.9 |
| Compound 30 | 10 | 4.3 | 677 | 6.3 | 4.2 |
| Compound 31 | 10 | 5.0 | 699 | 6.7 | 3.9 |
| Compound 35 | 10 | 5.1 | 701 | 7.4 | 4.9 |
| Alq3 | 10 | 5.7 | 600 | 6.0 | 3.3 |

As described above, according to the one or more of the above embodiments, a heterocyclic compound of Formula 1 above has a good charge transporting capability, and thus may be used as a electron transport material that is suitable for fluorescent or phosphorescent devices of any color of red, green, blue, and white. An organic light-emitting device with high efficiency, low-driving voltage, high luminance, and long lifetime may be manufactured using the heterocyclic compound of Formula 1.

It should be understood that the example embodiments described therein should be considered in a descriptive sense only and not for purposes of limitation. Descriptions of features or aspects within each embodiment should typically be considered as available for other similar features or aspects in other embodiments.

What is claimed is:

1. A heterocyclic compound represented by Formula 1 below:

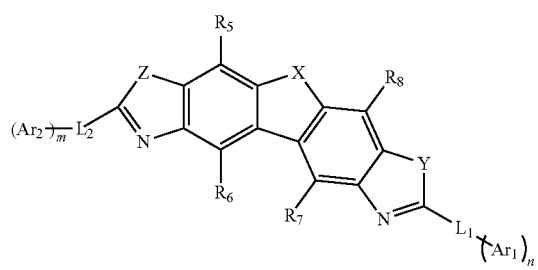

Formula 1 wherein, in Formula 1,
X is $CR_1R_2$, $SiR_3R_4$, S, or O;
Y and Z are each independently S, or O;
$R_1$ to $R_8$ are each independently a hydrogen atom, a deuterium atom, a cyano group, a substituted or unsubstituted C1-20 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C3-C60 cycloalkenyl group, a substituted or unsubstituted C6-C60 aryl group, a substituted or unsubstituted C2-C60 heteroaryl group, or a substituted or unsubstituted C6-C60 condensed polycyclic group;

$L_1$ and $L_2$ are each independently a bond, a substituted or unsubstituted C6-C60 arylene group, or a substituted or unsubstituted C2-C60 heteroarylene group;

$Ar_1$ to $Ar_2$ are the same or different, and are each independently a substituted or unsubstituted C2-C60 heteroaryl group, a substituted or unsubstituted C6-C60 aryl group, or a substituted or unsubstituted C6-C60 condensed polycyclic group; and m and n are each independently an integer from 0 to 3, and m and n are not both zero.

2. The heterocyclic compound of claim 1, wherein $R_5$ to $R_8$ in Formula 1 are each independently a hydrogen atom, or a deuterium atom.

3. The heterocyclic compound of claim 1, wherein $L_1$ and $L_2$ in Formula 1 are each independently a bond, or a group represented by Formula 2a below:

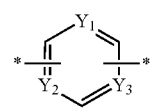

2a wherein, in Formula 2a, $Y_1$ to $Y_3$ are each independently CH or N.

4. The heterocyclic compound of claim 1, wherein $Ar_1$ and $Ar_2$ in Formula 1 are each independently one of the groups represented by Formulae 3a to 3g:

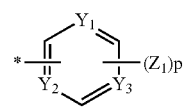

3a

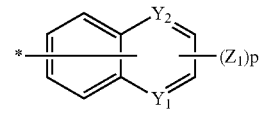

3b

-continued

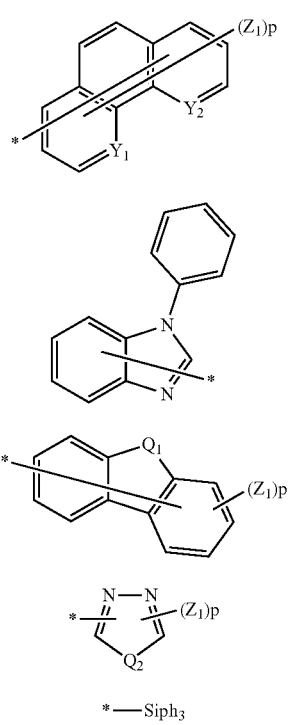

wherein, in Formulae 3a to 3g, $Y_1$ to $Y_3$ are each independently CH or N;

$Q_1$ is $SiR_{50}R_{51}$;

$Q_2$ is S or $NR_{60}$;

$R_{50}$, $R_{51}$, $R_{60}$, and $Z_1$ are each independently a hydrogen atom, a deuterium atom, a substituted or unsubstituted C1-20 alkyl group, a substituted or unsubstituted C6-C20 aryl group, a substituted or unsubstituted C2-C20 heteroaryl group, a substituted or unsubstituted C6-C20 condensed polycyclic group, an amino group substituted with a C6-C20 aryl group or a C2-C20 heteroaryl group, a halogen group, a cyano group, a nitro group, a hydroxy group, or a carboxyl group, wherein a plurality of $Z_1$s are the same or different;

p is an integer from 1 to 7; and

* indicates a binding site.

5. The heterocyclic compound of claim 1, wherein adjacent substituents of $R_1$ to $R_4$ in Formula 1 are linked to each other to form a ring.

6. The heterocyclic compound of claim 1, wherein, when $Ar_1$ or $Ar_2$ in Formula 1 is plural, adjacent substituents of $Ar_1$ or $Ar_2$ are linked to each other to form a ring.

7. The heterocyclic compound of claim 1, wherein the compound of Formula 1 is one of the compounds below:

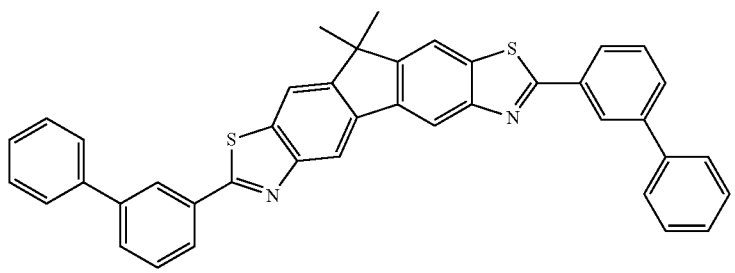

1

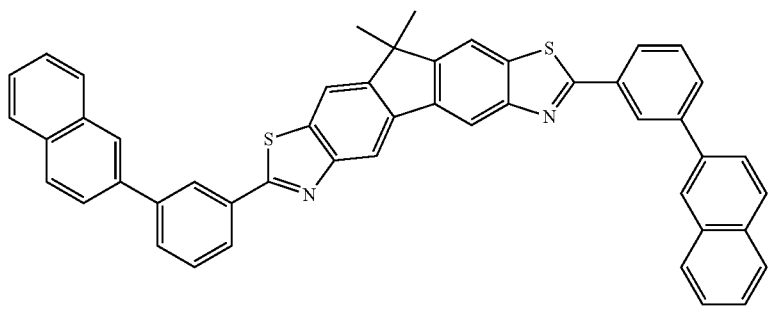

2

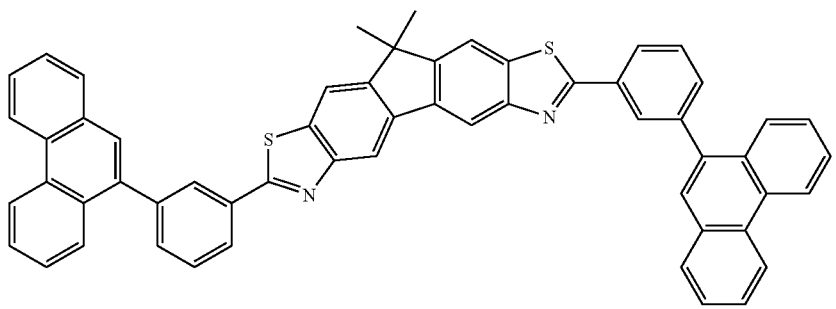

3

-continued
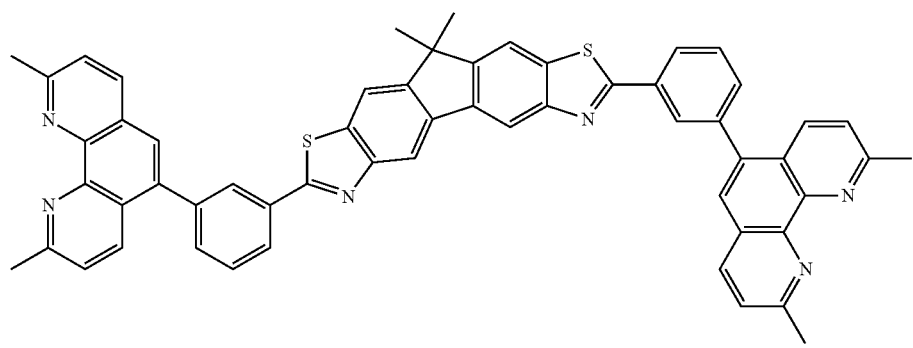
4
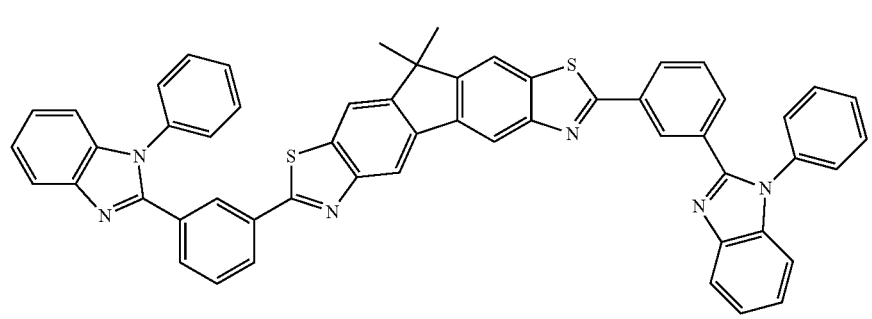
5
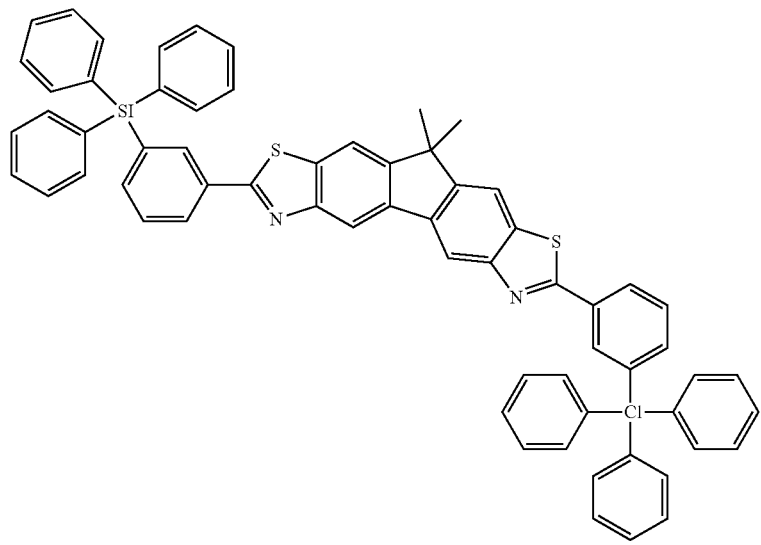
6
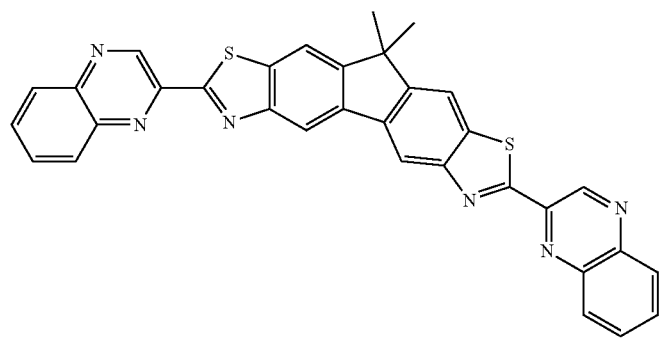
7

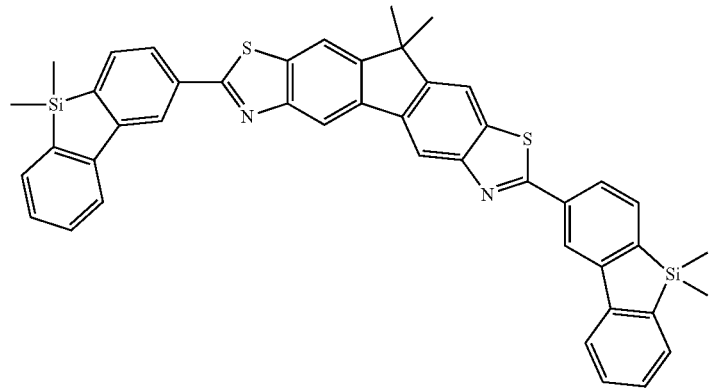
8
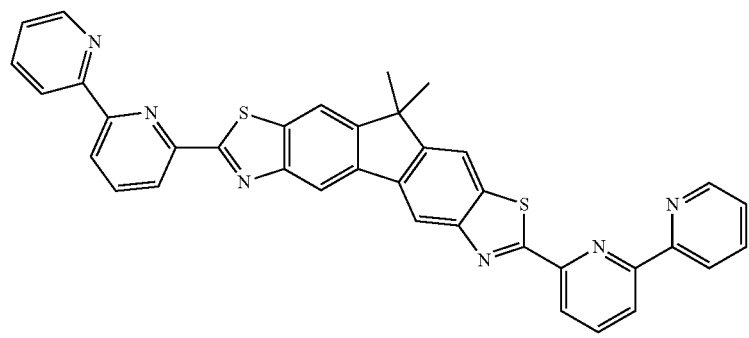
9
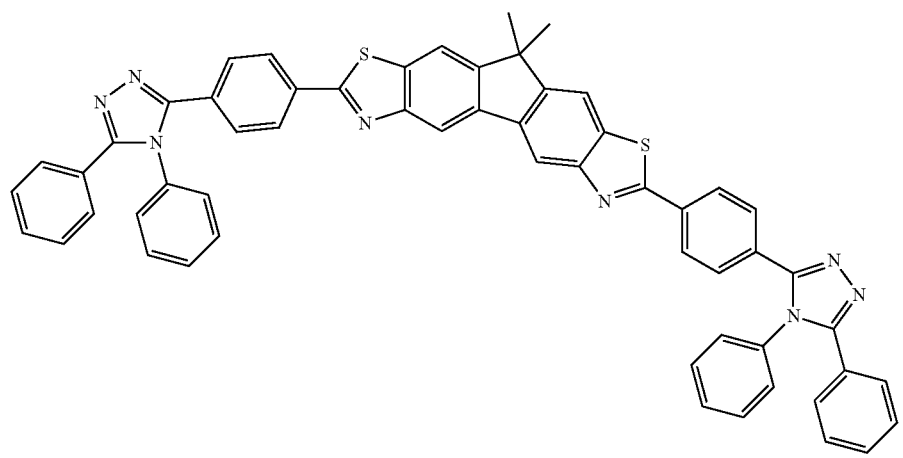
10
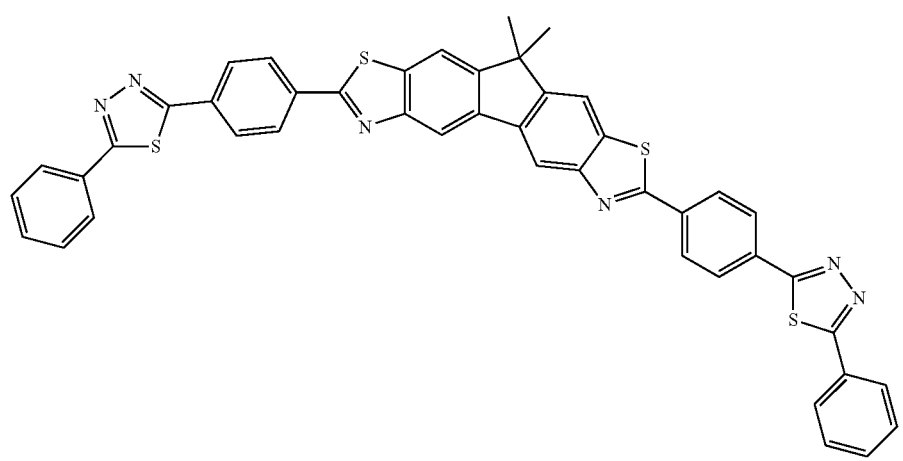
11

12
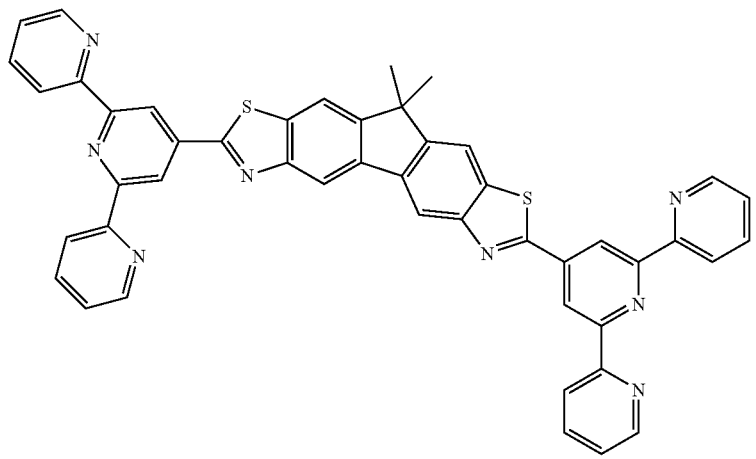
13
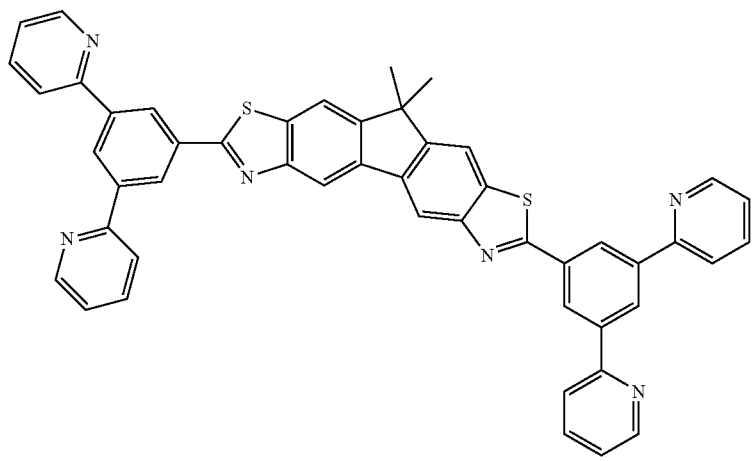
14
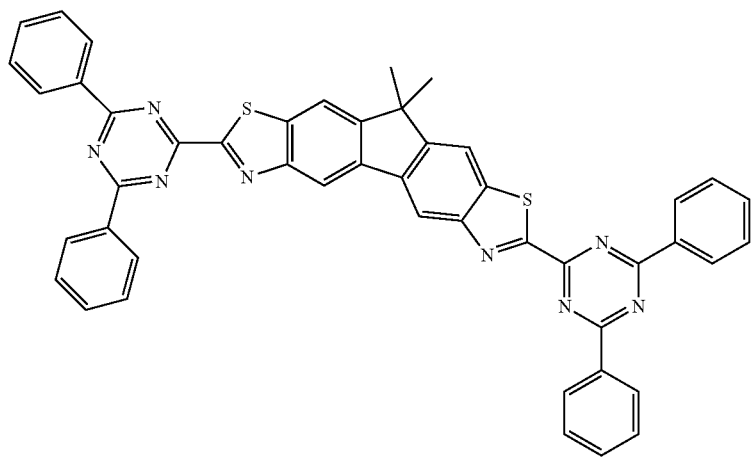
15
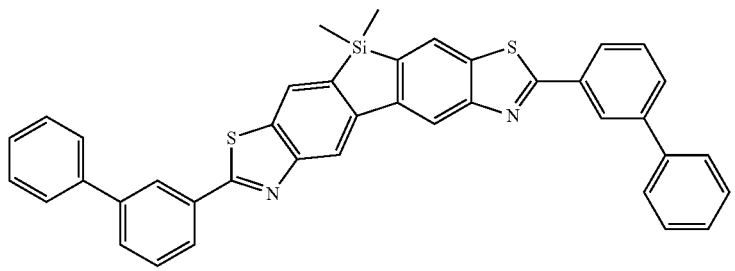

16
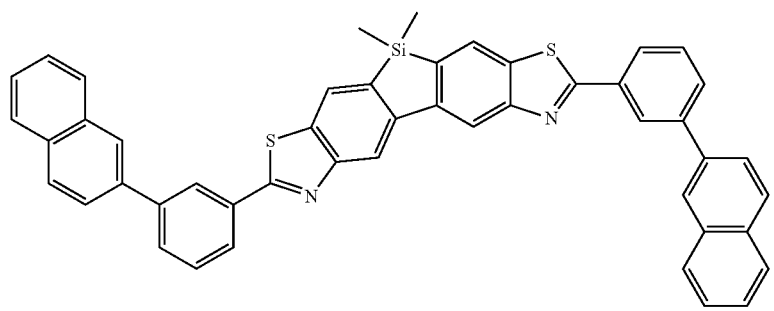
17
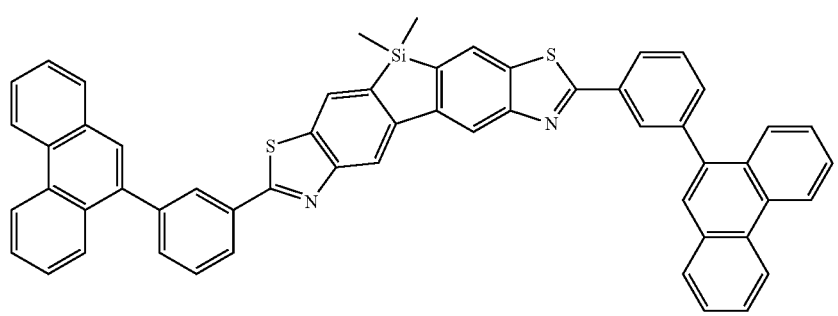
18
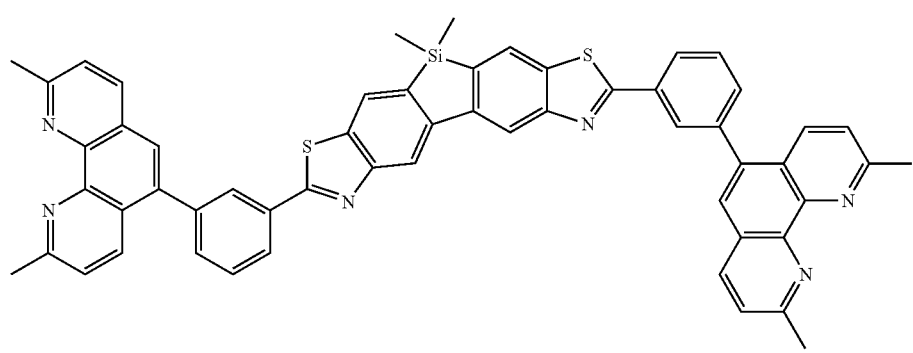
19
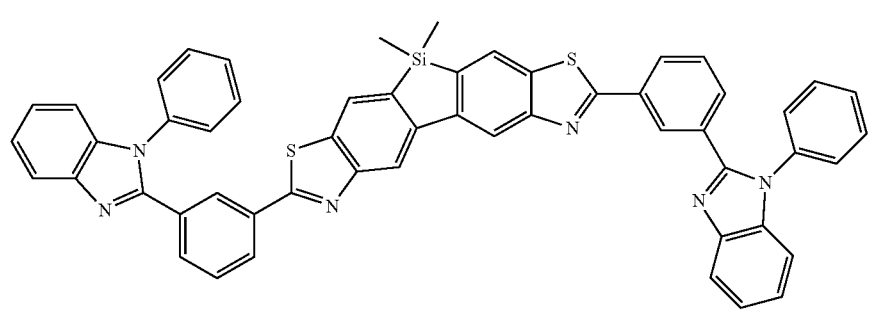

20
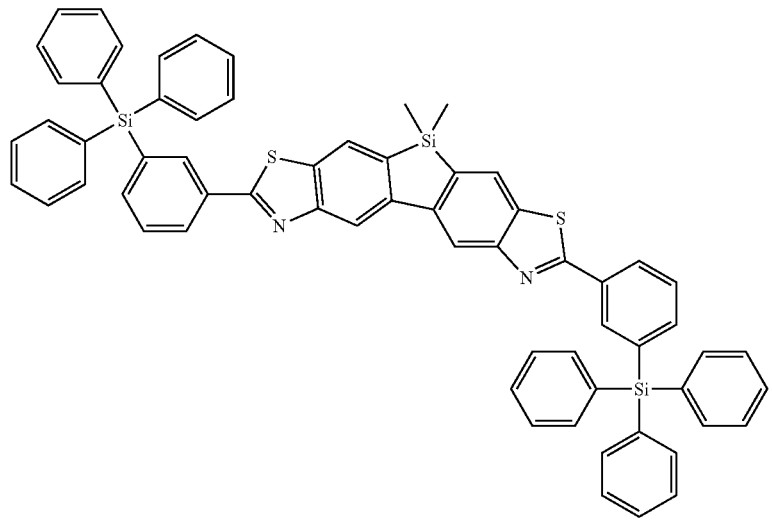
21
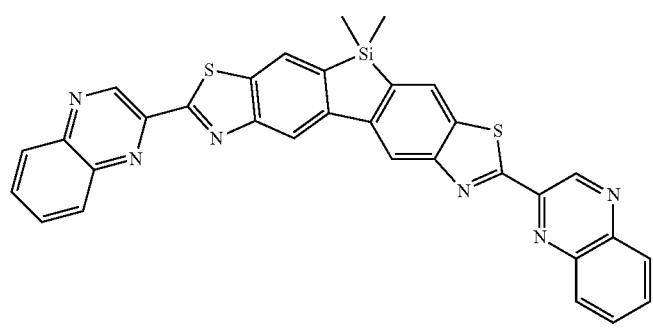
22
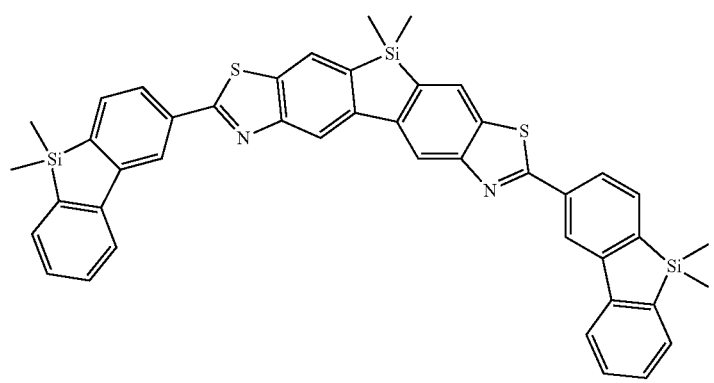
23
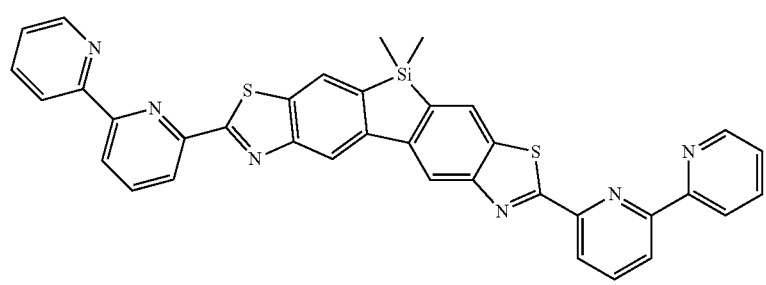

-continued
24
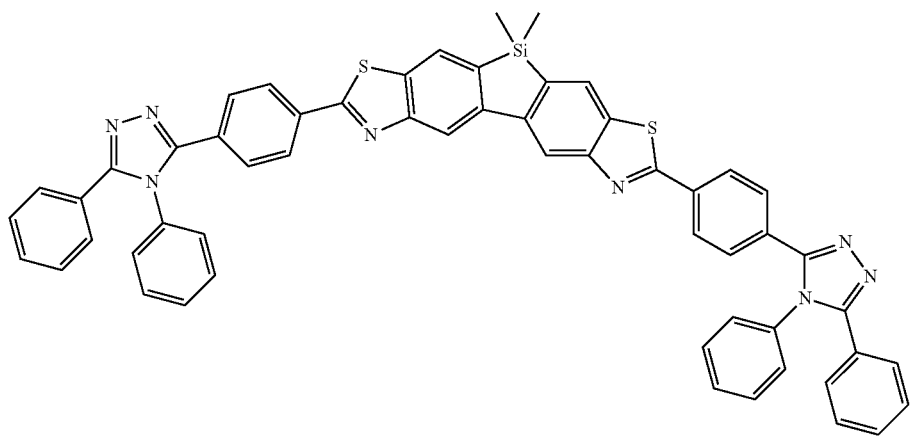
25
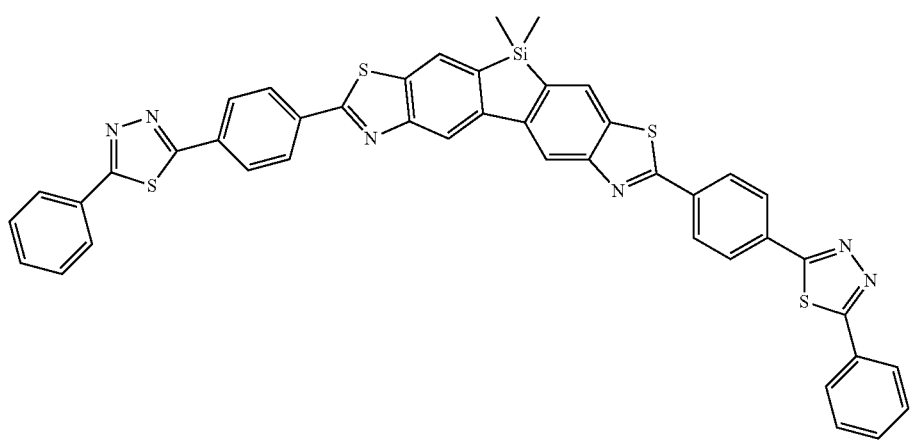
26
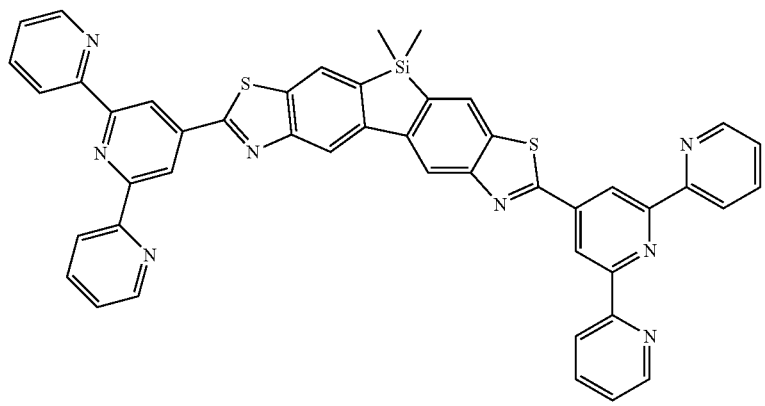

-continued
27
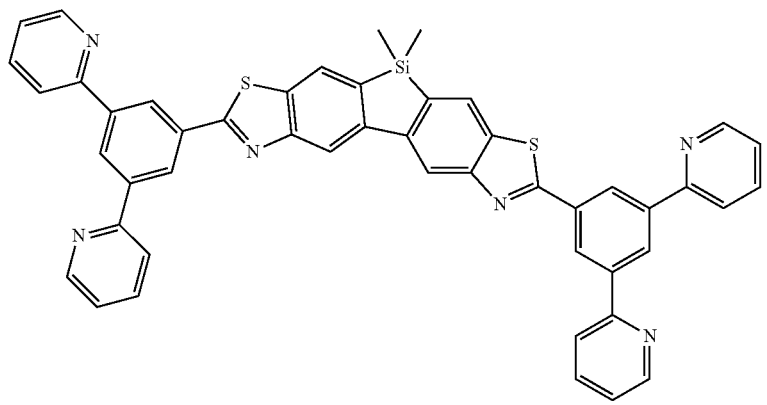
28
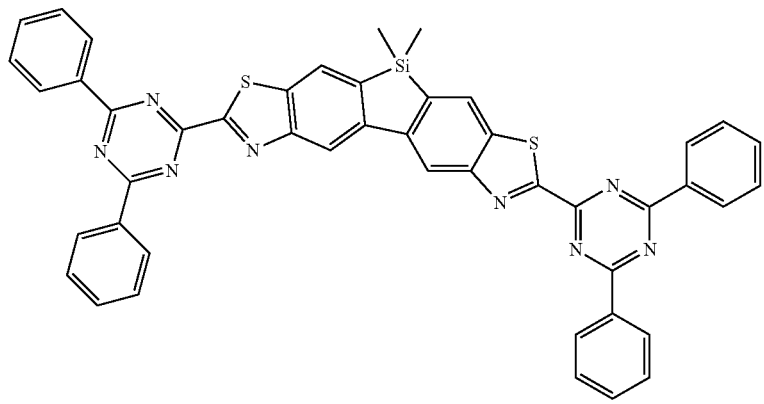
29
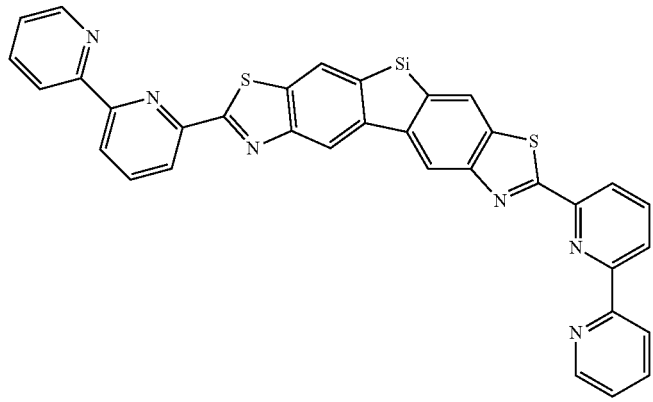
30
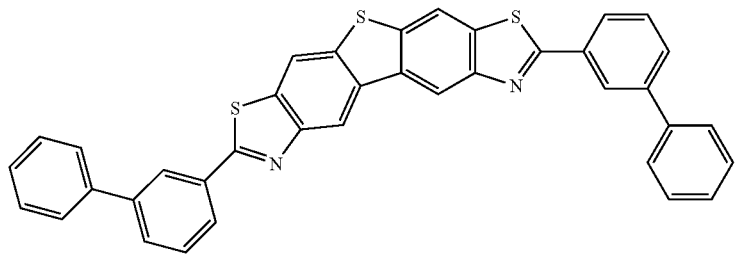

31
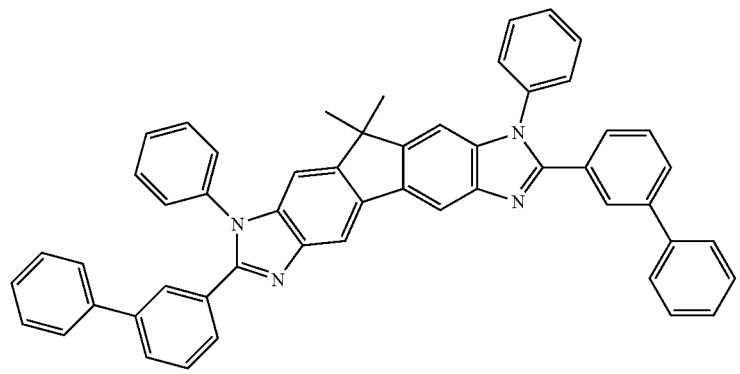
32
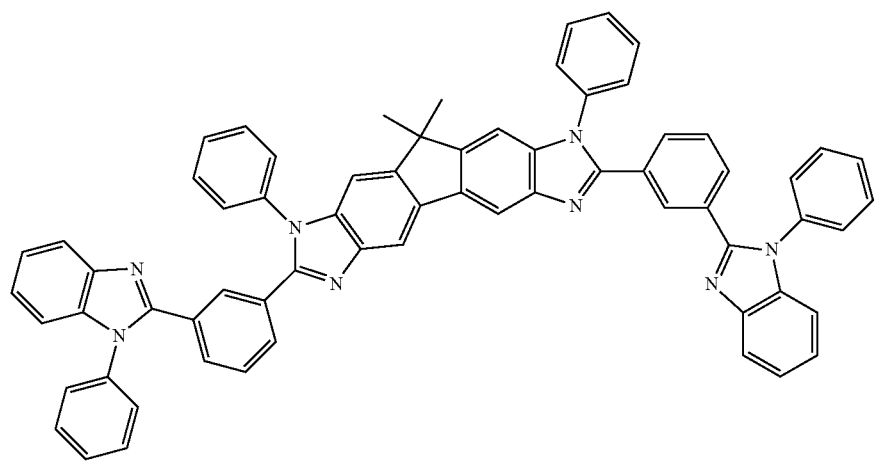
33
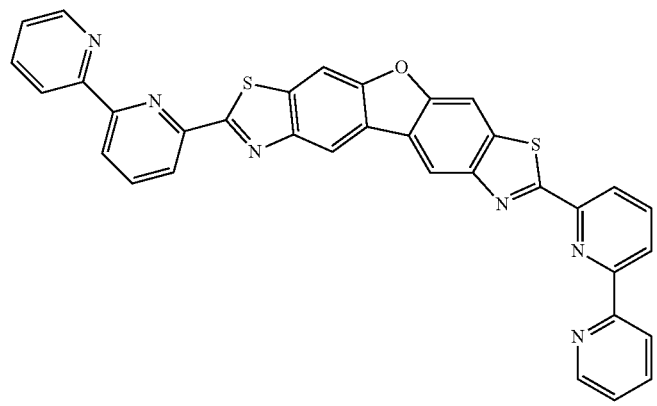
34
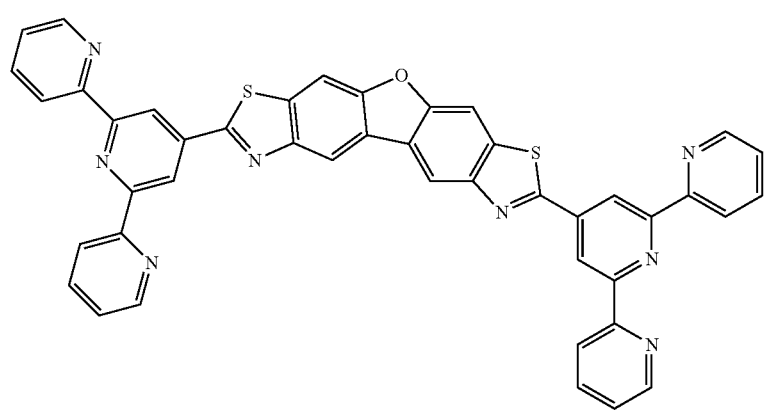

35

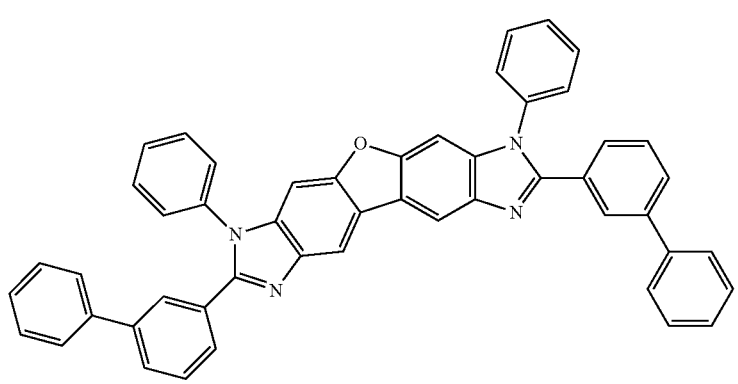

36

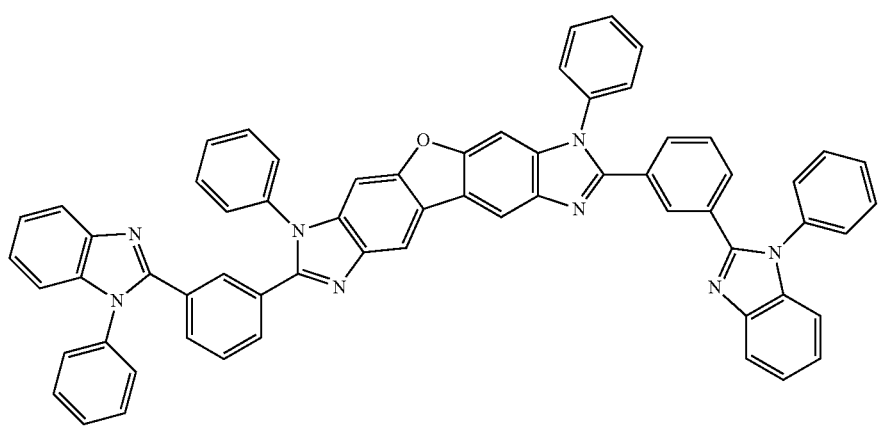

8. An organic light-emitting device comprising:
a first electrode;
a second electrode; and
an organic layer disposed between the first electrode and the second electrode, and comprising a heterocyclic compound represented by Formula 1 below:

Formula 1

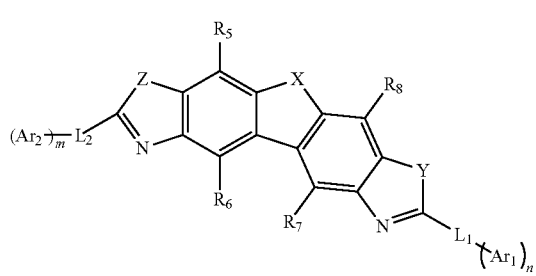

wherein, in Formula 1,
X is $CR_1R_2$, $SiR_3R_4$, S, or O;
Y and Z are each independently S, or O;
$R_1$ to $R_8$ are each independently a hydrogen atom, a deuterium atom, a cyano group, a substituted or unsubstituted C1-20 alkyl group, a substituted or unsubstituted C2-C60 alkenyl group, a substituted or unsubstituted C2-C60 alkynyl group, a substituted or unsubstituted C3-C60 cycloalkyl group, a substituted or unsubstituted C3-C60 cycloalkenyl group, a substituted or unsubstituted C6-C60 aryl group, a substituted or unsubstituted C2-C60 heteroaryl group, or a substituted or unsubstituted C6-C60 condensed polycyclic group;
$L_1$ and $L_2$ are each independently a bond, a substituted or unsubstituted C6-C60 arylene group, or a substituted or unsubstituted C2-C60 heteroarylene group;
$Ar_1$ to $Ar_2$ are the same or different, and are each independently a substituted or unsubstituted C2-C60 heteroaryl group, a substituted or unsubstituted C6-C60 aryl group, or a substituted or unsubstituted C6-C60 condensed polycyclic group; and
m and n are each independently an integer from 0 to 3, and m and n are not both zero.

9. The organic light-emitting device of claim 8, wherein the organic layer is an electron transport layer (ETL).

10. The organic light-emitting device of claim 8, wherein the organic layer comprises an emission layer, an electron injection layer, an electron transport layer, a functional layer having both electron injection and transport capabilities; a hole injection layer, a hole transport layer, or a functional layer having both hole injection and transport capabilities, and the emission layer comprises an anthracene compound, an arylamine compound, or a styryl compound.

11. The organic light-emitting device of claim 8, wherein the organic layer comprises an emission layer, an electron injection layer, an electron transport layer, a functional layer having both electron injection and transport capabilities; a hole injection layer, a hole transport layer, or a functional layer having both hole injection and transport capabilities, and the emission layer comprises red, green, blue, and white emission layers one of which comprises a phosphorescent compound.

12. The organic light-emitting device of claim 11, wherein at least one of the hole injection layer, the hole transport layer, and the functional layer having both hole injection and hole transport capabilities comprises a charge-generating material.

13. The organic light-emitting device of claim 12, wherein the charge-generating material is a p-type dopant.

14. The organic light-emitting device of claim 13, wherein the p-dopant is a quinone derivative.

15. The organic light-emitting device of claim 13, wherein the p-dopant is a metal oxide.

16. The organic light-emitting device of claim 13, wherein the p-dopant is a cyano group-containing compound.

17. The organic light-emitting device of claim 8, wherein the organic layer comprises an electron transport layer, and the electron transport layer further comprises a metal complex.

18. The organic light-emitting device of claim 17, wherein the metal complex is a Li complex.

19. The organic light-emitting device of claim 8, wherein the organic layer is formed from the heterocyclic compound of claim 1 using a wet process.

20. A flat panel display device comprising the organic light-emitting device of claim 8, wherein the first electrode of the organic light-emitting device is electrically connected to a source electrode or a drain electrode of a thin-film transistor.

* * * * *